US007098308B2

(12) United States Patent
Senter et al.

(10) Patent No.: US 7,098,308 B2
(45) Date of Patent: Aug. 29, 2006

(54) PENTAPEPTIDE COMPOUNDS AND USES RELATED THERETO

(75) Inventors: Peter D. Senter, Seattle, WA (US); Brian E. Toki, Lynnwood, WA (US); Svetlana Doronina, Bothell, WA (US)

(73) Assignee: Seattle Genetics, Inc., Bothell, WA (US)

(*) Notice: Subject to any disclaimer, the term of this patent is extended or adjusted under 35 U.S.C. 154(b) by 31 days.

(21) Appl. No.: 10/979,923

(22) Filed: Nov. 1, 2004

(65) Prior Publication Data

US 2005/0113308 A1    May 26, 2005

Related U.S. Application Data

(60) Division of application No. 10/001,191, filed on Nov. 1, 2001, now Pat. No. 6,884,869, which is a continuation-in-part of application No. 09/845,786, filed on Apr. 30, 2001, now abandoned.

(51) Int. Cl.
*C07K 7/00* (2006.01)
(52) U.S. Cl. ............................ 530/330; 514/17; 514/18
(58) Field of Classification Search ................ 530/330; 514/17, 18
See application file for complete search history.

(56) References Cited

U.S. PATENT DOCUMENTS

| | | | |
|---|---|---|---|
| 4,414,205 A | 11/1983 | Pettit | |
| 4,816,444 A | 3/1989 | Pettit et al. | |
| 4,879,278 A | 11/1989 | Pettit et al. | |
| 4,978,744 A | 12/1990 | Pettit et al. | |
| 5,410,024 A | 4/1995 | Pettit et al. | |
| 5,521,284 A | 5/1996 | Pettit et al. | |
| 5,530,097 A | 6/1996 | Pettit et al. | |
| 5,554,725 A | 9/1996 | Pettit | |
| 5,599,902 A | 2/1997 | Pettit et al. | |
| 5,635,483 A | 6/1997 | Pettit et al. | |
| 5,654,399 A | 8/1997 | Sakakibara et al. | |
| 5,663,149 A | 9/1997 | Pettit et al. | |
| 5,665,860 A | 9/1997 | Pettit et al. | |
| 5,741,892 A | 4/1998 | Barlozzari et al. | |
| 5,767,236 A | 6/1998 | Kim et al. | |
| 5,767,237 A | 6/1998 | Sakakibara et al. | |
| 5,780,588 A | 7/1998 | Pettit et al. | |
| 5,840,699 A | 11/1998 | Sakakibara et al. | |
| 6,004,934 A | 12/1999 | Sakakibara et al. | |
| 6,034,065 A | 3/2000 | Pettit et al. | |
| 6,124,431 A | 9/2000 | Sakakibara et al. | |
| 6,162,930 A | 12/2000 | Pinney et al. | |
| 6,239,104 B1 | 5/2001 | Pettit et al. | |
| 6,342,221 B1 | 1/2002 | Thorpe et al. | |
| 2001/0018422 A1 | 8/2001 | Ritter et al. | |

FOREIGN PATENT DOCUMENTS

| | | |
|---|---|---|
| EP | 598 129 A1 | 5/1994 |
| EP | 0695757 | 2/1996 |
| EP | 0695758 | 2/1996 |
| EP | 0695759 | 2/1996 |
| WO | WO 93/03054 | 2/1993 |
| WO | WO 95/09864 | 4/1995 |
| WO | WO 96/14856 | 5/1996 |
| WO | WO 96/33212 | 10/1996 |
| WO | WO 01/18032 | 3/2001 |
| WO | WO 04/010957 | 2/2004 |

OTHER PUBLICATIONS

Bowman et al. 1950, J. Chem. Soc. 1342-1340.
Miyazaki et al., 1995, "Synthesis and antitumor activity of novel dolastatin 10 analogs," Chem. Pharm. Bull. (Tokyo) 43(10):1706-1718.
Pettit, 1998, "Antineoplastic agents 365. Dolastatin 10 SAR probes," Anticancer Drug Des. 13(4):243-277.
Pettit, 1997, "The dolastatins," (reprint) Springer-Verlag, New York 70:1-79.
Pettit et al., 1996, "The Dolastatins 24. Synthesis of (-)-dolastatin 10. X-ray Molecular Structure of N,N-Dimethylvalyl-valyl-dolaisoleuine, Tert-Butyl Ester", J. Chem. Soc. Perk Trans. 1:859-863.
Pettit et al., 1995, "Antineoplastic agents 337. Synthesis of dolastatin 10 structural modifications," Anticancer Drug Des. 10(7):529-544.
Pettit et al., 1994, "The Dolastatins. 17. Synthesis of Dolaproine and Related Diastereoisomers,", J. Org. Chem. 59(21):6287-6295.
Pettit et al., 1996, "The Dolastatins. 18. Stereospecific Synthesis of Dolaproine,", Synthesis 6:719-725.
Pettit et al., 1994, "The Dolastatins. 19. Synthesis of Dolaisoleuine", J. Org. Chem. 59(7):1796-1800.
Petit et al., 1996, The Dolastatins. 23: Stereospecific Synthesis of Dolaisoleuine, J. Chem Soc. Perkin. Trans. 1:853-858.
Shioiri et al., 1993, "Stereoselective Synthesis of Dolastatin 10 and its Congeners," Tetrahedron 49(9):1913-1924.
Tomioka et al., 1991, An Expeditious Synthesis of Dolastatin 10, Tetrahedron Letters 32(21):2395-2398.
Toki et al., 2002, "Cures and Regressions of Established Tumor Xenographs with Monoclonal Antibody", 223rd ACS Meeting, Orlando FL, Apr. 7-11.

*Primary Examiner*—David Lukton
(74) *Attorney, Agent, or Firm*—Jones Day

(57) ABSTRACT

Pentapeptide compounds are disclosed. The compounds have biological activity, e.g., cytotoxicity. Prodrugs having targeting groups and pentapeptide moieities, as well as precursors thereof are also disclosed. For example, precursors having a reactive linker that can serve as a reaction site for joining to a targeting agent, e.g., an antibody, as disclosed.

6 Claims, 22 Drawing Sheets

(21) (1S,2R) $R^{18}$= OH, $R^{19}$= Me, $R^{20}$= H
(22) (S) $R^{18}$= H, $R^{19}$= $CH_2OH$, $R^{20}$= H
(23) (R) $R^{18}$= H, $R^{19}$= $CH_2OH$, $R^{20}$= H
(24) $R^{18}$= H, $R^{19}$= H, $R^{20}$= C(O)$CH_3$

(25) (1S, 2R) $R^{18}$= OH, $R^{19}$= Me, $R^{20}$= H
(26) (S) $R^{18}$= H, $R^{19}$= $CH_2OH$, $R^{20}$= H
(27) (R) $R^{18}$= H, $R^{19}$= $CH_2OH$, $R^{20}$= H
(28) $R^{18}$= H, $R^{19}$= H, $R^{20}$= C(O)$CH_3$

PENTAPEPTIDE COMPOUNDS AND USES RELATED THERETO

This application is a division of U.S. application Ser. No. 10/001,191, filed Nov. 1, 2001 now U.S. Pat. No. 6,884,869, which is a continuation-in-part of U.S. application Ser. No. 09/845,786, filed Apr. 30, 2001 now abandoned, the disclosures of which are incorporated by reference herein in their entireties.

TECHNICAL FIELD

The present invention is directed to biologically active organic compounds and precursors thereto, more specifically to pentapeptides and compositions containing these pentapeptides, and to methods for their use, e.g., as cytotoxic agents.

BACKGROUND OF THE INVENTION

Several short peptidic compounds have been isolated from natural sources and found to have biological activity. Analogs of these compounds have also been prepared, and some were found to have biological activity. For example, Auristatin E (Pettit, G. R., Barkoczy, J. "Tumor inhibiting tetrapeptide bearing modified phenethyl amides" U.S. Pat. No. 5,635,483) is a synthetic analogue of the marine natural product, dolastatin 10, an agent that inhibits tubulin polymerization by binding to the same site on tubulin as the anticancer drug vincristine (Pettit, G. R. "The dolastatins" *Prog. Chem. Org. Nat. Prod.* 1997, 70, 1–79). Dolastatin 10, auristatin PE, and auristatin E are linear peptides comprised of four amino acids, three of which are unique to this class of compounds. Both dolastatin 10 and auristatin PE are in human clinical trials. The structural differences between the drugs reside in the C-terminal residue, in which the thiazolephenethyl amine of dolastatin 10 is replaced by a norephedrine unit in auristatin E.

The following references disclose dolastatin and auristatin compounds and analogs thereof.

"Preparation of peptide derivatives as dolastatin 10 analogs with antitumor effects" Sakakibara, Kyoichi; Gondo, Masaaki; Miyazaki, Koichi; Ito, Takeshi; Sugimura, Akihiro; Kobayashi, Motohiro. (Teikoku Hormone Mfg. Co., Ltd., Japan; Sakakibara, Kyoichi; Gondo, Masaaki; Miyazaki, Koichi; Ito, Takeshi; Sugimura, Akihiro; Kobayashi, Motohiro). PCT International Patent Publication No. WO 9633212 A1 (1996);

"Preparation of dolastatin 10 analogs as cancer inhibitory peptides" Pettit, George R.; Srirangam, Jayaram K. (Arizona Board of Regents, USA). PCT International Patent Publication No. WO 9614856 A1 (1996);

"Preparation of tetra- and pentapeptide dolastatin analogs as anticancer agents" Pettit, George R.; Srirangam, Jayaram K.; Williams, Michael D. (Arizona Board of Regents, USA). Eur. Pat. Appl. No. EP 695757 A2 (1996);

"Preparation of dolastatin 10 analog pentapeptide amides and esters as anticancer agents" Pettit, George R.; Srirangam, Jayaram K. (Arizona Board of Regents, USA). Eur. Pat. Appl. No. EP 695758 A2 (1996);

"Preparation of dolastatin analog pentapeptide methyl esters as anticancer agents" Pettit, George R.; Williams, Michael D.; Srirangam, Jayaram K. (Arizona Board of Regents, USA). Eur. Pat. Appl. No. EP 695759 A2 (1996);

"Preparation of novel peptide derivative as antitumor agent" Sakakibara, Kyoichi; Gondo, Masaaki; Miyazaki, Koichi; Ito, Takeshi; Sugimura, Akihiro; Kobayashi, Motohiro. (Teikoku Hormone Mfg. Co., Ltd., Japan). PCT International Patent Publication No. WO 9509864 A1 (1995);

"Preparation of tetrapeptide derivatives as antitumor agents" Sakakibara, Kyoichi; Gondo, Masaaki; Miyazaki, Koichi. (Teikoku Hormone Mfg. Co., Ltd., Japan). PCT International Patent Publication No. WO 9303054 A1 (1993);

"Antineoplastic agents 365. Dolastatin 10 SAR probes" Pettit, George R.; Srirangam, Jayaram K.; Barkoczy, Jozsef; Williams, Michael D.; Boyd, Michael R.; Hamel, Ernest; Pettit, Robin K.; Hogan, Fiona; Bai, Ruoli; Chapuis, Jean-Charles; McAllister, Shane C.; Schmidt, Jean M., *Anti-Cancer Drug Des.* (1998), 13(4), 243–277;

"Antineoplastic agents. 337. Synthesis of dolastatin 10 structural modifications" Pettit, George R.; Srirangam, Jayaram K.; Barkoczy, Jozsef; Williams, Michael D.; Durkin, Kieran P. M.; Boyd, Michael R.; Bai, Ruoli; Hamel, Ernest; Schmidt, Jean M.; Chapius, Jean-Charles, *Anti-Cancer Drug Des.* (1995), 10(7), 529–44; and "Synthesis and antitumor activity of novel dolastatin 10 analogs" Miyazaki, Koichi; Kobayashi, Motohiro; Natsume, Tsugitaka; Gondo, Masaaki; Mikami, Takashi; Sakakibara, Kyoichi; Tsukagoshi, Shigeru, *Chem. Pharm. Bull.* (1995), 43(10), 1706–18.

There is a need in the art for improved antitumor agents. Despite promising in vitro data for dolastatin 10 and its analogs, significant general toxicities at doses required for achieving a therapeutic affect compromise their efficacy in clinical studies. The present invention is directed to fulfilling this need and provides further advantages as disclosed herein.

SUMMARY OF THE INVENTION

In one aspect, the present invention provides a compound of the formula

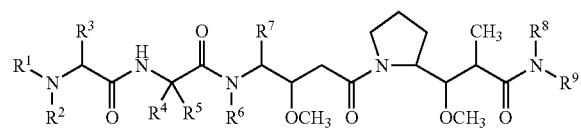

wherein, independently at each location:

$R^1$ is selected from hydrogen and lower alkyl;

$R^2$ is selected from hydrogen and lower alkyl;

$R^3$ is lower alkyl;

$R^4$ is selected from lower alkyl, aryl, and —$CH_2$—$C_{5-7}$carbocycle when $R^5$ is selected from H and methyl, or $R^4$ and $R^5$ together form a carbocycle of the partial formula —$(CR^aR^b)_n$— wherein $R^a$ and $R^b$ are independently selected from hydrogen and lower alkyl and n is selected from 2, 3, 4, 5 and 6;

$R^6$ is selected from hydrogen and lower alkyl;

$R^7$ is sec-butyl or iso-butyl;

$R^8$ is selected from hydrogen and lower alkyl; and $R^9$ is selected from

3

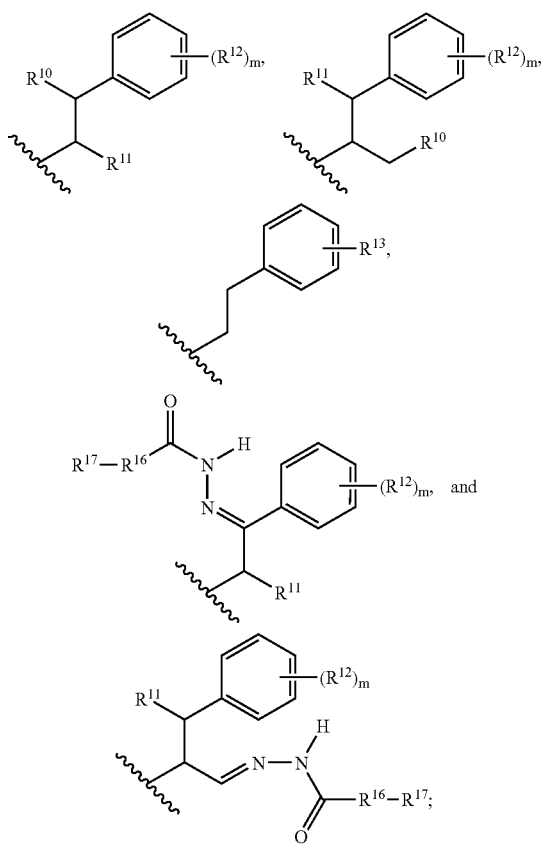

$R^{10}$ is selected from

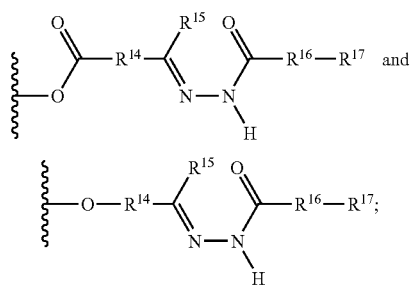

$R^{11}$ is selected from hydrogen and lower alkyl;

$R^{12}$ is selected from lower alkyl, halogen, and methoxy, and m is 0–5 where $R^{12}$ is independently selected at each occurrence;

4

$R^{13}$ is

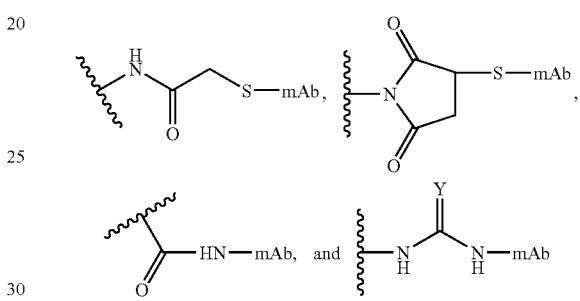

$R^{14}$ is selected from a direct bond, arylene (lower alkylene), lower alkylene and arylene;

$R^{15}$ is selected from hydrogen, lower alkyl and aryl;

$R^{16}$ is selected from arylene (lower alkylene), lower alkylene, arylene, and —$(CH_2OCH_2)_pCH_2$— where p is 1–5; and $R^{17}$ is selected from where Y=O or S, In another aspect, the present invention provides a compound of the formula

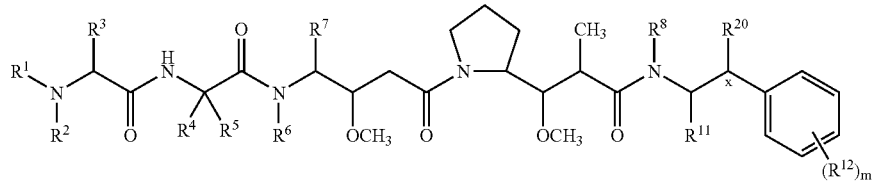

wherein, independently at each location:

$R^1$ is selected from hydrogen and lower alkyl;

$R^2$ is selected from hydrogen and lower alkyl;

$R^3$ is lower alkyl;

$R^4$ is selected from lower alkyl, aryl, and —$CH_2$-$C_{5-7}$ carbocycle when $R^5$ is selected from H and methyl, or $R^4$ and $R^5$ together form a carbocycle of the partial formula —$(CR^aR^b)_n$— wherein $R^a$ and $R^b$ are independently selected from hydrogen and lower alkyl and n is selected from 2, 3, 4, 5 and 6;

$R^6$ is selected from hydrogen and lower alkyl;

$R^7$ is sec-butyl or iso-butyl;

$R^8$ is selected from hydrogen and lower alkyl;

$R^{11}$ is selected from hydrogen and lower alkyl;

$R^{12}$ is selected from lower alkyl, halogen, and methoxy, and m is 0–5 where $R^{12}$ is independently selected at each occurrence; and $R^{20}$ is a reactive linker group having a reactive site that allows $R^{20}$ to be reacted with a targeting moiety, where $R^{20}$ can be bonded to the carbon labeled "x" by either a single or double bond.

In another aspect, the present invention provides a compound of the formula

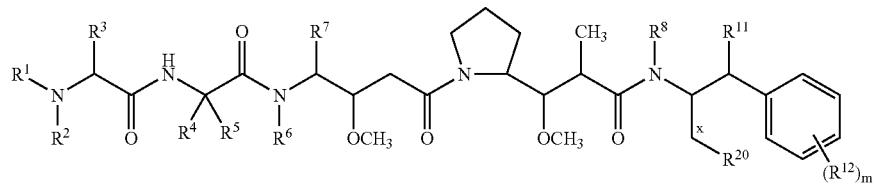

wherein, independently at each location:
$R^1$ is selected from hydrogen and lower alkyl;
$R^2$ is selected from hydrogen and lower alkyl;
$R^3$ is lower alkyl;
$R^4$ is selected from lower alkyl, aryl, and $-CH_2-C_{5-7}$ carbocycle when $R^5$ is selected from H and methyl, or $R^4$ and $R^5$ together form a carbocycle of the partial formula $-(CR^aR^b)_n-$ wherein $R^a$ and $R^b$ are independently selected from hydrogen and lower alkyl and n is selected from 2, 3, 4, 5 and 6;
$R^6$ is selected from hydrogen and lower alkyl;
$R^7$ is sec-butyl or iso-butyl;
$R^8$ is selected from hydrogen and lower alkyl;
$R^{11}$ is selected from hydrogen and lower alkyl;
$R^{12}$ is selected from lower alkyl, halogen, and methoxy, and m is 0–5 where $R^{12}$ is independently selected at each occurrence; and
$R^{20}$ is a reactive linker group having a reactive site that allows $R^{20}$ to be reacted with a targeting moiety, where $R^{20}$ can be bonded to the carbon labeled "x" by either a single or double bond.

In another aspect, the present invention provides a compound of the formula wherein, independently at each location:
$R^1$ is selected from hydrogen and lower alkyl;
$R^2$ is selected from hydrogen and lower alkyl;
$R^3$ is lower alkyl;
$R^4$ is selected from lower alkyl, aryl, and $-CH_2-C_{5-7}$ carbocycle when $R^5$ is selected from H and methyl, or $R^4$ and $R^5$ together form a carbocycle of the partial formula $-(CR^aR^b)_n-$ wherein $R^a$ and $R^b$ are independently selected from hydrogen and lower alkyl and n is selected from 2, 3, 4, 5 and 6;
$R^6$ is selected from hydrogen and lower alkyl;
$R^7$ is sec-butyl or iso-butyl;
$R^8$ is selected from hydrogen and lower alkyl; and
$R^{20}$ is a reactive linker group comprising a reactive site that allows $R^{20}$ to be reacted with a targeting moiety.

In another aspect, the present invention provides a compound of the formula

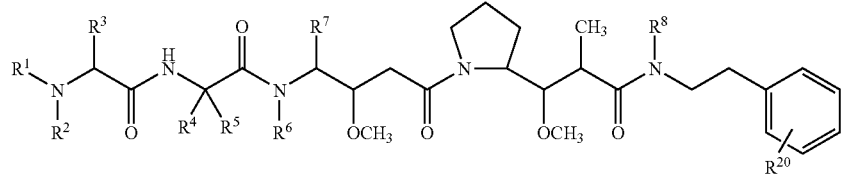

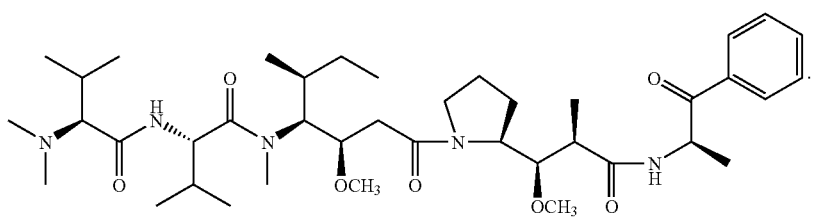

In another aspect, the present invention provides a compound of the formula

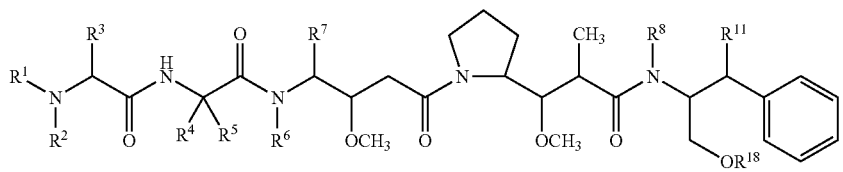

wherein, independently at each location:
$R^1$ is selected from hydrogen and lower alkyl;
$R^2$ is selected from hydrogen and lower alkyl;
$R^3$ is lower alkyl;
$R^4$ is selected from lower alkyl, aryl, and —$CH_2$—$C_{5-7}$ carbocycle when $R^5$ is selected from H and methyl, or $R^4$ and $R^5$ together form a carbocycle of the partial formula —$(CR^aR^b)_n$— wherein $R^a$ and $R^b$ are independently selected from hydrogen and lower alkyl and n is selected from 2, 3, 4, 5 and 6;
$R^6$ is selected from hydrogen and lower alkyl;
$R^7$ is sec-butyl or iso-butyl;
$R^8$ is selected from hydrogen and lower alkyl;
$R^{11}$ is selected from hydrogen and lower alkyl; and
$R^{18}$ is selected from hydrogen, a hydroxyl protecting group, and a direct bond where $OR^{18}$ represents =O.

In another aspect, the present invention provides a compound of the formula

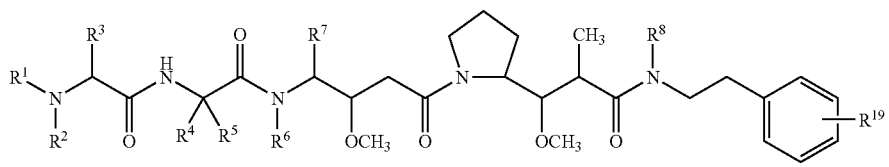

wherein, independently at each location:
$R^1$ is selected from hydrogen and lower alkyl;
$R^2$ is selected from hydrogen and lower alkyl;
$R^3$ is lower alkyl;
$R^4$ is selected from lower alkyl, aryl, and —$CH_2$—$C_{5-7}$ carbocycle when $R^5$ is selected from H and methyl, or $R^4$ and $R^5$ together form a carbocycle of the partial formula —$(CR^aR^b)_n$— wherein $R^a$ and $R^b$ are independently selected from hydrogen and lower alkyl and n is selected from 2, 3, 4, 5 and 6;
$R^6$ is selected from hydrogen and lower alkyl;
$R^7$ is sec-butyl or iso-butyl;
$R^8$ is selected from hydrogen and lower alkyl; and
$R^{19}$ is selected from hydroxy- and oxo-substituted lower alkyl.

In another aspect, the present invention provides a compound of the formula

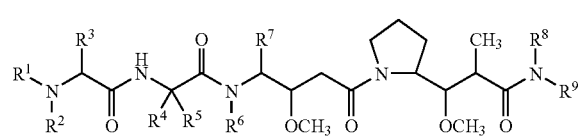

wherein, independently at each location:
$R^1$ is selected from hydrogen and lower alkyl;
$R^2$ is selected from hydrogen and lower alkyl;
$R^3$ is lower alkyl;
$R^4$ is selected from lower alkyl, aryl, and —$CH_2$—$C_{5-7}$ carbocycle when $R^5$ is selected from H and methyl, or $R^4$ and $R^5$ together form a carbocycle of the partial formula —$(CR^aR^b)_n$— wherein $R^a$ and $R^b$ are independently selected from hydrogen and lower alkyl and n is selected from 2, 3, 4, 5 and 6;
$R^6$ is selected from hydrogen and lower alkyl;
$R^7$ is sec-butyl or iso-butyl;
$R^8$ is selected from hydrogen and lower alkyl; and
$R^9$ is selected from

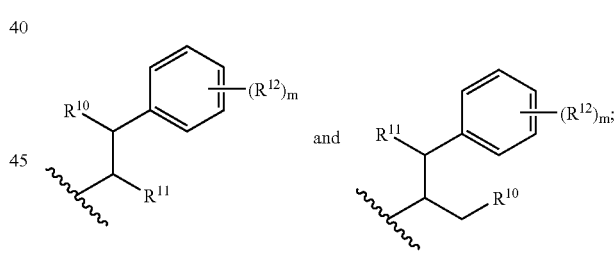

$R^{10}$ is selected from

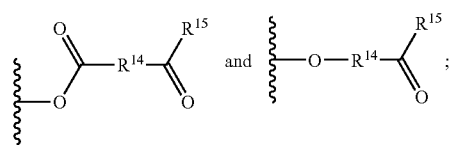

$R^{11}$ is selected from hydrogen and lower alkyl;
$R^{12}$ is selected from lower alkyl, halogen, and methoxy, and m is 0–5 where $R^{12}$ is independently selected at each occurrence;
$R^{14}$ is selected from a direct bond, arylene (lower alkylene), lower alkylene and arylene; and
$R^{15}$ is selected from hydrogen, lower alkyl and aryl.

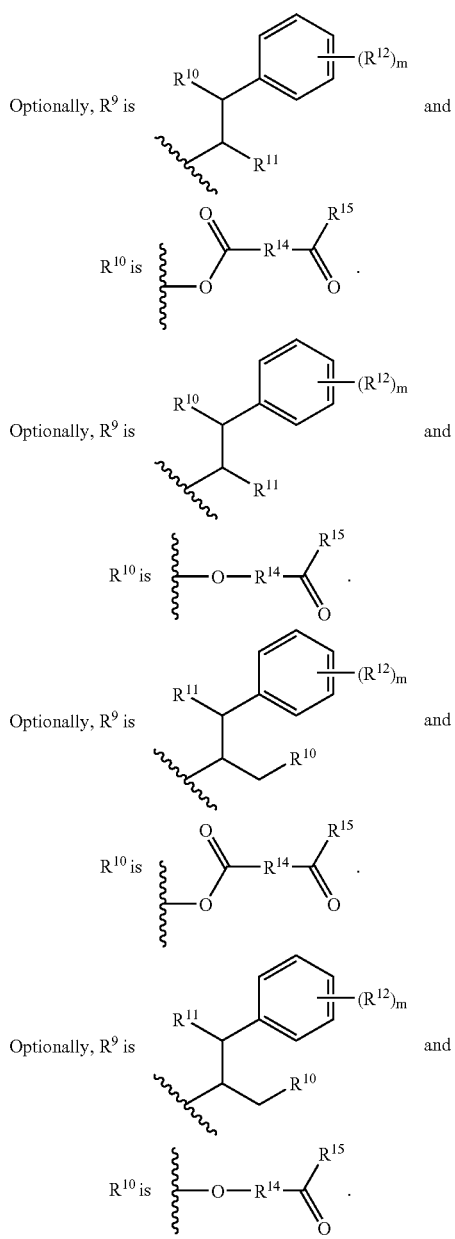

In another aspect, the present invention provides a composition comprising a biologically active compound as described above and a pharmaceutically acceptable carrier, diluent or excipient.

In another aspect, the present invention provides a method for killing a cell, the method comprising administering to the cell a lethal amount of a compound or composition as described above.

In another aspect, the present invention provides a method of killing a cell comprising a. delivering a compound or composition as described above to a cell, where the compound enters the cell;

b. cleaving mAb from the remainder of the compound; and c. killing the cell with the remainder of the compound.

In another aspect, the present invention provides a method of killing or inhibiting the multiplication of tumor cells or cancer cells in a human or other animal, the method comprising administering to the human or animal a therapeutically effective amount of a compound or composition described above.

These and related aspects of the present invention are described in more detail below.

DETAILED DESCRIPTION OF THE INVENTION

Figure 1:
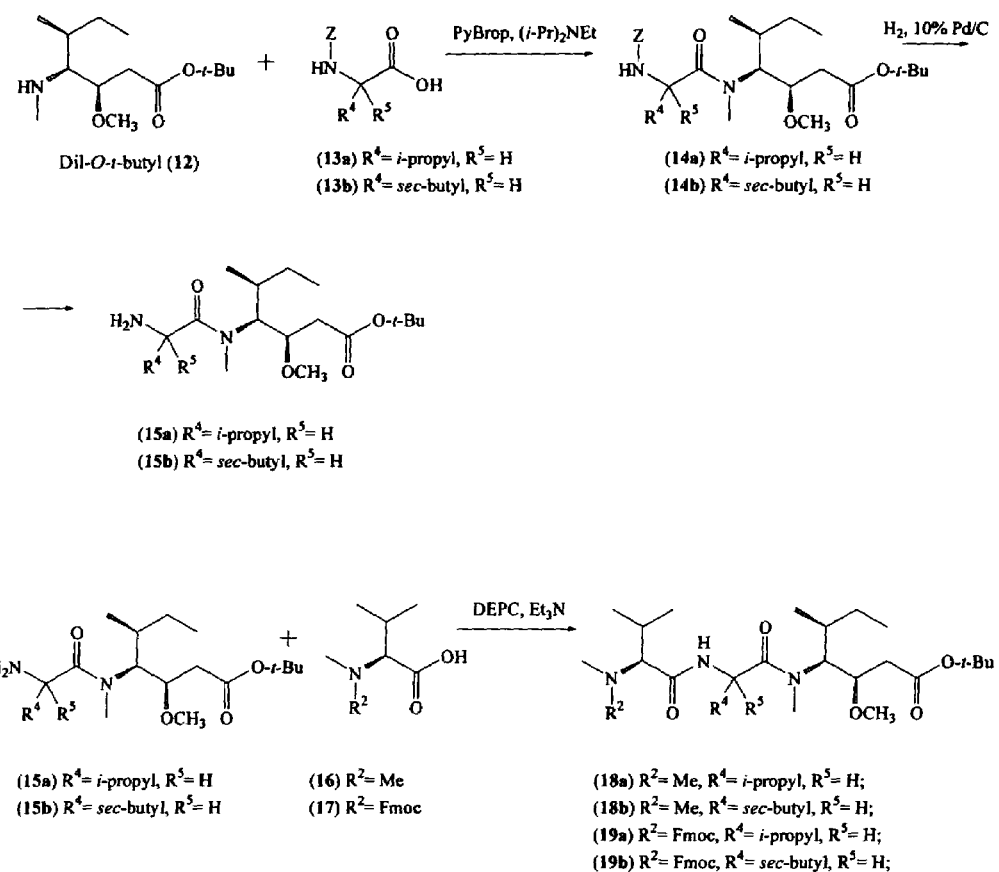
FIG. 1 shows a synthetic scheme illustrating the preparation of specific tripeptides useful in preparing compounds of the present invention.

Among other aspects, the present invention provides short peptide-containing compounds having biological activity, e.g., cytotoxicity, and methods for their use, e.g., in cancer therapy. Before describing the compounds of the present invention, reference is made to the following definitions that are used herein.

Definitions

As used herein the following terms have the indicated meanings:

"Animal subjects" include humans, monkeys, pigs, goats, cows, horses, dogs, and cats. Birds, including fowl, are also a suitable animal subject.

"Aryl" refers to aromatic groups which have at least one ring having a conjugated pi electron system and includes carbocyclic aryl and heterocyclic aryl. In specific aspects of the invention, the aryl group (and the arylene group as discussed below) has 5–14, or 6–12, or 6–10 atoms as part of one or more aromatic rings. In one aspect the aryl or arylene is a carbocyclic. "Carbocyclic aryl" refers to aromatic groups wherein the ring atoms of the aromatic ring are all carbon atoms. Carbocyclic aryl groups include monocyclic carbocyclic aryl groups and polycyclic groups, all of which may be optionally substituted. Exemplary carbocyclic aryl groups include phenyl and naphthyl. Exemplary substituted carbocyclic aryl groups include indene and phenyl substituted by one or two substituents such as, or selected from, lower alkyl, hydroxy, lower alkoxy, lower alkoxycarbonyl, halogen, trifluoromethyl, nitro, and cyano. "Heterocyclic aryl", which may also be called "heteroaryl" refers to aryl groups having from 1 to 9 carbon atoms and the remainder of the atoms are heteroatoms, and includes those heterocyclic systems described in "Handbook of Chemistry and Physics," 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroatoms include oxygen, nitrogen, and $S(O)_i$, wherein i is 0, 1 or 2. Suitable examples of heteroaryl groups include, without limitation, benzofuran, benzothiophene, indole, benzopyrazole, coumarin, isoquinoline, pyrrole, thiophene, furan, thiazole, imidazole, pyrazole, triazole, quinoline, pyrimidine, pyridine, pyridone, pyrazine, pyridazine, isothiazole, isoxazole and tetrazole. "Aryl groups" are bonded to one other group, while "arylene" refers to an aryl group that is bonded to two other groups. For example, phenyl

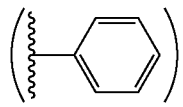

is an aryl group, while phenylene

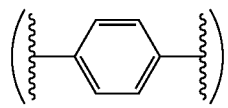

is one example of an arylene group.

"Arylene (lower alkylene)" refers to a group formed from an arylene group and an alkylene group, that together link two other groups. For example, in X-arylene (lower alkylene)-Y the arylenealkylene group links X and Y, and is formed from a lower alkylene, e.g., methylene (—CH$_2$—) and an arylene (e.g., 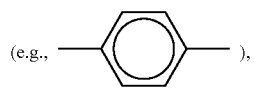 ), to provide the aryl (lower alkylene), e.g.,

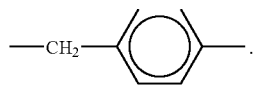

"Carbocycle" or "carbocyclic ring" refers to any saturated, unsaturated or aromatic monocyclic ring where the ring atoms are carbon. A $C_{5-7}$carbocycle refers to any carbocyclic ring having 5, 6 or 7 carbon atoms that form the ring. Examples of such carbocycles include, but are not limited to, cyclopentyl, cyclohexyl, cyclohexenyl, cyclohexadienyl, cycloheptyl, and phenyl.

"Compound", as in the terms "compound of the formula", "compound of the structure", "compound of the invention", and the like, shall refer to and encompass the chemical compound itself as well as, whether explicitly stated or not, and unless the context makes clear that the following are to be excluded: amorphous and crystalline forms of the compound, including polymorphic forms, where these forms may be part of a mixture or in isolation; free acid and free base forms of the compound, which are typically the forms shown in the structures provided herein; isomers of the compound, which refers to optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in admixture with one or more other isomers; isotopes of the compound, including deuterium- and tritium-containing compounds, and including compounds containing radioisotopes, including therapeutically- and diagnostically-effective radioisotopes; multimeric forms of the compound, including dimeric, trimeric, etc. forms; salts of the compound, preferably pharmaceutically acceptable salts, including acid addition salts and base addition salts, including salts having organic counterions and inorganic counterions, and including zwitterionic forms, where if a compound is associated with two or more counterions, the two or more counterions may be the same or different; and solvates of the compound, including hemisolvates, monosolvates, disolvates, etc., including organic solvates and inorganic solvates, said inorganic solvates including hydrates; where if a compound is associated with two or more solvent molecules, the two or more solvent molecules may be the same or different. In some instances, reference made herein to a compound of the invention will include an explicit reference to one or of the above forms, e.g., salts and solvates, however, this reference is for emphasis only, and is not to be construed as excluding other of the above forms as identified above.

"Direct bond" refers to a pair of electrons that hold together two adjacent atoms. Thus, when two atoms are separated by a direct bond, those two atoms are bonded together by a covalent bond. If a direct bond is attached to only one atom (X) and X is bonded to an adjacent atom (Y), then the direct bond represents a second bond between X and Y, i.e., the direct bond option provides a double bond between X and Y, at the expense of a hydrogen that would otherwise be bonded to Y. For example C—O—R where R is a direct bond denotes C=O.

"Independently at each location" and "independently at each occurrence" are synonymous terms which mean that any selection is independent of any other selection. For instance, if a variable is selected from two options, and the variable occurs twice, then the option selected at one occurrence of the variable does not impact in any way the choice of the option selected at the second occurrence of the variable.

"Leaving group" refers to a functional group that can be readily substituted by another functional group. A preferred leaving group is replaced by $S_N2$ displacement by a nucleophile. Such leaving groups are well known in the art, and include halides (e.g., chloride, bromide, iodide), mesylate, tosylate, etc.

"Lower alkyl" refers to a straight or a branched chain, cyclic or acyclic, monovalent saturated hydrocarbon, halocarbon or hydrohalocarbon radical of one to ten carbon atoms. In various aspects, the lower alkyl group has 1–8, 1–6, 1–5, or 1–4 carbons. Thus, the alkyl group may optionally have halogen substitution, where a halocarbon contains only carbon and halogen, and where a hydrohalocarbon contains carbon, halogen and hydrogen. Exemplary lower alkyl groups are, without limitation, methyl, ethyl, propyl, iso-propyl, n-butyl, iso-butyl, sec-butyl, tert-butyl, n-pentyl, n-hexyl, and cyclohexyl. "Lower alkylene" refers to a lower alkyl group that is bonded to two groups. For example, methyl (—$CH_3$) is a lower alkyl group, while methylene (—$CH_2$—) is a lower alkylene group. A hydroxy- or oxo-substituted lower alkyl refers to a lower alkyl group wherein a hydrogen on the lower alkyl group is replaced by —OH (for a hydroxy-substituted lower alkyl), or two hydrogens on a single carbon of the lower alkyl group are replaced by =O (for an oxo-substituted lower alkyl).

"mAb" refers to monoclonal antibody. Monoclonal antibodies are homogeneous with respect to immunoglobulin heavy and light chains. Such antibodies are well known in the art. See, e.g., Harlow et al., Antibodies: A Laboratory Manual, Cold Spring Harbor Laboratory (1988). Monoclonal antibodies include chimeric antibodies, where a chimeric antibody has at least one constant region domain derived from a first mammalian species and at least one variable region domain derived from a second, distinct mammalian species. See, e.g., Morrison et al., 1984, *Proc. Natl. Acad. Sci. USA*, 81:6851–55. The chimeric antibody may be, for example, a humanized chimeric antibody. See, e.g., Jones et al., 1986 *Nature* 321:522–25; Riechmann et al., 1988 *Nature* 332:323–27; and Bajorath et al., 1995 *Ther. Immunol.* 2:95–103; EP-0578515-A3. The monoclonal antibody may be constructed as single chain Fv polypeptide fragments (single chain antibodies). See, e.g., Bird et al., 1988 *Science* 242:423–426; Huston et al., 1988 *Proc. Natl. Acad. Sci. USA* 85:5879–5883.

"Pharmaceutically acceptable salt" and "salts thereof" refers to organic or inorganic salts of the pharmaceutically important molecule. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically important organic molecule may have more than one charged atom in its structure. Situations where multiple charged atoms are part of the molecule may have multiple counterions. Hence, the molecule of a pharmaceutically acceptable salt may contain one or more than one charged atoms and may also contain, one or more than one counterion. The desired charge distribution is determined according to methods of drug administration. Examples of pharmaceutically acceptable salts are well known in the art but, without limiting the scope of the present invention, exemplary presentations can be found in the Physician's Desk Reference, The Merck Index, The Pharmacopoeia and Goodman & Gilman's The Pharmacological Basis of Therapeutics. The salt will typically be either an acid addition salt, i.e., a salt formed by adding an acid to a pentapeptide compound, or a base addition salt, i.e., a salt formed by adding a base to a pentapeptide compound. The pentapeptide compounds of the invention contain at least one amine group, and accordingly acid addition salts may be formed with this amine group, where acid addition salts refer to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable solvate" refers to a solvate that retains the biological effectiveness and properties of the biologically active pentapeptide compound of the invention. Examples of pharmaceutically acceptable solvates include, but are not limited to, water, isopropanol, ethanol, methanol, DMSO, ethyl acetate, acetic acid, and ethanolamine. It will be appreciated by those skilled in the art that solvated forms are biologically equivalent to unsolvated forms and are intended to be encompassed within the scope of the present invention. Sykes, P. A., Guidebook to Mechanism in Organic Chemistry, 6th Ed (1986, John Wiley & Sons, N.Y.) is an exemplary reference that describe solvates.

The following abbreviations may be used herein and have the indicated definitions: t-Boc is tert-butoxy carbonyl, DCC is dicyclohexylcarbodiimide, DIAD is diisopropylazodicarboxylate; Fmoc is 9-fluorenylmethoxycarbonyl, DEPC is diethyl phosphorocyanidate, DMAP is 4-(N,N-dimethylamino) pyridine, PyBrop is bromo-tris-pyrrolidino-phosphonium hexafluorophosphate, TEAA is triethylammonium acetate, TFA is trifluoroacetic acid, and Z is benzyloxycarbonyl.

In the phrase "$R^{20}$ is a reactive linker having a reactive site that allows $R^{20}$ to be reacted with a targeting moiety", a "reactive site" refers to a functional moiety that can undergo reaction with a ligand so as to provide a covalent bond between the ligand and the reactive linker. In one aspect of the invention, the reactive site is reactive with a functional group selected from thiol and amino. Both thiol and amino groups are present in proteins, where thiol groups are, e.g., produced by reduction of disulfide bonds in proteins, and amino groups are present in, e.g., a lysine moiety of a protein.

In a preferred aspect of the invention, the reactive linker has a reactive site that is reactive with a thiol group. For instance, the reactive site may be a maleimide of the formula

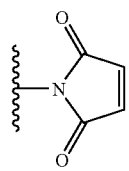

where the carbon-carbon double bond is reactive with nucleophiles, e.g., thiol groups. Alternatively, the reactive site may have the formulae

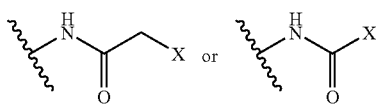

where X is a leaving group that may be displaced by a nucleophile, e.g., a thiol group as found on a protein.

In another preferred aspect of the invention, the reactive linker contains a reactive site that is reactive with an amine or amino group. Suitable amine reactive sites include, without limitation, activated esters such as N-hydroxysuccinimide esters, p-nitrophenyl esters, pentafluorophenyl esters, and other reactive functionalities, such as isothiocyanates, isocyanates, anhydrides, acid chlorides, and sulfonyl chlorides. Each of these functionalities provides a reactive site for a reactive linker of the present invention.

Compounds

In one aspect, the present invention provides compounds of the general structure "drug-linker-targeting agent", where the drug is a pentapeptide as disclosed herein and the targeting agent is a monoclonal antibody (mAb). Such compounds have the following structure, and may also be referred to herein as prodrugs.

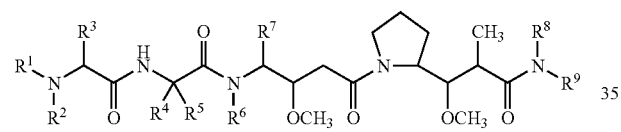

In this structure, independently at each location: $R^1$ is selected from hydrogen and lower alkyl; $R^2$ is selected from hydrogen and lower alkyl; $R^3$ is lower alkyl; $R^4$ is selected from lower alkyl, aryl, and —$CH_2$—$C_{5\text{-}7}$carbocycle when $R^5$ is selected from H and methyl, or $R^4$ and $R^5$ together form a carbocycle of the partial formula —$(CR^aR^b)_n$— wherein $R^a$ and $R^b$ are independently selected from hydrogen and lower alkyl and n is selected from 2, 3, 4, 5 and 6; $R^6$ is selected from hydrogen and lower alkyl; $R^7$ is sec-butyl or iso-butyl; $R^8$ is selected from hydrogen and lower alkyl; and $R^9$ is selected from

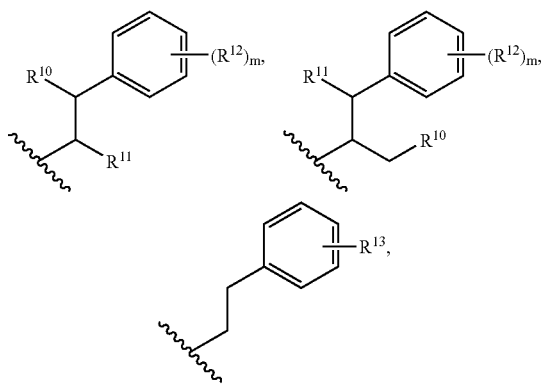

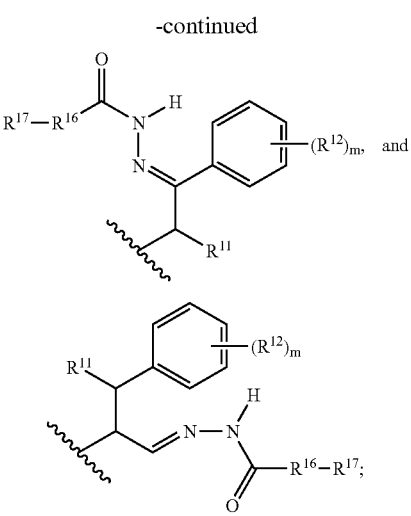

wherein $R^{10}$ is selected from

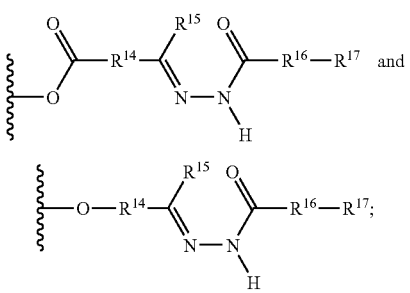

$R^{11}$ is selected from hydrogen and lower alkyl; $R^{12}$ is selected from lower alkyl, halogen, and methoxy, and m is 0–5 where $R^{12}$ is independently selected at each occurrence; and $R^{13}$ is

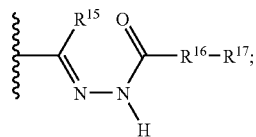

wherein: $R^{14}$ is selected from a direct bond, arylene (lower alkylene), lower alkylene and arylene; $R^{15}$ is selected from hydrogen, lower alkyl and aryl; $R^{16}$ is selected from arylene (lower alkylene), lower alkylene, arylene, and —$(CH_2OCH_2)_pCH_2$— where p is 1–5; and $R^{17}$ is selected

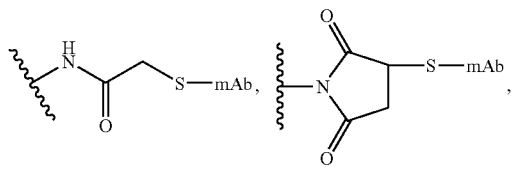

-continued

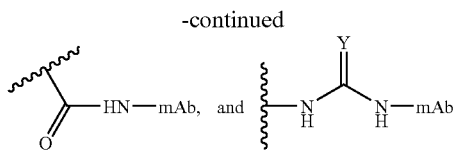

where Y=O or S.

In optional embodiments of the invention: $R^1$ is hydrogen; $R^1$ and $R^2$ are methyl; $R^3$ is isopropyl; $R^4$ is selected from lower alkyl, aryl, and —$CH_2$—$C_{5-7}$carbocycle and $R^5$ is selected from H and methyl; $R^4$ is selected from lower alkyl, and $R^5$ is selected from H and methyl; $R^4$ and $R^5$ together form a carbocycle of the partial formula —$(CR^aR^b)_n$— wherein $R^a$ and $R^b$ are independently selected from hydrogen and lower alkyl and n is selected from 2, 3, 4, 5 and 6; $R^6$ is lower alkyl; $R^8$ is hydrogen.

In another optional embodiment, $R^9$ is

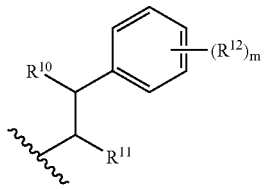

and $R^{10}$ is selected from

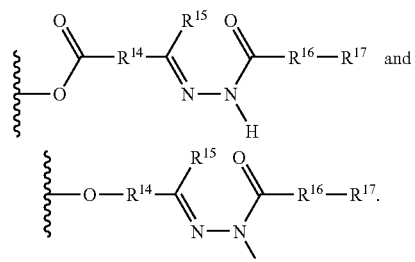

In one embodiment $R^{10}$ is

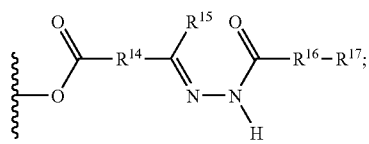

while in another embodiment $R^{10}$ is

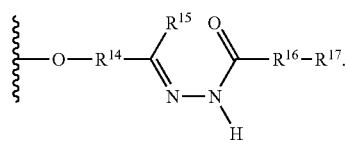

In a preferred embodiment, $R^{14}$ is selected from arylene and lower alkylene; $R^{15}$ is selected from lower alkyl and aryl; and $R^{16}$ is lower alkylene.

In another optional embodiment, $R^9$ is

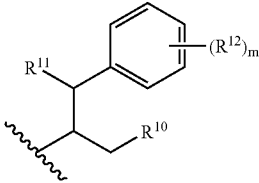

and $R^{10}$ is selected from

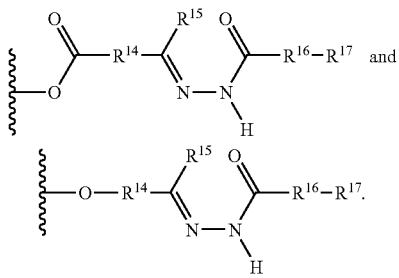

In a preferred embodiment, $R^{14}$ is selected from arylene and lower alkylene; $R^{15}$ is selected from lower alkyl and aryl; and $R^{16}$ is lower alkylene.

In another optional embodiment, $R^9$ is

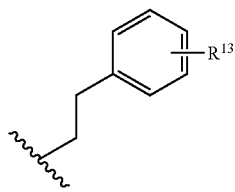

and $R^{13}$ is

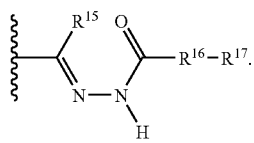

In a preferred embodiment, $R^{15}$ is lower alkyl; and $R^{16}$ is lower alkylene.

In another optional embodiment, $R^9$ is

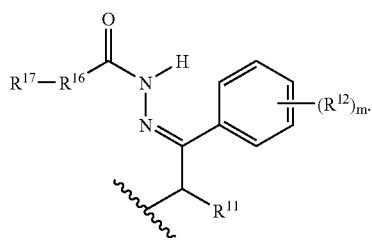

In a preferred embodiment, $R^{16}$ is lower alkylene.
In another optional embodiment, $R^9$ is

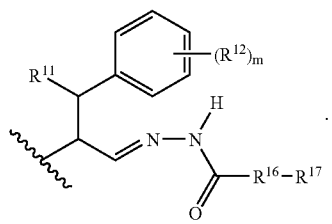

In a preferred embodiment, $R^{16}$ is selected from lower alkylene and arylene.
In one embodiment $R^{17}$ is

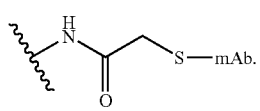

In another embodiment, $R^{17}$ is

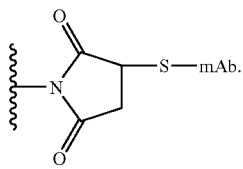

In another embodiment, $R^{17}$ is

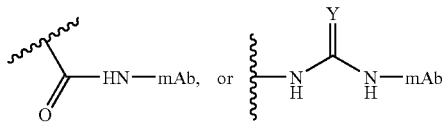

where Y=O or S.
For example, the present invention provides a prodrug of the formula

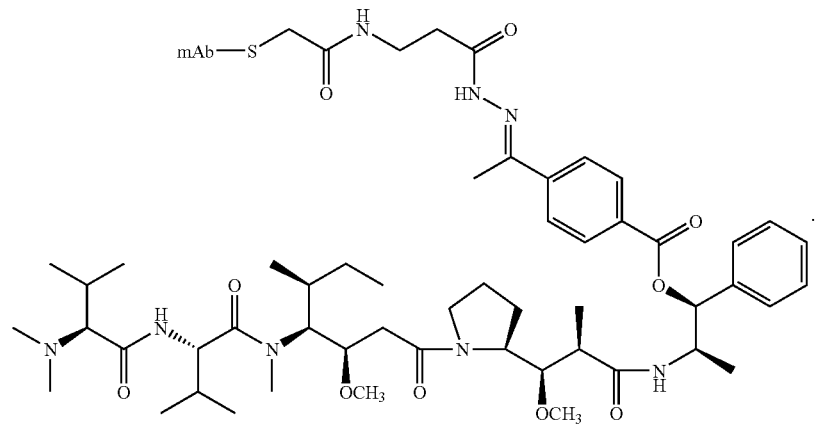

In addition, the present invention provides a prodrug of the formula:

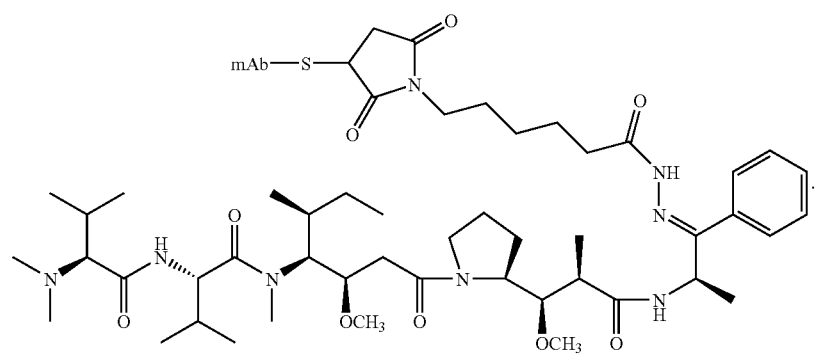

In addition, the present invention provides a prodrug of the formula:

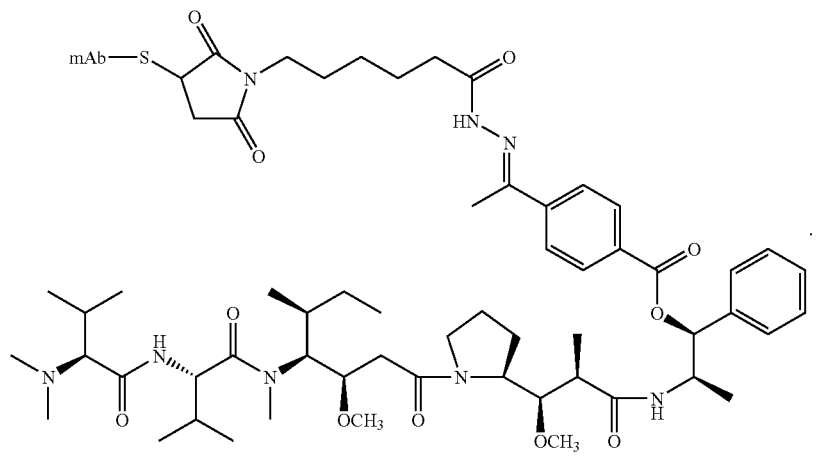

In addition to prodrugs as described above, the present invention also provides intermediate compounds that can be used to prepare prodrugs. These intermediate compounds contain a reactive linker group $R^{20}$ having a reactive site that allows $R^{20}$ to be reacted with a targeting moiety, e.g., an mAb.

In one aspect, the invention provides intermediate compounds of the formula

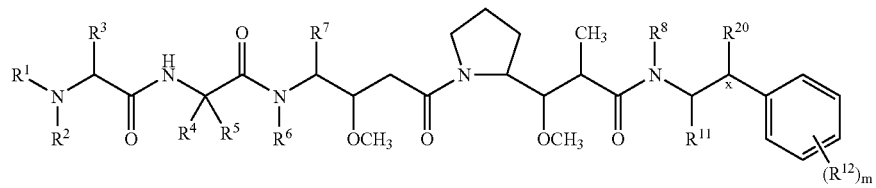

wherein, independently at each location: $R^1$ is selected from hydrogen and lower alkyl; $R^2$ is selected from hydrogen and lower alkyl; $R^3$ is lower alkyl; $R^4$ is selected from lower alkyl, aryl, and —$CH_2$—$C_{5-7}$carbocycle when $R^5$ is selected from H and methyl, or $R^4$ and $R^5$ together form a carbocycle of the partial formula —$(CR^aR^b)_n$— wherein $R^a$ and $R^b$ are independently selected from hydrogen and lower alkyl and n is selected from 2, 3, 4, 5 and 6; $R^6$ is selected from hydrogen and lower alkyl; $R^7$ is sec-butyl or iso-butyl; $R^8$ is selected from hydrogen and lower alkyl; $R^{11}$ is selected from hydrogen and lower alkyl; $R^{12}$ is selected from lower alkyl, halogen, and methoxy, and m is 0–5 where $R^{12}$ is independently selected at each occurrence; and $R^{20}$ is a reactive linker group having a reactive site that allows $R^{20}$ to be reacted with a targeting moiety, where $R^{20}$ can be bonded to the carbon labeled "x" by either a single or double bond.

In another aspect, the present invention provides intermediate compounds of the formula

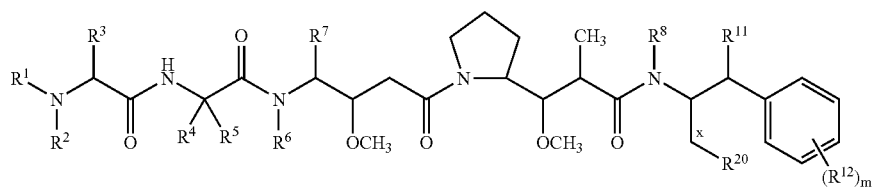

wherein, independently at each location: $R^1$ is selected from hydrogen and lower alkyl; $R^2$ is selected from hydrogen and lower alkyl; $R^3$ is lower alkyl; $R^4$ is selected from lower alkyl, aryl, and —$CH_2$—$C_{5-7}$carbocycle when $R^5$ is selected from H and methyl, or $R^4$ and $R^5$ together form a carbocycle of the partial formula —$(CR^aR^b)_n$— wherein $R^a$ and $R^b$ are independently selected from hydrogen and lower alkyl and n is selected from 2, 3, 4, 5 and 6; $R^6$ is selected from hydrogen and lower alkyl; $R^7$ is sec-butyl or iso-butyl; $R^8$ is selected from hydrogen and lower alkyl; $R^{11}$ is selected from hydrogen and lower alkyl; $R^{12}$ is selected from lower alkyl, halogen, and methoxy, and m is 0–5 where $R^{12}$ is independently selected at each occurrence; and $R^{20}$ is a reactive linker group having a reactive site that allows $R^{20}$ to be reacted with a targeting moiety, where $R^{20}$ can be bonded to the carbon labeled "x" by either a single or double bond.

In another aspect, the present invention provides intermediate compounds of the formula

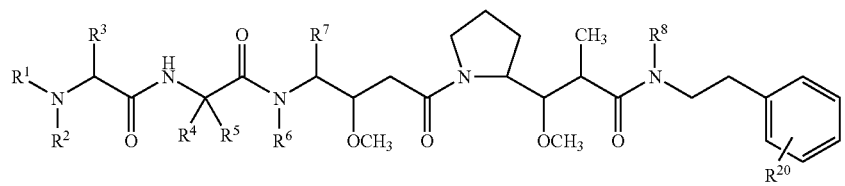

wherein, independently at each location: $R^1$ is selected from hydrogen and lower alkyl; $R^2$ is selected from hydrogen and lower alkyl; $R^3$ is lower alkyl; $R^4$ is selected from lower alkyl, aryl, and —$CH_2$—$C_{5-7}$carbocycle when $R^5$ is selected from H and methyl, or $R^4$ and $R^5$ together form a carbocycle of the partial formula —$(CR^aR^b)_n$— wherein $R^a$ and $R^b$ are independently selected from hydrogen and lower alkyl and n is selected from 2, 3, 4, 5 and 6; $R^6$ is selected from hydrogen and lower alkyl; $R^7$ is sec-butyl or iso-butyl; $R^8$ is selected from hydrogen and lower alkyl; and $R^{20}$ is a reactive linker group comprising a reactive site that allows $R^{20}$ to be reacted with a targeting moiety.

In any of the foregoing intermediate compounds, in further aspects $R^{20}$ comprises a hydrazone of the formula

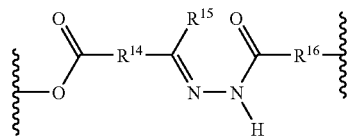

wherein: $R^{14}$ is selected from a direct bond, arylene (lower alkylene), lower alkylene and arylene; $R^{15}$ is selected from hydrogen, lower alkyl and aryl; and $R^{16}$ is selected from arylene (lower alkylene), lower alkylene, arylene, and —$(CH_2OCH_2)_pCH_2$— where p is 1–5.

Additionally, in any of the foregoing intermediate compounds, in further aspects $R^{20}$ comprises a hydrazone of the formula

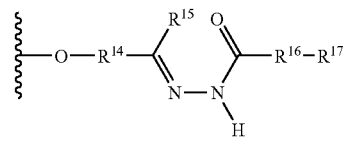

wherein: $R^{14}$ is selected from a direct bond, arylene (lower alkylene), lower alkylene and arylene; $R^{15}$ is selected from hydrogen, lower alkyl, and aryl; and $R^{16}$ is selected from arylene (lower alkylene), lower alkylene, arylene, and —$(CH_2OCH_2)_pCH_2$— where p is 1–5.

Additionally, in any of the foregoing intermediate compounds, in further aspects $R^{20}$ comprises a hydrazone of the formula:

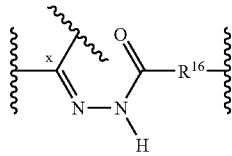

wherein: $R^{16}$ is selected from lower alkylene, arylene, and —$(CH_2OCH_2)_pCH_2$— where p is 1–5, and x identifies the carbon also marked x in the intermediate structures shown above.

As mentioned previously, a reactive linker group $R^{20}$ includes a reactive site that can be reacted with a targeting moiety so as to indirectly join the targeting moiety to the drug. The following are exemplary reactive sites that may be present as part of the $R^{20}$ group. For example, any of the following reactive sites may be joined to any of the hydrazone structures set forth above in order to form a complete $R^{20}$ structure. In one aspect, $R^{20}$ comprises a reactive site having the formula

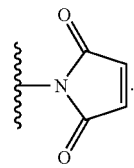

In another aspect, $R^{20}$ comprises a reactive site having the formula

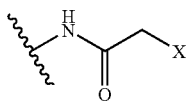

wherein X is a leaving group. In another aspect, $R^{20}$ comprises a reactive site having the formula

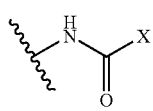

wherein X is a leaving group.

For example, the present invention provides intermediate compounds of the formulae:
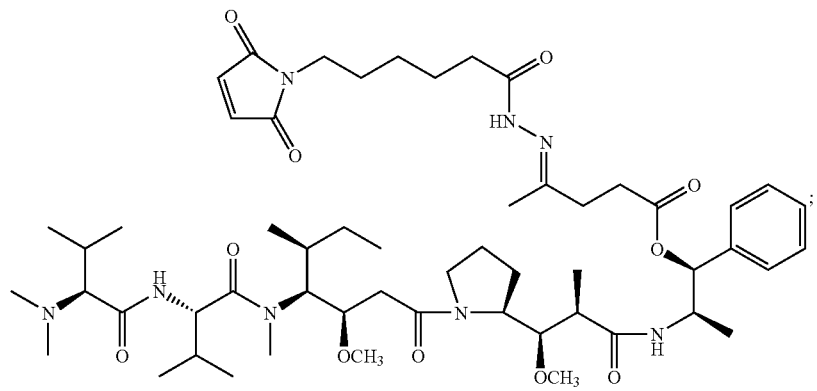
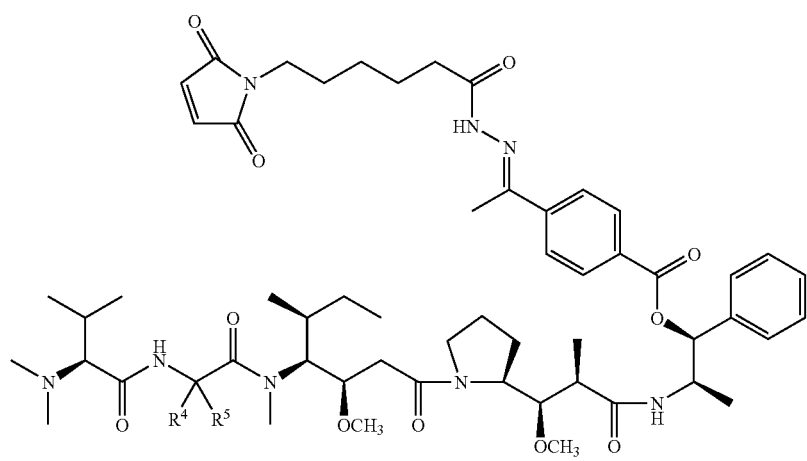
wherein $R^4$ is selected from iso-propyl and sec-butyl, and $R^5$ is hydrogen;
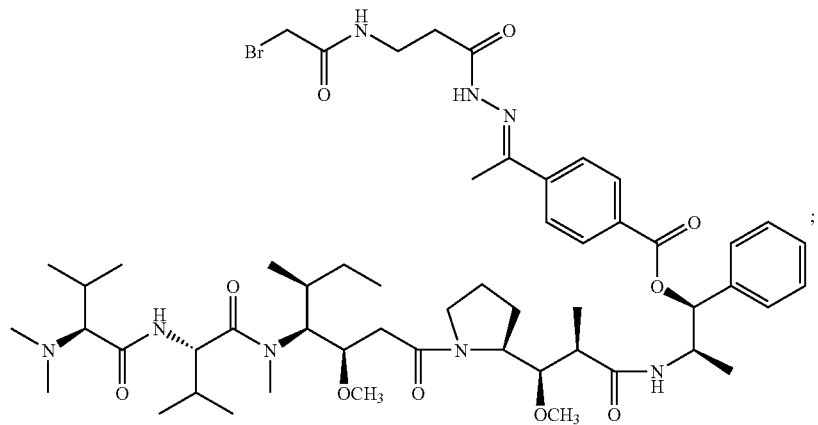

-continued

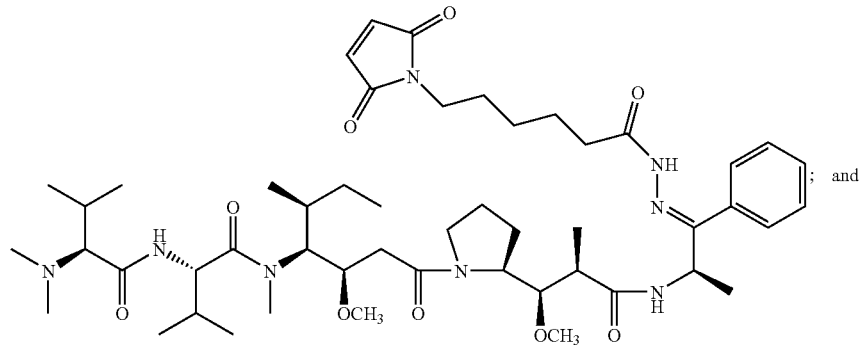

; and

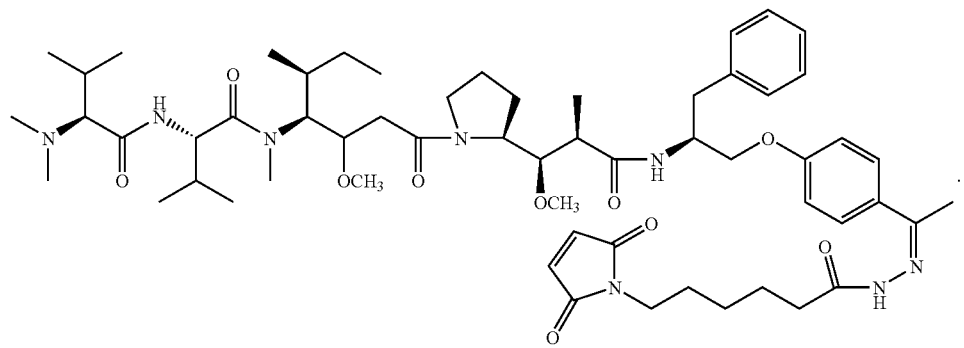

In addition to prodrugs as described above, and direct precursors thereto as described above and referred to as intermediate compounds, the present invention also provides precursors to the intermediate compounds. In one aspect of the invention, these precursors to the intermediate compounds have a carbonyl group. As discussed in more detail below, a carbonyl group is conveniently reacted with hydrazine derivatives in order to prepare intermediate compounds having $R^{20}$ groups and reactive sites as part of the $R^{20}$ groups. Thus, in a further aspect, the present invention provides the following precursors to the intermediate compounds, where these precursors have either carbonyl groups or hydroxyl groups that could be readily oxidized to a carbonyl group.

In one aspect, the present invention provides compounds of the formula

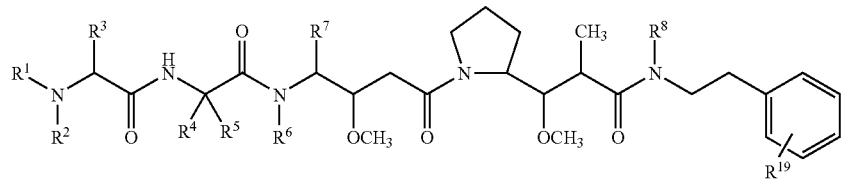

and pharmaceutically acceptable salts and solvates thereof wherein, independently at each location: $R^1$ is selected from hydrogen and lower alkyl; $R^2$ is selected from hydrogen and lower alkyl; $R^3$ is lower alkyl; $R^4$ is selected from lower alkyl, aryl, and —$CH_2$—$C_{5-7}$carbocycle when $R^5$ is selected from H and methyl, or $R^4$ and $R^5$ together form a carbocycle of the partial formula —$(CR^aR^b)_n$— wherein $R^a$ and $R^b$ are independently selected from hydrogen and lower alkyl and n is selected from 2, 3, 4, 5 and 6; $R^6$ is selected from hydrogen and lower alkyl; $R^7$ is sec-butyl or iso-butyl; $R^8$ is selected from hydrogen and lower alkyl; and $R^{19}$ is selected from hydroxy- and oxo-substituted lower alkyl. In various optional embodiments: $R^1$ is hydrogen; or $R^1$ and $R^2$ are methyl; and/or $R^3$ is iso-propyl; and/or $R^4$ is selected from lower alkyl, aryl, and —$CH_2$—$C_{5-7}$carbocycle and $R^5$ is selected from H and methyl; or $R^4$ is selected from lower alkyl, and $R^5$ is selected from H and methyl; or $R^4$ and $R^5$ together form a carbocycle of the partial formula —$(CR^a R^b)_n$— wherein $R^a$ and $R^b$ are independently selected from hydrogen and lower alkyl and n is selected from 2, 3, 4, 5 and 6; and/or $R^6$ is lower alkyl; and/or $R^8$ is hydrogen; and/or $R^{19}$ is oxo-substituted lower alkyl. An exemplary compound of this aspect of the invention is

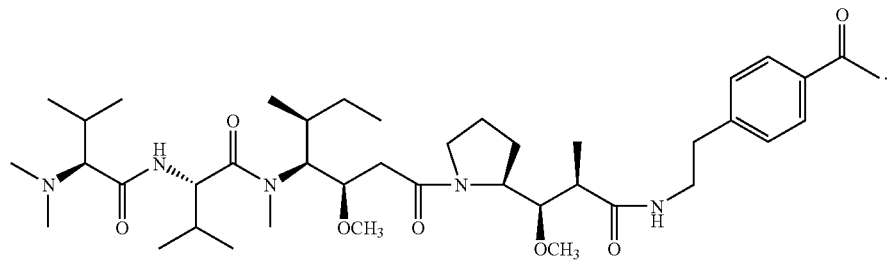

In another aspect the present invention provides compounds of the formula

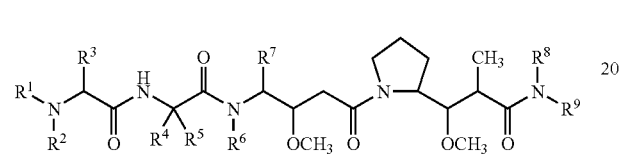

and pharmaceutically acceptable salts and solvates thereof wherein, independently at each location: $R^1$ is selected from hydrogen and lower alkyl; $R^2$ is selected from hydrogen and lower alkyl; $R^3$ is lower alkyl; $R^4$ is selected from lower alkyl, aryl, and —CH$_2$—C$_{5-7}$carbocycle when $R^5$ is selected from H and methyl, or $R^4$ and $R^5$ together form a carbocycle of the partial formula —(CR$^a$R$^b$)$_n$— wherein R$^a$ and R$^b$ are independently selected from hydrogen and lower alkyl and n is selected from 2, 3, 4, 5 and 6; $R^6$ is selected from hydrogen and lower alkyl; $R^7$ is sec-butyl or iso-butyl; $R^8$ is selected from hydrogen and lower alkyl; $R^9$ is selected from

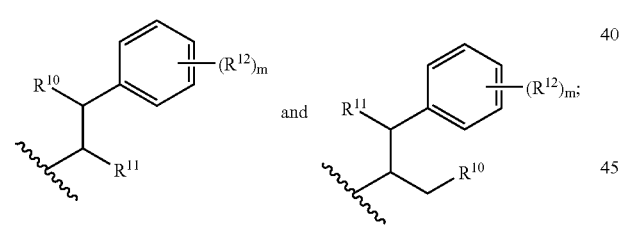

$R^{10}$ is selected from

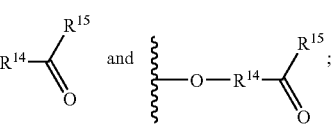

$R^{11}$ is selected from hydrogen and lower alkyl; $R^{12}$ is selected from lower alkyl, halogen, and methoxy, and m is 0–5 where $R^{12}$ is independently selected at each occurrence; $R^{14}$ is selected from a direct bond, arylene (lower alkylene), lower alkylene and arylene; and $R^{15}$ is selected from hydrogen, lower alkyl and aryl. In various embodiments of this aspect of the invention: $R^{10}$ is

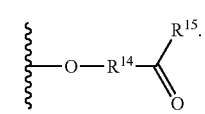

or $R^{10}$ is

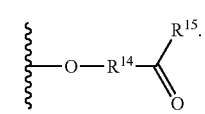

Some specific compounds of this aspect of the invention have the structures

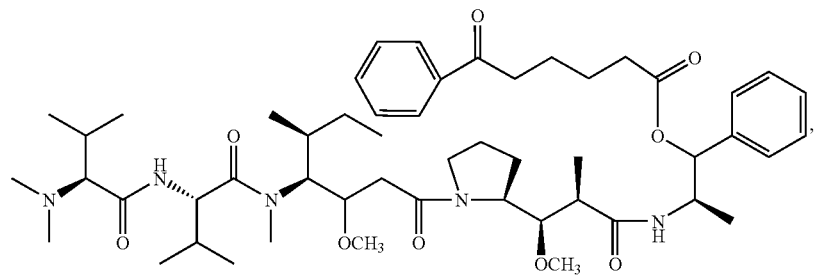

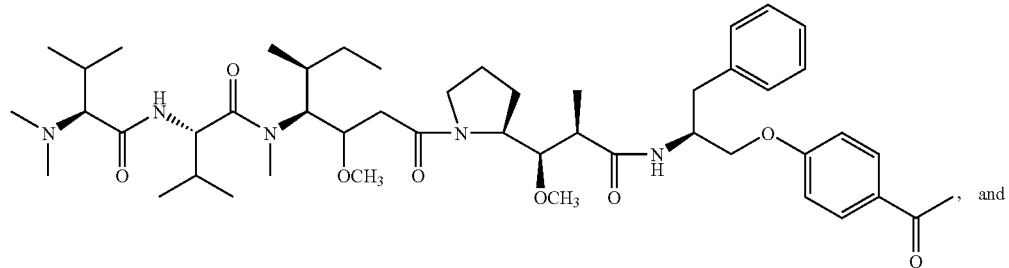

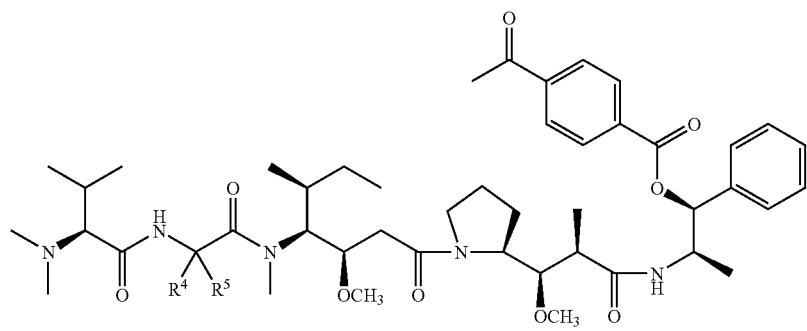

wherein R⁴ is iso-propyl or sec-butyl and R⁵ is hydrogen.

In a further aspect the present invention provides pentapeptide drugs of the following structures. In these structures the drug may contain a carbonyl group that could optionally be reacted directly with a hydrazine derivative or other reactive group so as to introduce an $R^{20}$ group into the molecule. Thus, in one embodiment, the present invention provides a pentapeptide drug of the formula $R^a$ and $R^b$ are independently selected from hydrogen and lower alkyl and n is selected from 2, 3, 4, 5 and 6; $R^6$ is selected from hydrogen and lower alkyl; $R^7$ is sec-butyl or iso-butyl; $R^8$ is selected from hydrogen and lower alkyl; $R^{11}$ is selected from hydrogen and lower alkyl; and $R^{18}$ is selected from hydrogen, a hydroxyl protecting group, and a direct bond where $OR^{18}$ represents =O. For instance, the present invention provides compound of the formula

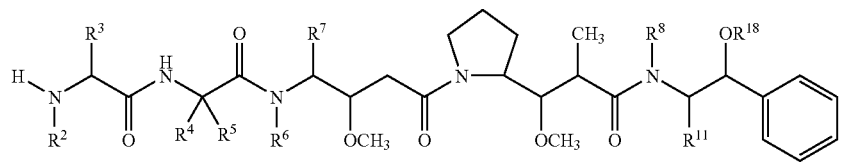

wherein, independently at each location: $R^2$ is selected from hydrogen and lower alkyl; $R^3$ is lower alkyl; $R^4$ is selected from lower alkyl, aryl, and —CH₂—C₅₋₇carbocycle when $R^5$ is selected from H and methyl, or $R^4$ and $R^5$ together form a carbocycle of the partial formula —(CR$^a$R$^b$)$_n$— wherein

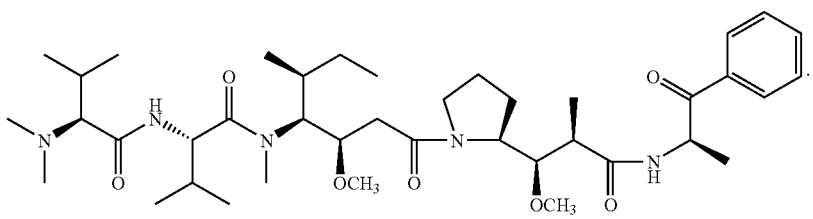

In another embodiment, the present invention provides a pentapeptide drug of the formula

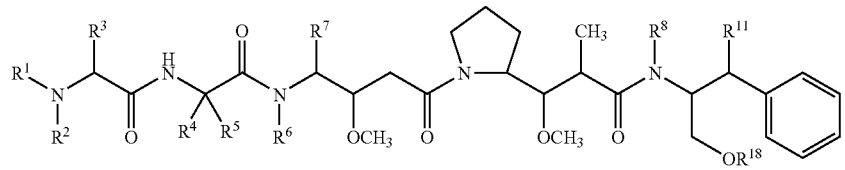

wherein, independently at each location: $R^1$ is selected from hydrogen and lower alkyl; $R^2$ is selected from hydrogen and lower alkyl; $R^3$ is lower alkyl; $R^4$ is selected from lower alkyl, aryl, and —$CH_2$—$C_{5-7}$carbocycle when $R^5$ is selected from H and methyl, or $R^4$ and $R^5$ together form a carbocycle of the partial formula —$(CR^aR^b)_n$— wherein $R^a$ and $R^b$ are independently selected from hydrogen and lower alkyl and n is selected from 2, 3, 4, 5 and 6; $R^6$ is selected from hydrogen and lower alkyl; $R^7$ is sec-butyl or iso-butyl; $R^8$ is selected from hydrogen and lower alkyl; $R^{11}$ is selected from hydrogen and lower alkyl; and $R^{18}$ is selected from hydrogen, a hydroxyl protecting group, and a direct bond where $OR^{18}$ represents =O. For instance, the present invention provides compounds of the formulae wherein, independently at each location: $R^1$ is selected from hydrogen and lower alkyl; $R^2$ is selected from hydrogen and lower alkyl; $R^3$ is lower alkyl; $R^4$ is selected from lower alkyl, aryl, and —$CH_2$—$C_{5-7}$carbocycle when $R^5$ is selected from H and methyl, or $R^4$ and $R^5$ together form a carbocycle of the partial formula —$(CR^aR^b)_n$— wherein $R^a$ and $R^b$ are independently selected from hydrogen and lower alkyl and n is selected from 2, 3, 4, 5 and 6; $R^6$ is selected from hydrogen and lower alkyl; $R^7$ is sec-butyl or iso-butyl; $R^8$ is selected from hydrogen and lower alkyl; and $R^{19}$ is selected from hydroxy- and oxo-substituted lower alkyl. For instance, the present invention provides a compound of the formula

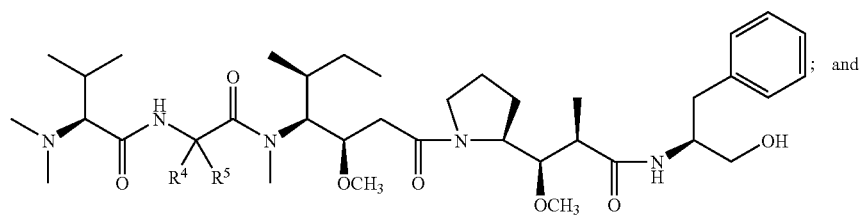

; and

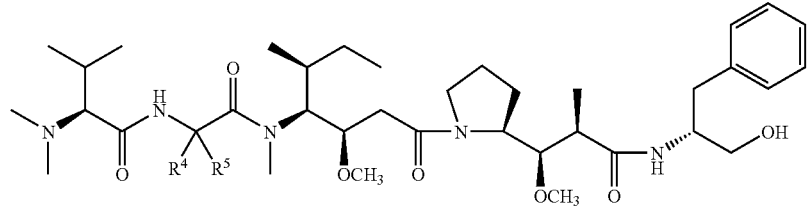

wherein $R^4$ iso-propyl and $R^5$ is hydrogen.

In another embodiment, the present invention provides a pentapeptide drug of the formula

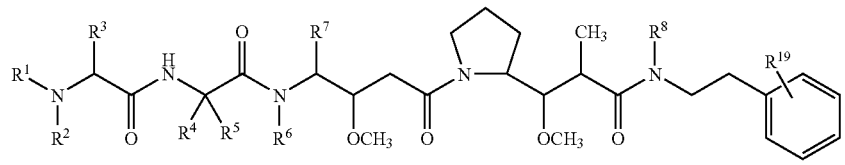

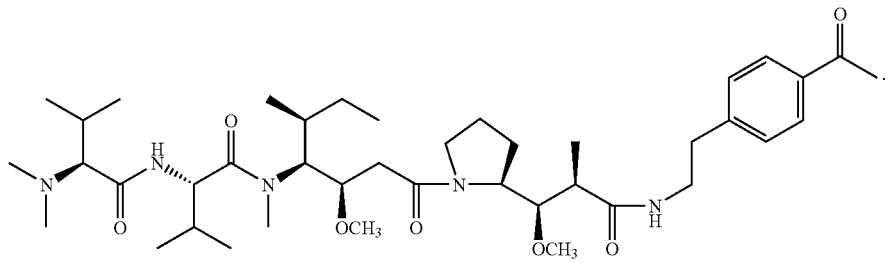

In various further embodiments, the pentapeptide drugs of the invention have one of the three general pentapeptide structure as shown above, wherein: $R^1$ is hydrogen; or $R^1$ and $R^2$ are methyl; and/or $R^3$ is isopropyl; and/or $R^4$ is selected from lower alkyl, aryl, and —$CH_2$—$C_{5-7}$carbocycle and $R^5$ is selected from H and methyl; or $R^4$ is selected from lower alkyl, and $R^5$ is selected from H and methyl; or $R^4$ and $R^5$ together form a carbocycle of the partial formula —$(CR^aR^b)_n$— wherein $R^a$ and $R^b$ are independently selected from hydrogen and lower alkyl and n is selected from 2, 3, 4, 5 and 6; and/or $R^6$ is lower alkyl; and/or $R^8$ is hydrogen; and/or $R^{11}$ is hydrogen; and/or $OR^{18}$ is =O; and/or $R^{19}$ is oxo-substituted lower alkyl.

General Synthesis

In various aspects as detailed above, the present invention provides drug-linker-ligand conjugates as well as precursors thereto. A drug-linker-ligand conjugate of the present invention is designed so that upon delivery of the conjugate to a cell, and particularly a tumor cell, the conjugate will partially degrade in a manner that frees the drug, from the ligand with perhaps some residue from the linker remaining attached to the drug, and typically with some residue of the linker remaining attached to the ligand. The drug (or drug-linker residue) will then act in a cytotoxic manner to kill the tumor cells, or at least to mitigate the multiplication of the tumor cells. The drug-linker-ligand conjugate may be referred to herein as a prodrug. The ligand is typically a targeting moiety that will localize the prodrug in the vicinity of a tumor cell.

The prodrug has the basic structure shown below:

acceptors are well known in the art, where exemplary thio acceptor group are maleimide and haloacetamide groups. The thiol acceptor group provides a convenient site for ligand attachment. At the other end, in a preferred aspect the heterobifunctional linker has a hydrazide group. Hydrazide groups are useful endgroups for a heterobifunctional linker because they readily react with carbonyl groups, i.e., aldehyde and ketone groups, where carbonyl groups can be readily incorporated into a pentapeptide compound as disclosed herein, to provide a hydrazone linkage. Incorporation of a hydrazone into the conjugate is particularly preferred in order to impart desired pH-sensitivity to the conjugate. Thus, under low pH conditions, as in acidic intracellular compartments (e.g., lysosomes), a hydrazone group will cleave and release the drug free from the ligand. A preferred linker is an acid-labile linker, that is cleaved under low pH conditions, i.e., conditions where the pH is less than about 6, preferably less than about 5.

The drugs of the present invention may be generally described as pentapeptides. Typically, pentapeptide drugs of the present invention can be prepared by introduction of a peptide bond between selected amino acids and/or modified amino acids, and/or peptide fragments. Such peptide bonds may be prepared, for example, according to the liquid phase synthesis method (see E. Schröder and K. Lübke, "The Peptides", volume 1, pp 76–136, 1965, Academic Press) that is well known in the field of peptide chemistry.

A preferred method to prepare pentapeptide drugs of the present invention entails preparing a dipeptide and a trip-

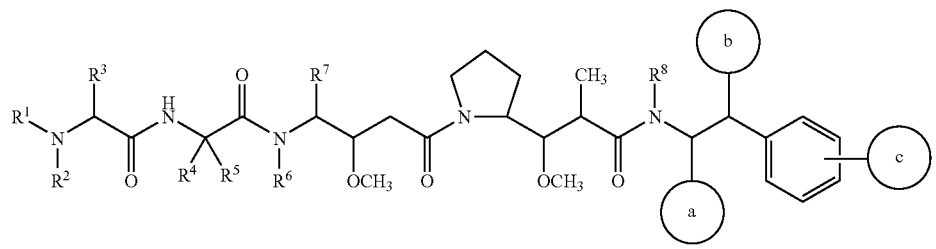

where the -linker-ligand portion of the prodrug is joined to the drug at any of positions a, b, or c. As described in more detail below, such conjugates are conveniently prepared using a heterobifunctional linker. In a preferred aspect of the invention, the heterobifunctional linker includes, on one end, a thiol acceptor i.e., a chemical moiety that will react with a thiol group so that the sulfur atom of the sulfur group becomes covalently bonded to the thiol acceptor. Thiol eptide, and combining stoichiometric equivalents of these two fragments in a one-pot reaction under suitable condensation conditions. This approach is illustrated in the following Schemes 1–3. Thus, the tripeptide 6 may be prepared as shown in Scheme 1, and the dipeptide 9 may be prepared as shown in Scheme 2. The two fragments 6 and 9 may be condensed to provide a pentapeptide (10) as shown in Scheme 3.

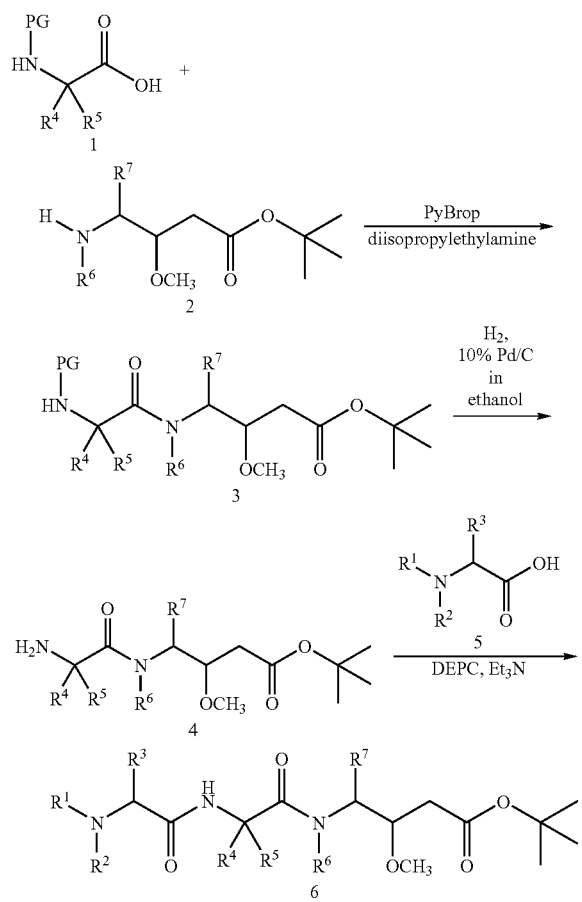

Scheme 1

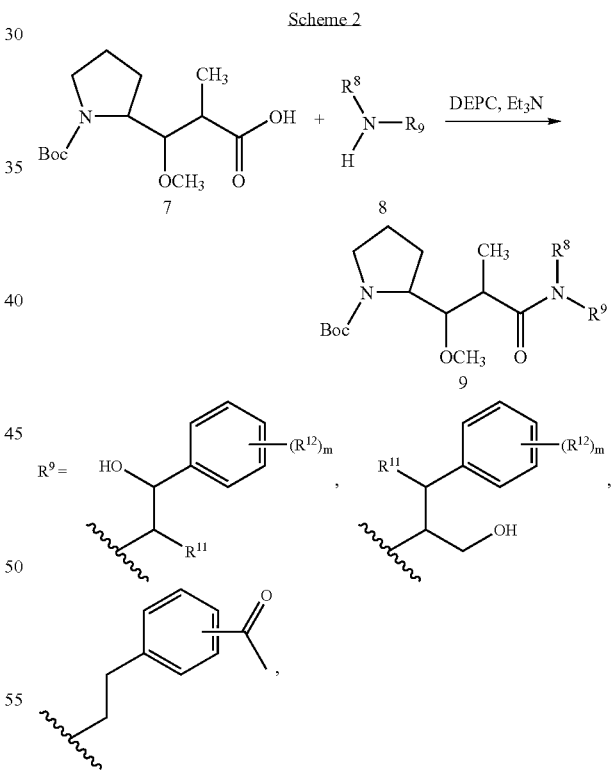

Scheme 2

As illustrated in Scheme 1, a PG-protected amino acid 1 (where PG represents an amine protecting group, e.g., benzyloxycarbonyl (which is a preferred PG and is represented herein by Z), $R^4$ is selected from lower alkyl, aryl, and —$CH_2$—$C_{5-7}$carbocyclic when $R^5$ is selected from H and methyl, or $R^4$ and $R^5$ together form a carbocyclic group of the partial formula —$(CR^aR^b)_n$— wherein $R^a$ and $R^b$ are independently selected from hydrogen and lower alkyl and n is selected from 2, 3, 4, 5 and 6) is coupled to t-butyl ester 2 (where $R^6$ is selected from hydrogen and lower alkyl; and $R^7$ is sec-butyl or iso-butyl) under suitable coupling conditions, e.g., in the presence of PyBrop and diisopropylethylamine, or using DCC (as accomplished, for example, by Miyazaki, K. et. al. *Chem. Pharm. Bull.* 1995, 43(10), 1706–1718).

Suitable protecting groups PG, and suitable synthetic methods to protect an amino group with a protecting group are well known in the art. See, e.g., Greene, T. W. and Wuts, P. G. M., Protective Groups in Organic Synthesis, 2nd Edition, 1991, John Wiley & Sons. A preferred protected amino acid 1 is PG-Ile, while other suitable protected amino acids include, without limitation: PG-cyclohexylglycine, PG-cyclohexylalanine, PG-aminocyclopropane-1-carboxylic acid, PG-α-aminoisobutyric acid, PG-phenylalanine, PG-phenylglycine, and PG-tert-butylglycine. Z, i.e., benzyloxycarbonyl, is a preferred protecting group. Fmoc is another preferred protecting group. A preferred t-butyl ester 2 is dolaisoleuine t-butyl ester.

After chromatographic purification, the dipeptide 3 is deprotected, e.g., using $H_2$ and 10% Pd—C in ethanol when PG is benzyloxycarbonyl, or using diethylamine for removal of an Fmoc protecting group. The resulting amine 4 readily forms a peptide bond with an amino acid 5 (where $R^1$ is selected from hydrogen and lower alkyl; $R^2$ is selected from hydrogen and lower alkyl; and $R^3$ is lower alkyl). N,N-Dialkyl amino acids are preferred amino acids 5, such as commercially available N,N-dimethyl valine. Other N,N-dialkyl amino acids can be prepared by reductive bis-alkylation following known procedures (see, e.g., Bowman, R. E, Stroud, H. H *J. Chem. Soc.*, 1950, 1342–1340). Fmoc-Me-L-Val and Fmoc-Me-L-glycine are two preferred amino acids 5 for the synthesis of N-monoalkyl derivatives. The amine 4 and the amino acid 5 are conveniently joined to provide the tripeptide 6 using coupling reagent DEPC with triethylamine as the base.

The dipeptide 9 can be readily prepared by condensation of the modified amino acid t-Boc-Dolaproine 7 (see, for example, Pettit, G. R., et al. *Synthesis*, 1996, 719–725), with commercially available (1S, 2R)-norephedrine, L- or D-phenylalaminol, or with synthetic p-acetylphenethylamine 8 (Shavel, J., Bobowski, G., 1969, U.S. Pat. No. 3,445,518) using condensing agents well known for peptide chemistry, such as, for example, DEPC in the presence of triethylamine, as shown in Scheme 2.

Scheme 3 illustrates the joining together of the tripeptide 6 with the dipeptide 9 to form a pentapeptide 10. The joining together of these two fragments can be accomplished using, e.g., TFA to facilitate Boc and t-butyl ester cleavage, respectively, followed by condensation conditions, e.g., utilizing DEPC, or similar coupling reagent, in the presence of excess base (triethylamine or equivalent) to give the desired product in moderate but acceptable yields.

Scheme 3

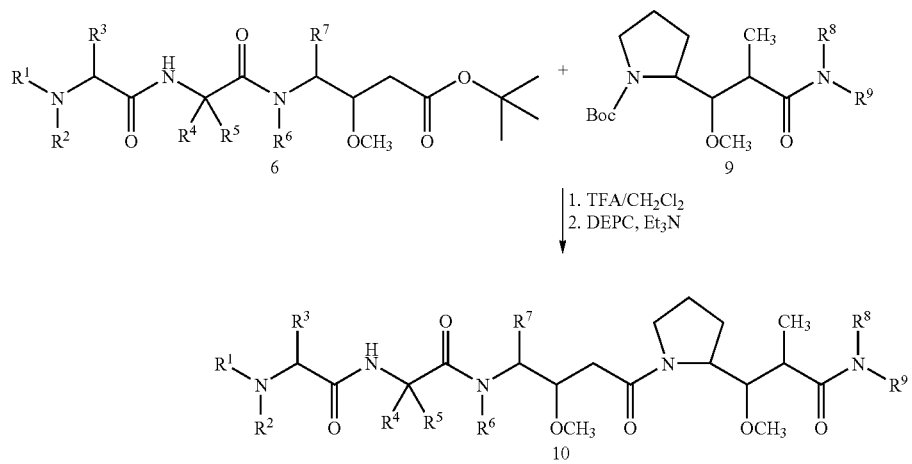

To obtain N-monoalkyl pentapeptide 10, the Fmoc group should be removed from the N-terminal amino acid after final coupling by treatment with diethylamine (see General Procedure E described below).

Upon proper selection of a, b, and c, the present invention provides pentapeptides of the formula

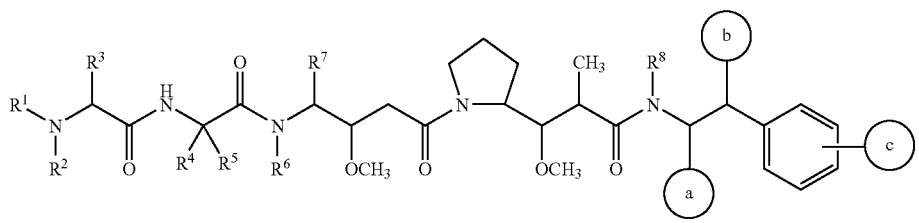

which are drugs of the present invention upon appropriate selection of a, b, and c, where these drugs may be prepared as described above. Thus, as referred to herein, the drugs of the present invention are not necessarily the same as the degradation product of the prodrugs of the present invention. Rather, the drugs of the present invention are pharmacologically active, cytotoxic chemicals of the above structure, which are conveniently utilized to prepare prodrugs of the present invention, where these prodrugs will release a pharmacologically active agent upon partial degradation of the prodrug.

Thus, in one aspect, the present invention provides drugs having the formula and pharmaceutically acceptable salts and solvates thereof wherein, independently at each location: $R^2$ is selected from hydrogen and lower alkyl; $R^3$ is lower alkyl; $R^4$ is selected from lower alkyl, aryl, and —$CH_2$—$C_{5-7}$carbocycle when $R^5$ is selected from H and methyl, or $R^4$ and $R^5$ together form a carbocycle of the partial formula —$(CR^aR^b)_n$— wherein $R^a$ and $R^b$ are independently selected from hydrogen and lower alkyl and n is selected from 2, 3, 4, 5 and 6; $R^6$ is selected from hydrogen and lower alkyl; $R^7$ is sec-butyl or iso-butyl; $R^8$ is selected from hydrogen and lower alkyl; $R^{11}$ is selected from hydrogen and lower alkyl; and $R^{18}$ is selected from hydrogen, a hydroxyl protecting group, and a direct bond where $OR^{18}$ represents =O.

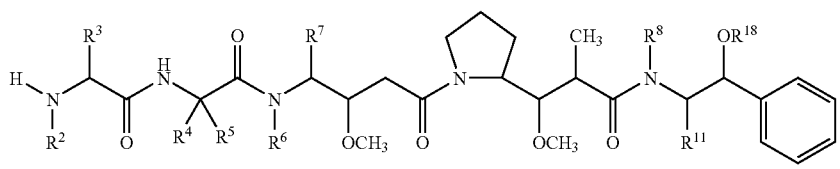

In another aspect, the present invention provides drugs having the formula

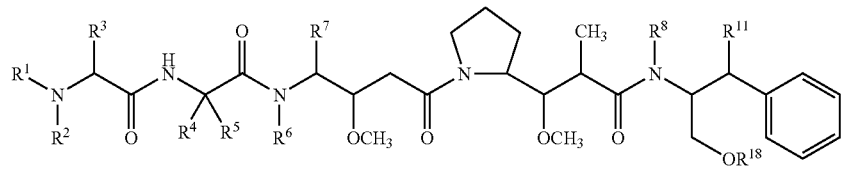

and pharmaceutically acceptable salts and solvates thereof wherein, independently at each location: $R^1$ is selected from hydrogen and lower alkyl; $R^2$ is selected from hydrogen and lower alkyl; $R^3$ is lower alkyl; $R^4$ is selected from lower alkyl, aryl, and —CH$_2$—C$_{5-7}$carbocycle when $R^5$ is selected from H and methyl, or $R^4$ and $R^5$ together form a carbocycle of the partial formula —(CR$^a$R$^b$)$_n$— wherein $R^a$ and $R^b$ are independently selected from hydrogen and lower alkyl and n is selected from 2, 3, 4, 5 and 6; $R^6$ is selected from hydrogen and lower alkyl; $R^7$ is sec-butyl or iso-butyl; $R^8$ is selected from hydrogen and lower alkyl; $R^{11}$ is selected from hydrogen and lower alkyl; and $R^{18}$ is selected from hydrogen, a hydroxyl protecting group, and a direct bond where OR$^{18}$ represents =O.

In another aspect, the present invention provides drugs having the formula

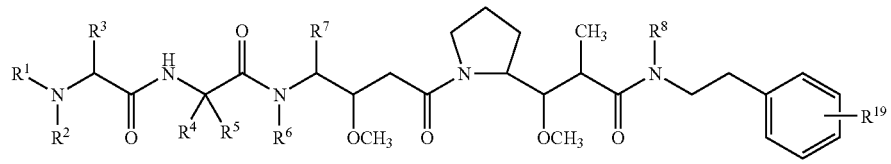

and pharmaceutically acceptable salts and solvates thereof wherein, independently at each location: $R^1$ is selected from hydrogen and lower alkyl; $R^2$ is selected from hydrogen and lower alkyl; $R^3$ is lower alkyl; $R^4$ is selected from lower alkyl, aryl, and —CH$_2$—C$_{5-7}$carbocycle when $R^5$ is selected from H and methyl, or $R^4$ and $R^5$ together form a carbocycle of the partial formula —(CR$^a$R$^b$)$_n$— wherein $R^a$ and $R^b$ are independently selected from hydrogen and lower alkyl and n is selected from 2, 3, 4, 5 and 6; $R^6$ is selected from hydrogen and lower alkyl; $R^7$ is sec-butyl or iso-butyl; $R^8$ is selected from hydrogen and lower alkyl; and $R^{19}$ is selected from hydroxy- and oxo-substituted lower alkyl.

In order to prepare a prodrug of the present invention, the drug is either directly reacted with a linker, typically a heterobifunctional linker, or else the drug is somewhat modified in order that it contains a reactive site that is suitably reactive with a reactive site on a heterobifunctional linker. In general, the heterobifunctional linker has the structure

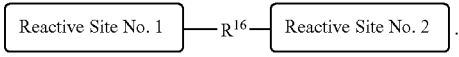

In a preferred embodiment of the invention, Reactive Site No. 1 is reactive with a carbonyl group of the drug, Reactive Site No. 2 is reactive with functionality on the ligand, and Reactive Sites 1 and 2 are reactive with different functional groups.

Many suitable heterobifunctional linkers are known in the art. See, e.g., S. S. Wong, Chemistry of Protein Conjugation and Crosslinking, CRC Press Inc., Boston 1991. In one aspect of the invention, Reactive Site No. 1 is a hydrazide, (i.e., a group of the formula

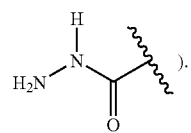

In one aspect of the invention, Reactive Site No. 2 is a thiol-accepting group. Suitable thiol-accepting groups include haloacetamide groups (i.e., groups of the formula

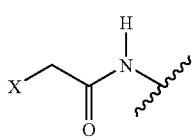

where X represents a halide) and maleimide groups (i.e., a group of the formula

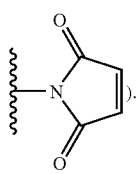

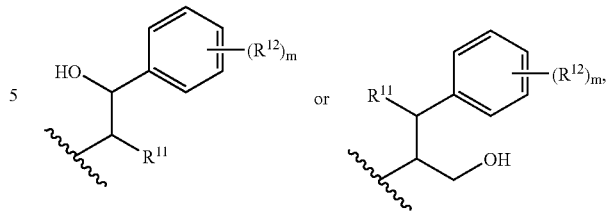

In the heterobifunctional linker of the present invention, $R^{16}$ is selected from arylene (lower alkylene), lower alkylene, arylene, and —$(CH_2OCH_2)_pCH_2$— where p is 1–5.

In general, suitable heterobifunctional linkers include commercially available maleimido hydrazides (e.g., β-maleimido propionic acid hydrazide, ε-maleimidocaproic acid hydrazide, and SMCC hydrazide, available from Molecular Biosciences, Inc. Boulder Colo.). Alternatively, the heterobifunctional linker can be easily prepared from a maleimido acid, including polyoxoethylene-based maleimido acids (Frisch, B., et al., *Bioconjugate Chem.*, 1996, 7, 180–186) according to known procedures (King, H. D., et al. *Bioconjugate Chem.*, 1999, 10, 279–288). According to this procedure, maleimido acids are first converted to their N-hydroxysuccinimide esters, followed by reaction with tert-butylcarbazate. After purification and Boc removal the maleimido hydrazide are usually obtained in good yields. Haloacetamide hydrazide heterobifunctional linkers can be prepared from available intermediates, for example succinimidyl 3-(bromoacetamido)propionate, or [2-[2-(2-bromoacetylamino)-ethoxy]-ethoxy]-acetic acid (Frisch, B., et al., *Bioconjugate Chem.*, 1996, 7, 180–186) by the reaction with tert-butylcarbazate described above.

In another aspect of the invention, Reactive Site No. 2 is an amine-reactive group. Suitable amine reactive groups include activated esters such as N-hydroxysuccinimide esters, p-nitrophenyl esters, pentafluorophenyl esters, and other reactive functionalities such as isothiocyanates, isocyanates, anhydrides, acid chlorides, and sulfonyl chlorides.

As indicated previously, in a preferred embodiment, the synthesis of the drug should provide for the presence of a carbonyl group, or at least a group that can be readily converted to, or elaborated to form, a carbonyl group. A carbonyl group may be readily made part of, or added to, the pentapeptide drug by any of the following exemplary procedures:

(1) oxidation of a hydroxyl group of the drug to form a carbonyl;

(2) reaction of a hydroxyl group of the drug with a molecule that contains both a carbonyl or protected carbonyl and a hydroxyl-reactive group, e.g., a carboxylic acid or ester. For instance, the hydroxyl group of the drug may be reacted with a keto acid or a keto ester, so as to convert the hydroxyl group to an ester group, where the ester group is joined to the keto group of the keto acid/ester;

(3) introducing a carbonyl group to the drug during synthesis of the drug, e.g., during peptide synthesis using carbonyl-containing amino acids, amines or peptides.

For example, if the pentapeptide 10 includes a carbonyl group, then it can be reacted directly with a heterobifunctional linker containing a carbonyl-reactive end, e.g., a hydrazide group. If the pentapeptide 10 does not include a carbonyl group, then a carbonyl group may be introduced into the pentapeptide in order to impart hydrazide reactivity to the pentapeptide. For instance, when $R^9$ is either of then the pentapeptide 10 can be subjected to oxidizing conditions, e.g., pyridinium chlorochromate (PCC)/pyridine (see, e.g., *Synthesis*, 1982, 245, 881, review), in order to provide the corresponding oxidized compounds wherein $R^9$ is

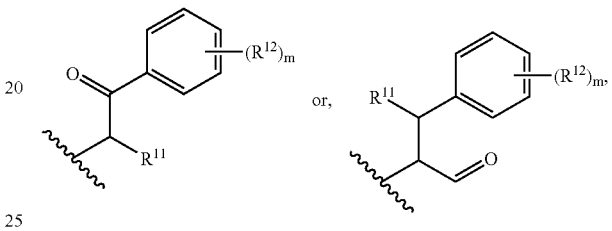

respectively.

Alternatively, if the pentapeptide 10 does not contain a carbonyl group but does contain a hydroxyl group, then this hydroxyl group can be elaborated to provide a carbonyl group. One way to provide carbonyl functionality from hydroxyl functionality is to react the hydroxyl group with a keto acid. The chemical literature describes many keto acids, and some keto acids are also available from commercial sources Most keto acids, although not α and β aliphatic keto acids, can be readily condensed with a hydroxyl group using DCC/DMAP chemistry to provide keto esters 11 (Larock, R. C., Comprehensive Organic Transformations, Wiley-VCH, 1999, p. 1937). Exemplary keto acids include, without limitation: levulinic acid, 4-acetylbutyric acid, 7-oxooctanoic acid, 4-acetylbenzoic acid, 4-carboxyphenylacetone, N-methyl-4-acetyl-3,5-dimethyl-2-pyrrole carboxylic acid, 3-benzoyl-2-pyridinecarboxylic acid, and 2-acetylthiazol-4-carboxylic acid.

The use of an α-keto acid to provide a carbonyl group requires initial protection of the carbonyl group as, for example, a dimethyl ketal. Dimethyl ketals can be readily obtained by treatment of keto acids with an excess of dimethylorthoformate in the presence of concentrated sulfuric acid as described, for example, in LaMattina, J. L., Muse, D. E. *J. Org. Chem.* 1987, 52, 3479–3481. After protection, standard DCC/DMAP-mediated condensation of the carboxyl group of the keto acid with the hydroxyl group of the pentapeptide can be used to form the ester bond. After aqueous work-up and low vacuum drying, this material may be used without further purification. Once the ester bond is formed, the dimethyl ketal can be hydrolyzed under mild acidic conditions to give the desired α-keto ester 11. Exemplary α-keto acids include, without limitation: pyruvic acid, 2-ketobutyric acid, 2-thiophenglyoxylic acid, and benzoylformic acid.

As illustrated in Scheme 4, preparation of β-keto esters of pentapeptides may be performed via DMAP-promoted transesterification of ethyl β-keto esters (see, e.g., Otera, *J. Chem. Rev.*, 1993, 93, 1449–1470). Commercially available β-keto esters that may be used in this transformation include, without limitation, ethyl acetoacetate, ethyl β-oxo-3-furanpropionate, and ethyl 3-(1-adamantyl)-3-oxopropionate. For instance, when $R^9$ is selected from

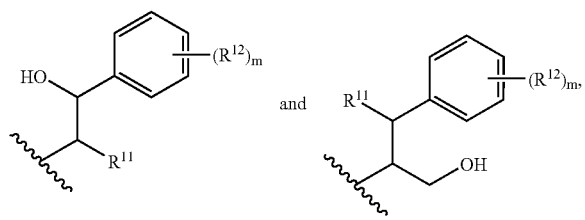

the hydroxyl group of $R^9$ may be reacted with a ketoacid to form an ester linkage and the desired carbonyl group. This approach to preparing carbonyl-containing drugs is shown in Scheme 4.

Scheme 4

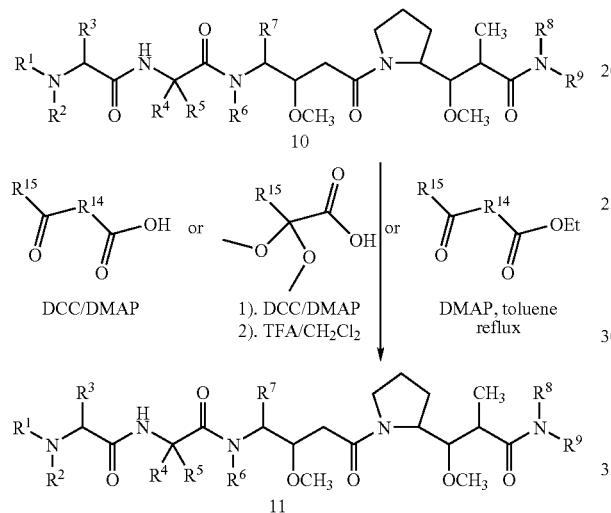

where, in compound 11, $R^9$ is selected from

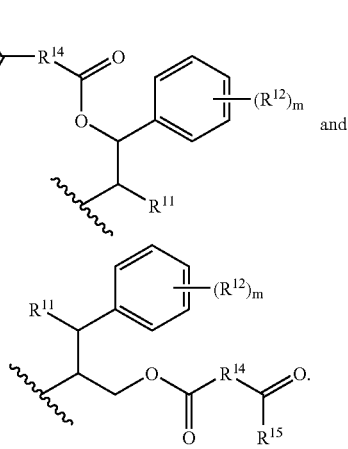

Once formed, the keto esters of pentapeptides can be isolated from the reaction mixture and purified by, for example, flash silica gel chromatography, and/or reversed phase high performance liquid chromatography.

Instead of utilizing an ester linkage to join the reactive carbonyl group (which may be reacted with a heterobifunctional linker) to the remainder of the drug, the reactive carbonyl group may be joined to the remainder of the drug via an ether linkage. That is, instead of providing a compound of the formula

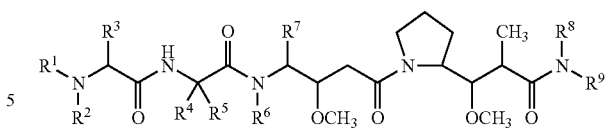

wherein, independently at each location: $R^1$ is selected from hydrogen and lower alkyl; $R^2$ is selected from hydrogen and lower alkyl; $R^3$ is lower alkyl; $R^4$ is selected from lower alkyl, aryl, and —$CH_2$—$C_{5-7}$carbocycle when $R^5$ is selected from H and methyl, or $R^4$ and $R^5$ together form a carbocycle of the partial formula —$(CR^aR^b)_n$— wherein $R^a$ and $R^b$ are independently selected from hydrogen and lower alkyl and n is selected from 2, 3, 4, 5 and 6; $R^6$ is selected from hydrogen and lower alkyl; $R^7$ is sec-butyl or iso-butyl; $R^8$ is selected from hydrogen and lower alkyl; $R^9$ is selected from

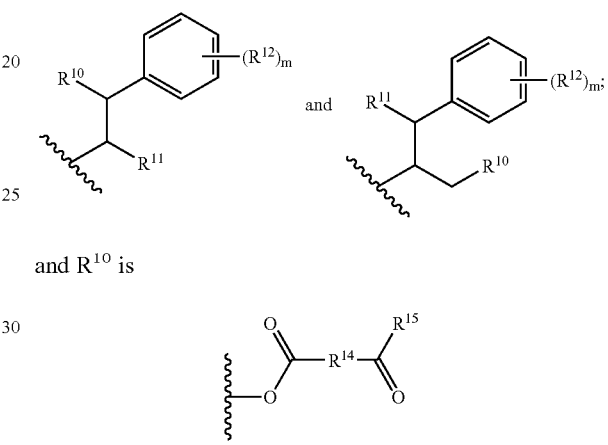

and $R^{10}$ is

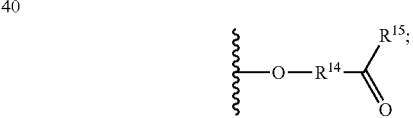

(i.e., an ester linkage in addition to $R^{14}$ is used to link a reactive carbonyl group to the remainder of the molecule), the present invention also provides compounds wherein $R^{10}$ is $$\text{\{—O—R}^{14}\text{—}\overset{R^{15}}{\underset{O}{C}}\text{;}$$

(i.e., an ether linkage in addition to $R^{14}$ is used to link a reactive carbonyl group to the remainder of the molecule) and, in either case (ether or ester linkage to $R^{14}$) $R^{11}$ is selected from hydrogen and lower alkyl; $R^{12}$ is selected from lower alkyl, halogen, and methoxy, and m is 0–5 where $R^{12}$ is independently selected at each occurrence; $R^{14}$ is selected from a direct bond, arylene (lower alkylene), lower alkylene and arylene; and $R^{15}$ is selected from hydrogen, lower alkyl and aryl.

Figure 16:
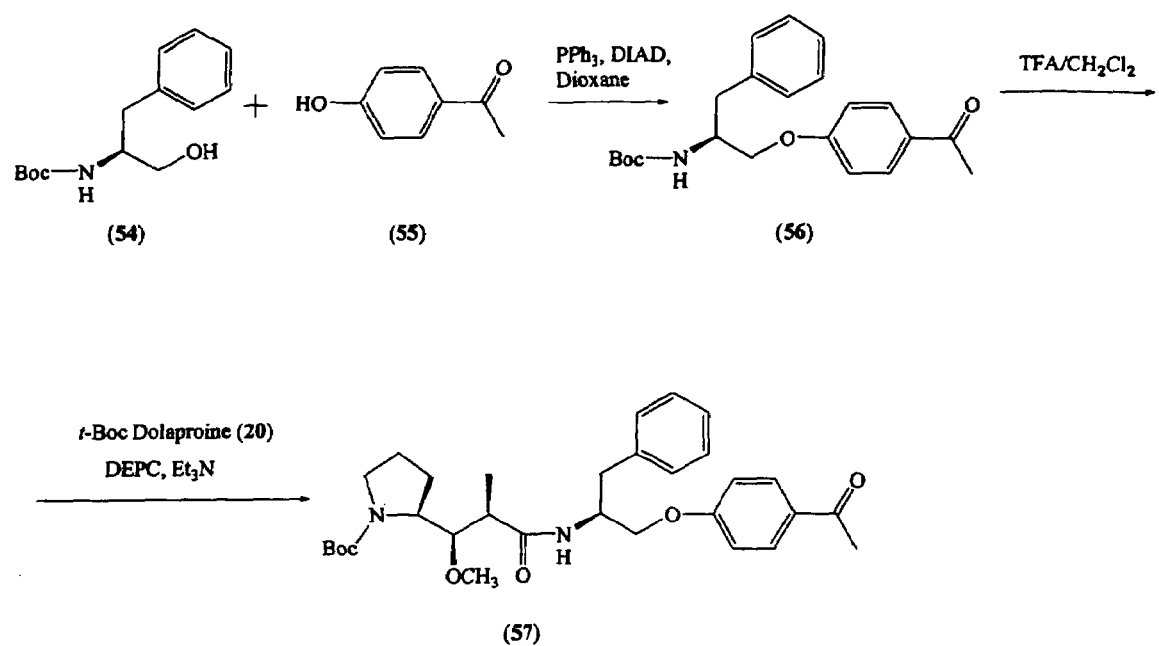
FIG. 16 shows a synthetic scheme illustrating the preparation of a specific dipeptide (57) useful in preparing compounds of the present invention.
Figure 17:
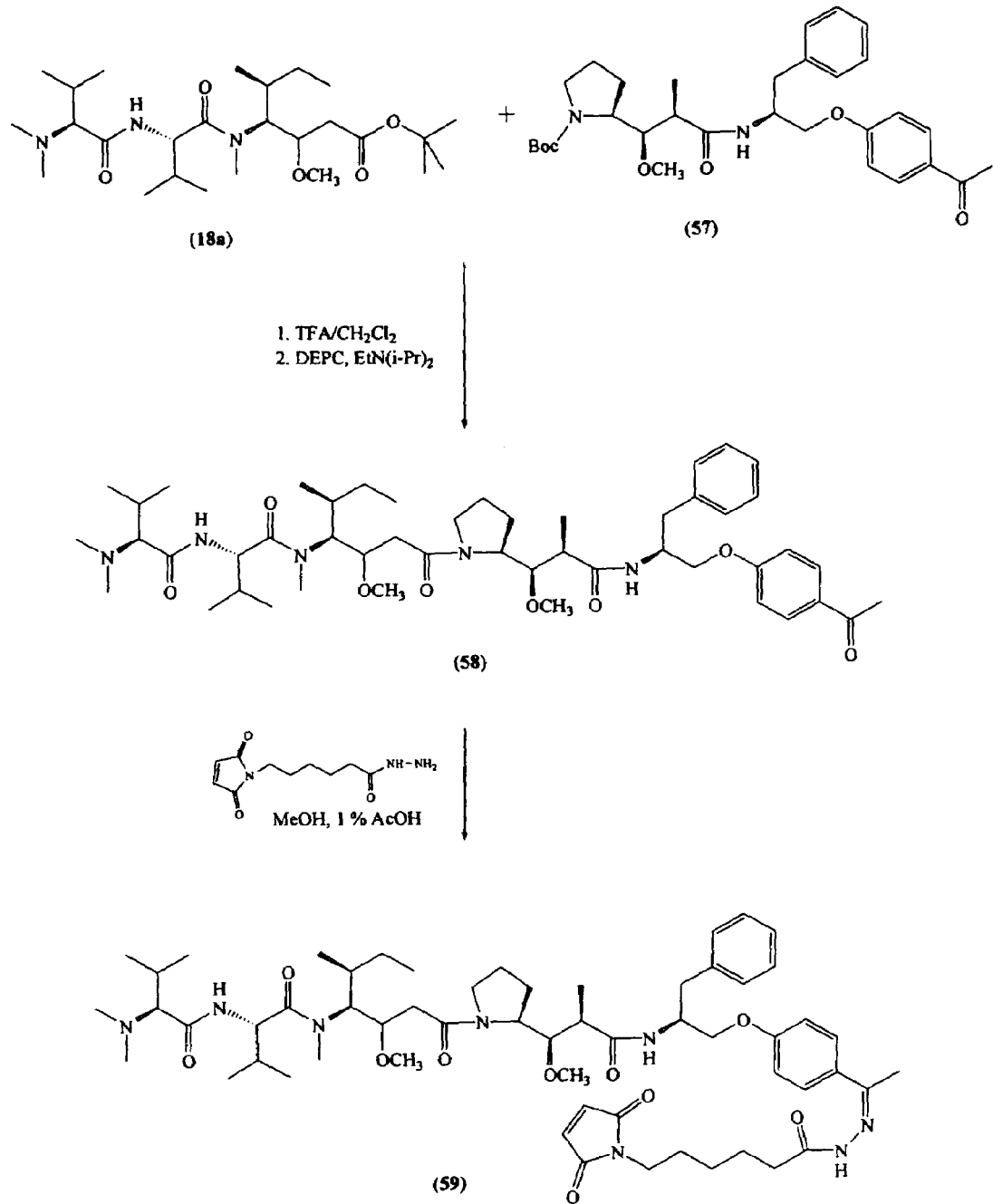
FIG. 17 shows a synthetic scheme for conjugating a pentapeptide (58) to a heterobifunctional linker to provide drug-reactive linker conjugate 59.

The preparation of pentapeptides having an ether linkage to $R^{14}$ is readily accomplished using amino alcohols (analogs of amino acids) which in turn are available from many commercial suppliers and are described in the chemical literature. The amino alcohol having a protected amino group (of general formula (protecting group) HN—R—OH where R is an organic moiety), may be reacted with an alcohol of the formula HO—$R^{14}$—C(=O)—$R^{15}$, for example via Mitsunobu reaction when $R^{14}$=aryl, in the presence of $PPh_3$, DIAD and a suitable solvent, e.g., dioxane, to provide the corresponding amino ether (of the formula (protecting group) HN—R—O—$R^{14}$—C(=O)—$R^{15}$). Upon deprotection of the amino group, this amino group can be reacted with a carboxylic acid or a synthon thereof, to provide a peptide (amide) group as a step toward the preparation of a pentapeptide. This chemistry is illustrated in FIGS. 16 and 17, where an exemplary and preferred amino alcohol is compound 54.

After reaction with a heterobifunctional linker, the resulting product is a pentapeptide drug conjugated to a linker moiety, where the linker moiety is a reactive linker moiety. In other words, the pentapeptide-linker conjugate contains a group that is reactive with functionality present on the ligand.

Thus, in one aspect, the present invention provides a pentapeptide-linker conjugate of the formula

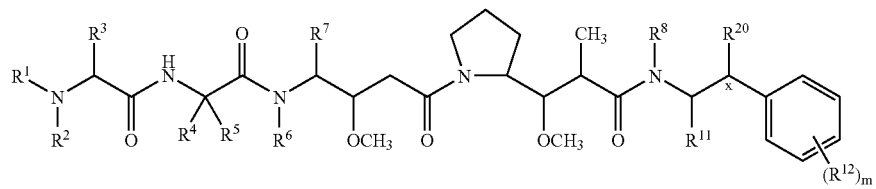

and pharmaceutically acceptable salts and solvates thereof wherein, independently at each location: $R^1$ is selected from hydrogen and lower alkyl; $R^2$ is selected from hydrogen and lower alkyl; $R^3$ is lower alkyl; $R^4$ is selected from lower alkyl, aryl, and —$CH_2$—$C_{5-7}$carbocycle when $R^5$ is selected from H and methyl, or $R^4$ and $R^5$ together form a carbocycle of the partial formula —$(CR^aR^b)_n$— wherein $R^a$ and $R^b$ are independently selected from hydrogen and lower alkyl and n is selected from 2, 3, 4, 5 and 6; $R^6$ is selected from hydrogen and lower alkyl; $R^7$ is sec-butyl or iso-butyl; $R^8$ is selected from hydrogen and lower alkyl; $R^1$ is selected from hydrogen and lower alkyl; $R^{12}$ is selected from lower alkyl, halogen, and methoxy, and m is 0–5 where $R^{12}$ is independently selected at each occurrence; and $R^{20}$ is a reactive linker group having a reactive site that allows $R^{20}$ to be reacted with a targeting moiety.

In another aspect, the present invention provides a pentapeptide-linker conjugate of the formula

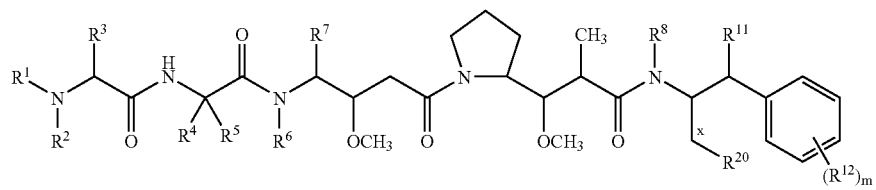

and pharmaceutically acceptable salts and solvates thereof wherein, independently at each location: $R^1$ is selected from hydrogen and lower alkyl; $R^2$ is selected from hydrogen and lower alkyl; $R^3$ is lower alkyl; $R^4$ is selected from lower alkyl, aryl, and —$CH_2$—$C_{5-7}$carbocycle when $R^5$ is selected from H and methyl, or $R^4$ and $R^5$ together form a carbocycle of the partial formula —$(CR^aR^b)_n$— wherein $R^a$ and $R^b$ are independently selected from hydrogen and lower alkyl and n is selected from 2, 3, 4, 5 and 6; $R^6$ is selected from hydrogen and lower alkyl; $R^7$ is sec-butyl or iso-butyl; $R^8$ is selected from hydrogen and lower alkyl; $R^1$ is selected from hydrogen and lower alkyl; $R^{12}$ is selected from lower alkyl, halogen, and methoxy, and m is 0–5 where $R^{12}$ is independently selected at each occurrence; and $R^{20}$ is a reactive linker group having a reactive site that allows $R^{20}$ to be reacted with a targeting moiety.

In yet another aspect, the present invention provides a pentapeptide-linker conjugate of the formula

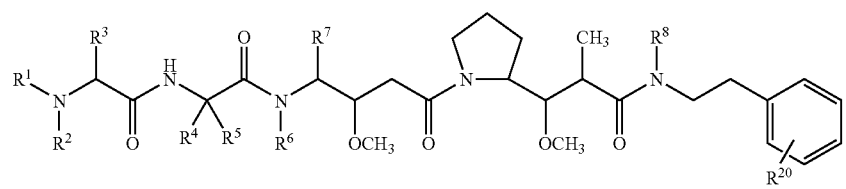

and pharmaceutically acceptable salts and solvates thereof wherein, independently at each location: $R^1$ is selected from hydrogen and lower alkyl; $R^2$ is selected from hydrogen and lower alkyl; $R^3$ is lower alkyl; $R^4$ is selected from lower alkyl, aryl, and —$CH_2$—$C_{5-7}$carbocycle when $R^5$ is selected from H and methyl, or $R^4$ and $R^5$ together form a carbocycle of the partial formula —$(CR^aR^b)_n$— wherein $R^a$ and $R^b$ are independently selected from hydrogen and lower alkyl and n is selected from 2, 3, 4, 5 and 6; $R^6$ is selected from hydrogen and lower alkyl; $R^7$ is sec-butyl or iso-butyl; $R^8$ is selected from hydrogen and lower alkyl; and $R^{20}$ is a reactive linker group having a reactive site that allows $R^{20}$ to be reacted with a targeting moiety.

As shown in Scheme 5, hydrazone bond formation between the heterobifunctional linker and the carbonyl-containing pentapeptide drug, followed by treatment with the ligand, will provide compounds of formula I. The reaction of the drug with the heterobifunctional linker may be performed in a suitable solvent, e.g., anhydrous MeOH or DMSO, preferably in the presence of a small amount of acid, e.g., 0.1% AcOH or TFA at room temperature. The relative amounts of hydrazide to be applied and the time required for complete, or near complete reaction depends on the nature of the carbonyl group. Aromatic and α-carbonyl groups generally require higher excess of hydrazide and longer reaction time. The procedures of King, H. D., et al. *Bioconjugate Chem.*, 1999, 10, 279–288, as used to prepare Doxorubicin-mAb conjugates, may be utilized to prepare the conjugates of the present invention. Stable hydrazones may be purified by a reversed phase HPLC. Hydrazone stability typically depends on the nature of corresponding keto esters.

The ligand is preferably a targeting ligand that directs the conjugate to a desired location in the animal subject. A preferred targeting ligand is an antibody, e.g., a chimeric or humanized antibody, or a fragment thereof. Internalizing monoclonal antibodies, e.g., BR96, AC10, herceptin, and S2C6 are preferred antibodies of the present invention. The ligand is suitably joined to the linker through a free thiol group or a free amino group on the ligand. For instance, when the ligand is an antibody, the free thiol group may be generated by reduction of a disulfide group present in the antibody with dithiothreitol as previously described (Trail, P. A. et al., *Science* 1993, 261, 212–215, and Firestone, R. A. Willner, D., Hofstead, S. J., King, H. D., Kaneko, T, Braslawsky, G. R., Greenfield, R. S., Trail, P. A., Lasch, S. J., Henderson, A. J., Casazza, A. M., Hellström, I., and Hellström, K. E., "Synthesis and antitumor activity of the immunoconjugate BR96-Dox" *J. Controlled Rel.* 1996, 39, 251–259). Alternatively, a lysine of the antibody may be reacted with iminothiolane hydrochloride (Traut's reagent) to introduce free thiol groups. Alternatively, free amino groups of the antibody may be reacted directly with linker-drug bearing suitable functionality, e.g., activated ester, isothiocyanate, isocyanate, anhydride, or acyl chloride functionalities. The drug-linker-ligand conjugate of the invention retains both specificity and therapeutic drug activity for the treatment of cell population expressing specific antigen for the ligand. Stable in serum, the hydrazone bond of the conjugate will be cleaved in acidic intracellular compartments releasing free highly-potent drug. This approach may be used to provide conjugates with high selectivity between target and non-target cell lines for example with up to about 1000 fold selectivity.

Scheme 5 illustrates the conjugation of the carbonyl-containing drug to a ligand through a heterobifunctional linker to form a compound of formula I.

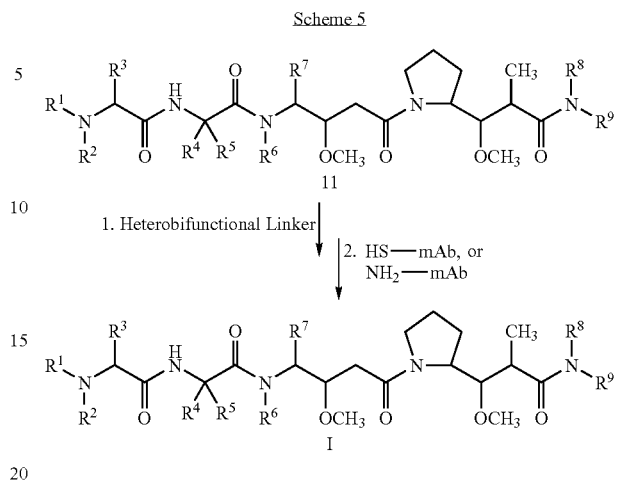

wherein, in the compound of formula I, and independently at each location: $R^1$ is selected from hydrogen and lower alkyl; $R^2$ is selected from hydrogen and lower alkyl; $R^3$ is lower alkyl; $R^4$ is selected from lower alkyl, aryl, and —$CH_2$-$C_{5-7}$carbocyclic when $R^5$ is selected from H and methyl, or $R^4$ and $R^5$ together form a carbocyclic group of the partial formula —$(CR^aR^b)_n$— wherein $R^a$ and $R^b$ are independently selected from hydrogen and lower alkyl and n is selected from 2, 3, 4, 5 and 6; $R^6$ is selected from hydrogen and lower alkyl; $R^7$ is sec-butyl or iso-butyl; $R^8$ is selected from hydrogen and lower alkyl; $R^9$ is selected from

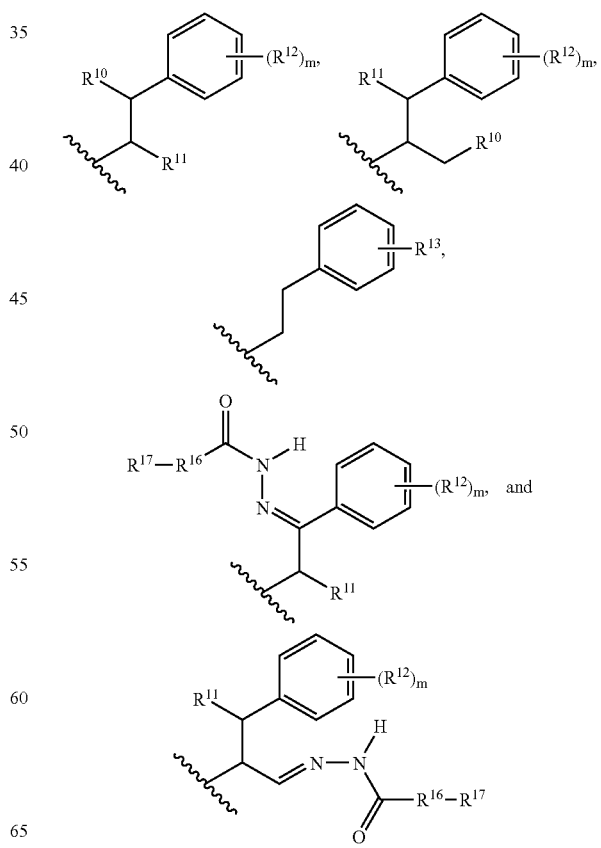

$R^{10}$ is selected from

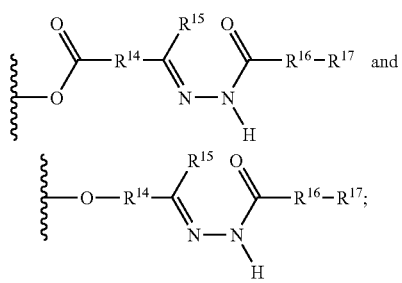

$R^{11}$ is selected from hydrogen and lower alkyl; $R^{12}$ is selected from lower alkyl, halogen, and methoxy, and m is 0–5 where $R^{12}$ is independently selected at each occurrence; $R^{13}$ is

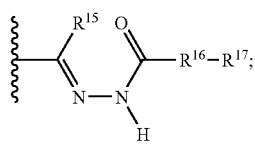

$R^{14}$ is selected from a direct bond, arylene (lower alkylene), lower alkylene and arylene; $R^{15}$ is selected from hydrogen, lower alkyl and aryl; $R^{16}$ is selected from arylene (lower alkylene), lower alkylene, arylene, and —$(CH_2OCH_2)_p$ $CH_2$— where p is 1–5; and $R^{17}$ is selected from

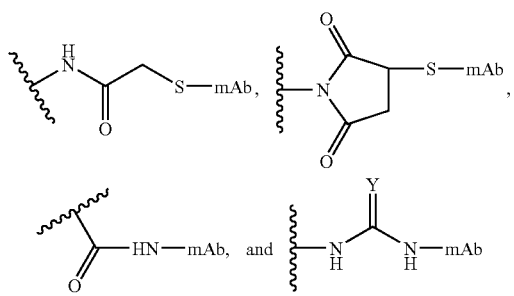

where Y=O or S,

As mentioned above, and as indicated by the identity of $R^{17}$ in the foregoing structure, a preferred ligand is a monoclonal-antibody as defined herein. Some exemplary monoclonal antibodies include BR96 mAb (Trail, P. A., Willner, D., Lasch, S. J., Henderson, A. J., Hofstead, S. J., Casazza, A. M., Firestone, R. A., Hellström, I., Hellström, K. E., "Cure of Xenografted Human Carcinomas by BR96-Doxorubicin Immunoconjugates" Science 1993, 261, 212–215), BR64 (Trail, P A, Willner, D, Knipe, J., Henderson, A. J., Lasch, S. J., Zoeckler, M. E., Trailsmith, M. D., Doyle, T. W., King, H. D., Casazza, A. M., Braslawsky, G. R., Brown, J. P., Hofstead, S. J., Greenfield, R. S., Firestone, R. A., Mosure, K., Kadow, D. F., Yang, M. B., Hellstrom, K. E., and Hellstrom, I. "Effect of Linker Variation on the Stability, Potency, and Efficacy of Carcinoma-reactive BR64-Doxorubicin Immunoconjugates" Cancer Research 1997, 57, 100–105, herceptin (Stebbing, J., Copson, E., and O'Reilly, S. "Herceptin (trastuzamab) in advanced breast cancer" Cancer Treat Rev. 26, 287–90, 2000), mAbs against the CD 40 antigen, such as S2C6 mAb (Francisco, J. A., Donaldson, K. L., Chace, D., Siegall, C. B., and Wahl, A. F. "Agonistic properties and in vivo antitumor activity of the anti-CD40 antibody, SGN-14" Cancer Res. 2000, 60, 3225–3231), and mAbs against the CD30 antigen, such as AC10 (Bowen, M. A., Olsen, K. J., Cheng, L., Avila, D., and Podack, E. R. "Functional effects of CD30 on a large granular lymphoma cell line YT" J. Immunol., 151, 5896–5906, 1993). Many other internalizing mAbs that bind to tumor associated antigens can be used in this invention, and have been reviewed (Franke, A. E., Sievers, E. L., and Scheinberg, D. A., "Cell surface receptor-targeted therapy of acute myeloid leukemia: a review" Cancer Biother Radiopharm. 2000,15, 459–76; Murray, J. L., "Monoclonal antibody treatment of solid tumors: a coming of age" Semin Oncol. 2000, 27, 64–70; Breitling, F., and Dubel, S., Recombinant Antibodies, John Wiley, and Sons, New York, 1998).

Compositions

In other aspects, the present invention provides pentapeptide drugs as described above, and prodrugs as also described above that are based on the pentapeptide drugs, in combination with a pharmaceutically acceptable carrier, excipient or diluent. For convenience, the pentapeptide drugs and the prodrugs of the invention will simply be referred to as compounds of the invention. Thus, the present invention provides a pharmaceutical or veterinary composition (hereinafter, simply referred to as a pharmaceutical composition) containing a compound of the invention as described above, in admixture with a pharmaceutically acceptable carrier. The invention further provides a composition, preferably a pharmaceutical composition, containing an effective amount of a compound as described above, in association with a pharmaceutically acceptable carrier.

The pharmaceutical compositions of the present invention may be in any form that allows for the composition to be administered to an animal subject. For example, the composition may be in the form of a solid, liquid or gas (aerosol). Typical routes of administration include, without limitation, oral, topical, parenteral, sublingual, rectal, vaginal, ocular, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to an animal subject. Compositions that will be administered to a subject take the form of one or more dosage units, where for example, a tablet may be a single dosage unit, and a container of a compound of the invention in aerosol form may hold a plurality of dosage units.

Materials used in preparing the pharmaceutical compositions should be pharmaceutically pure and non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration, and the composition employed.

In general, the pharmaceutical composition includes an (where "a" and "an" refers here, and throughout this specification, to one or more) active compounds of the invention in admixture with one or more carriers. The carrier(s) may be particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, chewing gum, wafer or the like form. Such a solid composition will typically contain one or more inert diluents or edible carriers. In addition, one or more of the following adjuvants may be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol, cyclodextrin or a fatty oil.

The composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent may be included.

The liquid pharmaceutical compositions of the invention, whether they are solutions, suspensions or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of a compound of the present invention such that a suitable dosage will be obtained. Typically, this amount is at least 0.01% of a compound of the invention in the composition. When intended for oral administration, this amount may be varied to be between 0.1% and about 80% of the weight of the composition. Preferred oral compositions contain between about 4% and about 50% of the compound of the invention. Preferred compositions and preparations according to the present invention are prepared so that a parenteral dosage unit contains between 0.01% to 2% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of a compound of the present invention of from about 0.1% to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

The composition may include various materials that modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, spacers and the like, which together may form a kit. Preferred aerosols may be determined by one skilled in the art, without undue experimentation.

Whether in solid, liquid or gaseous form, the pharmaceutical composition of the present invention may contain one or more known pharmacological agents used in the treatment of cancer.

The pharmaceutical compositions may be prepared by methodology well known in the pharmaceutical art. For example, a composition intended to be administered by injection can be prepared by combining a compound of the invention with water so as to form a solution. A surfactant may be added to facilitate the formation of a homogeneous solution or suspension. Surfactants are compounds that non-covalently interact with a compound of the invention so as to facilitate dissolution or homogeneous suspension of the active compound in the aqueous delivery system.

Biological Activity and Utility of Compounds

The present invention provides biologically-active compounds and pro-drugs (collectively, compounds, or compounds of the invention), methods of preparing compounds of the invention, pharmaceutical compositions comprising the compounds of the invention, and methods for treatment of cancers and other tumors in animal subjects. For instance, the invention provides compounds and compositions for use in a method for treating tumors wherein the animal subject is treated, in a pharmaceutically acceptable manner, with a pharmaceutically effective amount of a compound or composition of the present invention.

The compounds and compositions of the invention can be used in a variety of settings for the treatment of mammalian cancers. The mAb-pentapeptide conjugates can be used to deliver the cytotoxic drug to tumor cells. Once the antibody has bound to tumor associated antigens, it is taken up inside cells through receptor-mediated endocytosis into endosomes and lysosomes. These intracellular vesicles are acidic and can induce the hydrolysis of an acid-sensitive linker bond, e.g., a hydrazone bond, between the drugs and the mAbs. In addition, ester bonds can be cleaved by proteases and esterases, which are in abundance within lysosomes. The released drug is then free to migrate in the cytosol and induce cytotoxic activities.

The specificity of the mAb for a particular tumor type will dictate which tumors will be treated with the immunoconjugates. For example, BR96-pentapeptide conjugates may be used to treat antigen positive carcinomas including those of the lung, breast, colon, ovaries, and pancreas. Anti-CD30-pentapeptide and anti-CD40-pentapeptide conjugates may be used for treating hematologic malignancies.

The free drugs of the invention may also be used as chemotherapeutics in the untargeted form. For example, the pentapeptides of the present invention may be used against ovarian, CNS, renal, lung, colon, melanoma, and hematologic tumors.

Conjugation of these highly potent drugs to monoclonal antibodies specific for tumor markers results in specific targeting, thus reducing general toxicity of these compounds. pH-Sensitive linkers should provide stability of the conjugate in blood, yet should be hydrolyzed in acidic intracellular compartments liberating active drug.

The following examples are provided by way of illustration and not limitation.

EXAMPLES

Figure 2:
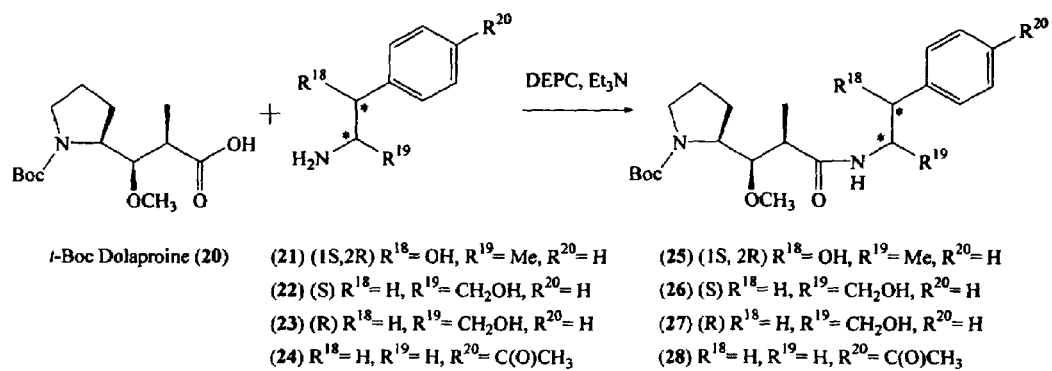
FIG. 2 shows a synthetic scheme illustrating the preparation of specific dipeptides useful in preparing compound of the present invention.
Figure 3:
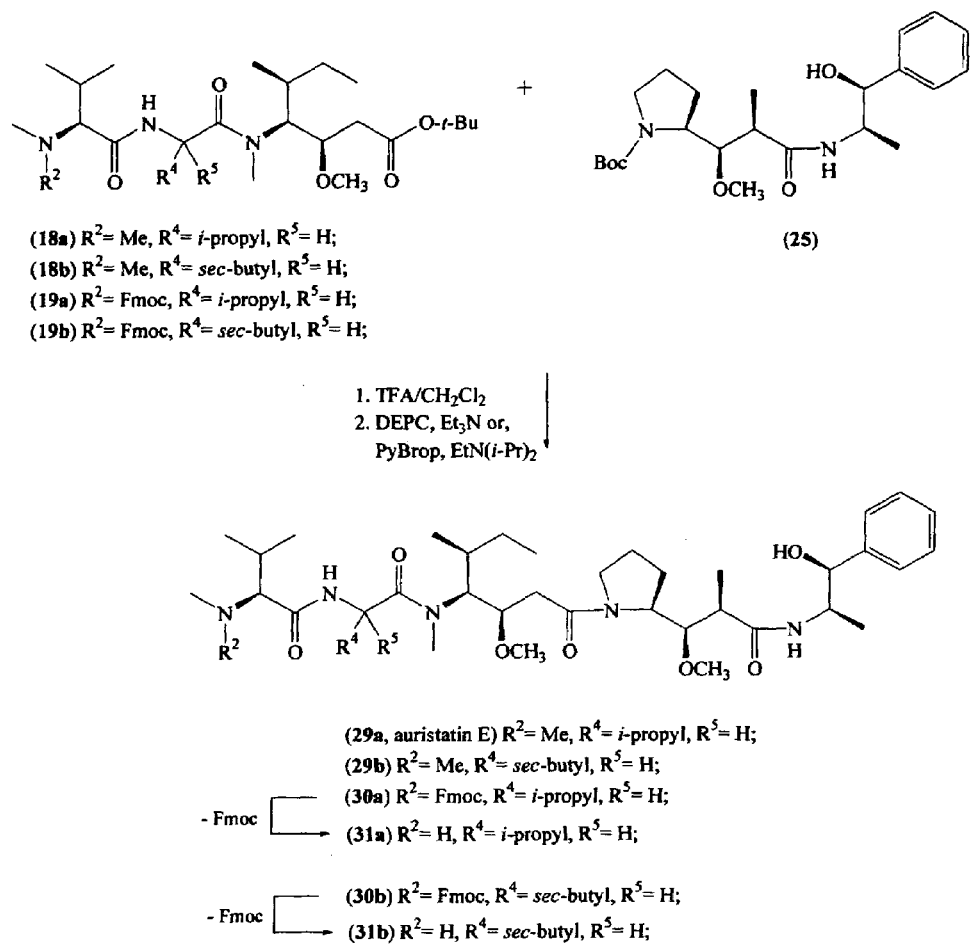
FIGS. 3, 4 and 5 show synthetic schemes illustrating the preparation of pentapeptides from tripeptides and dipeptides
Figure 4:
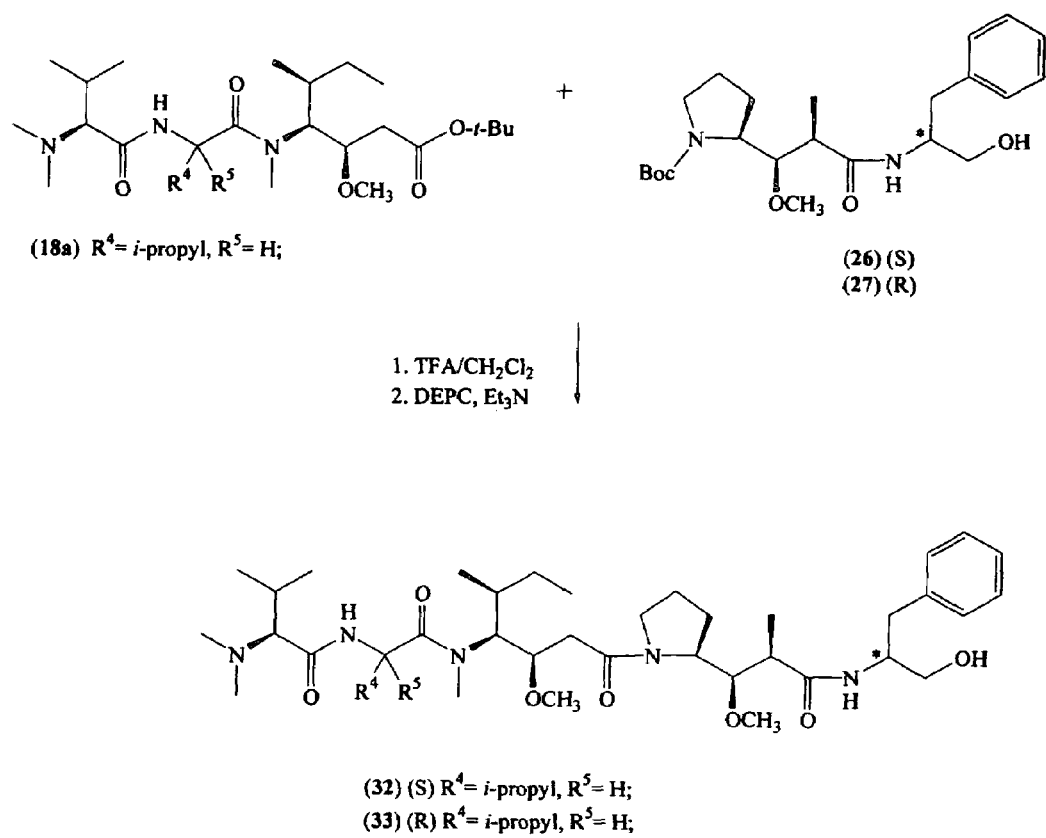
Figure 5:
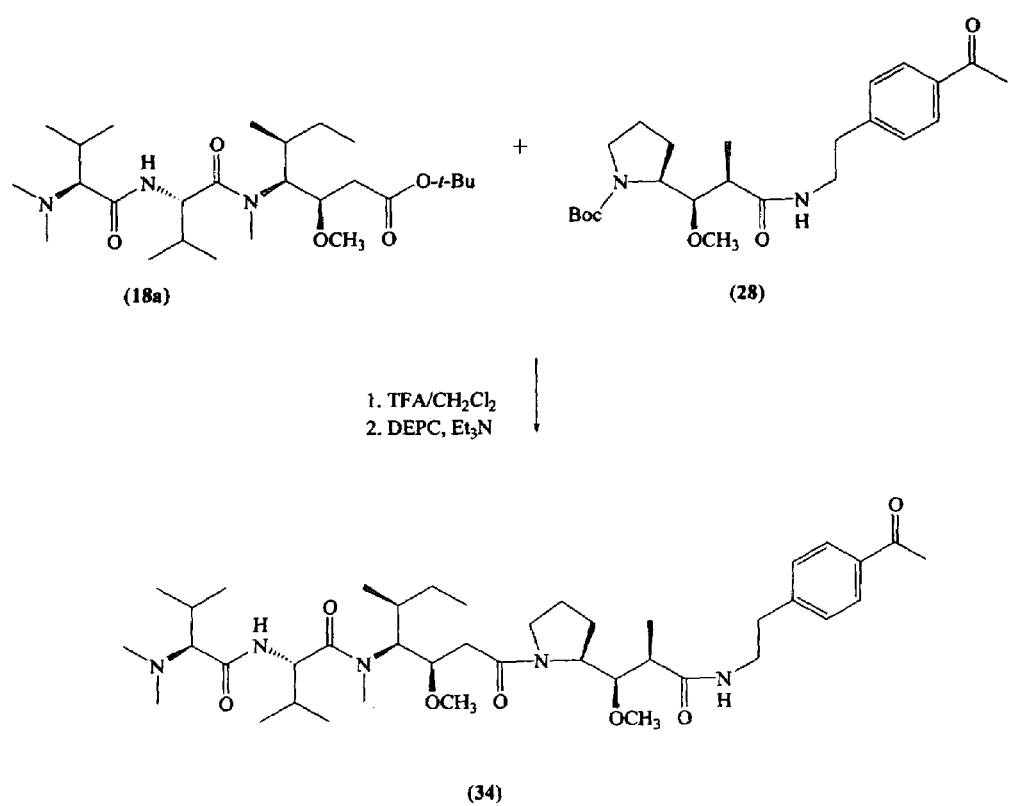
Figure 6:
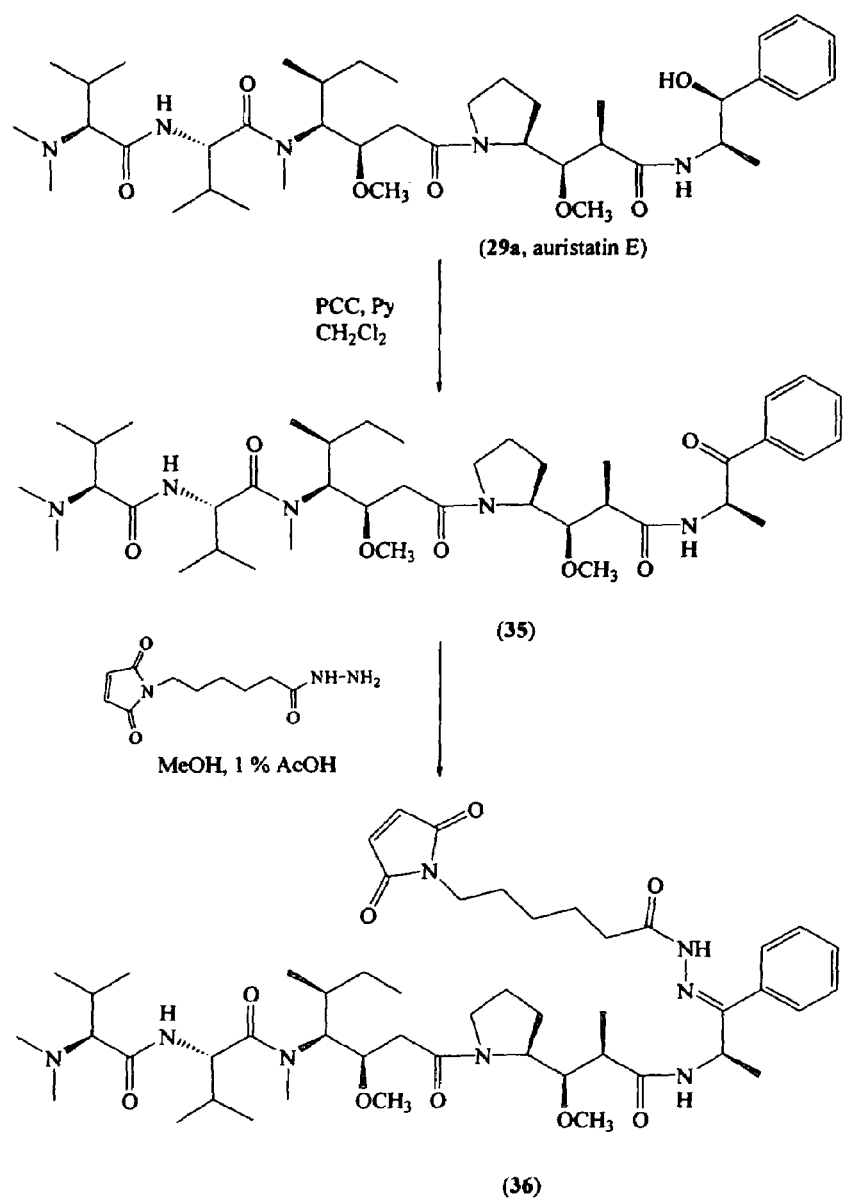
FIGS. 6, 7 and 8 show synthetic schemes for conjugating a pentapeptide to a heterobifunctional linker to provide ligand (specifically a mAb) reactive drug molecules.
Figure 7:
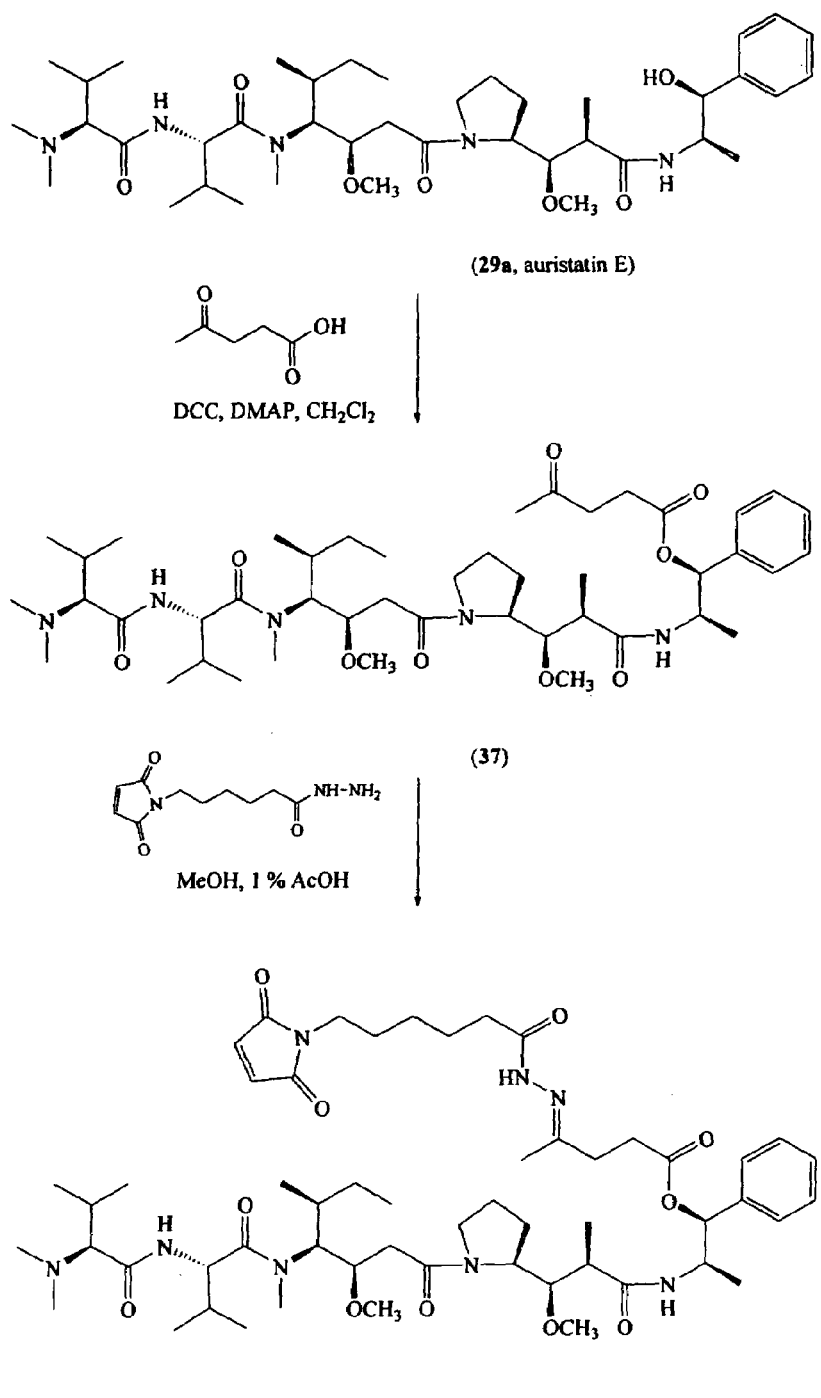
Figure 8:
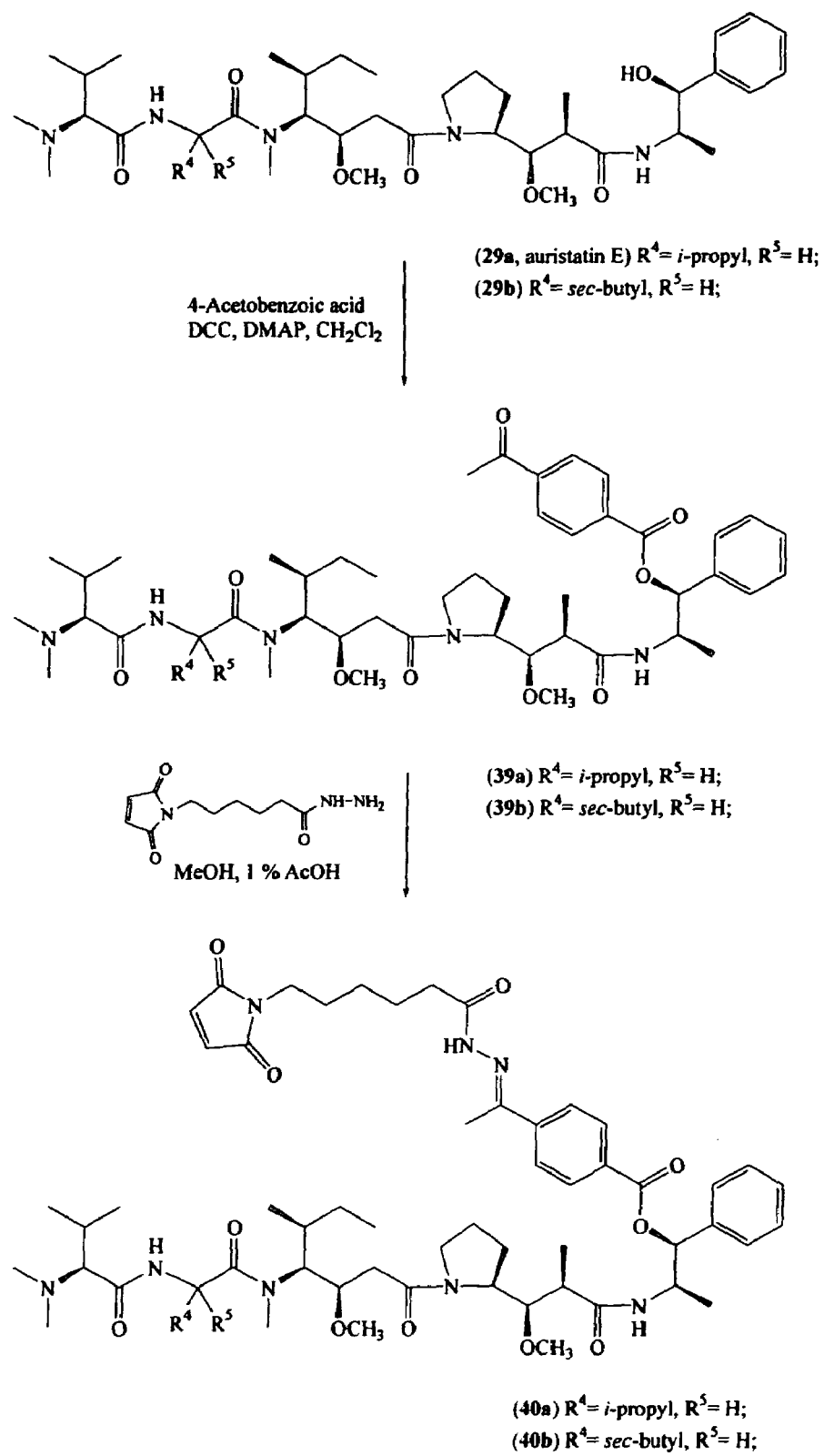
Figure 9:
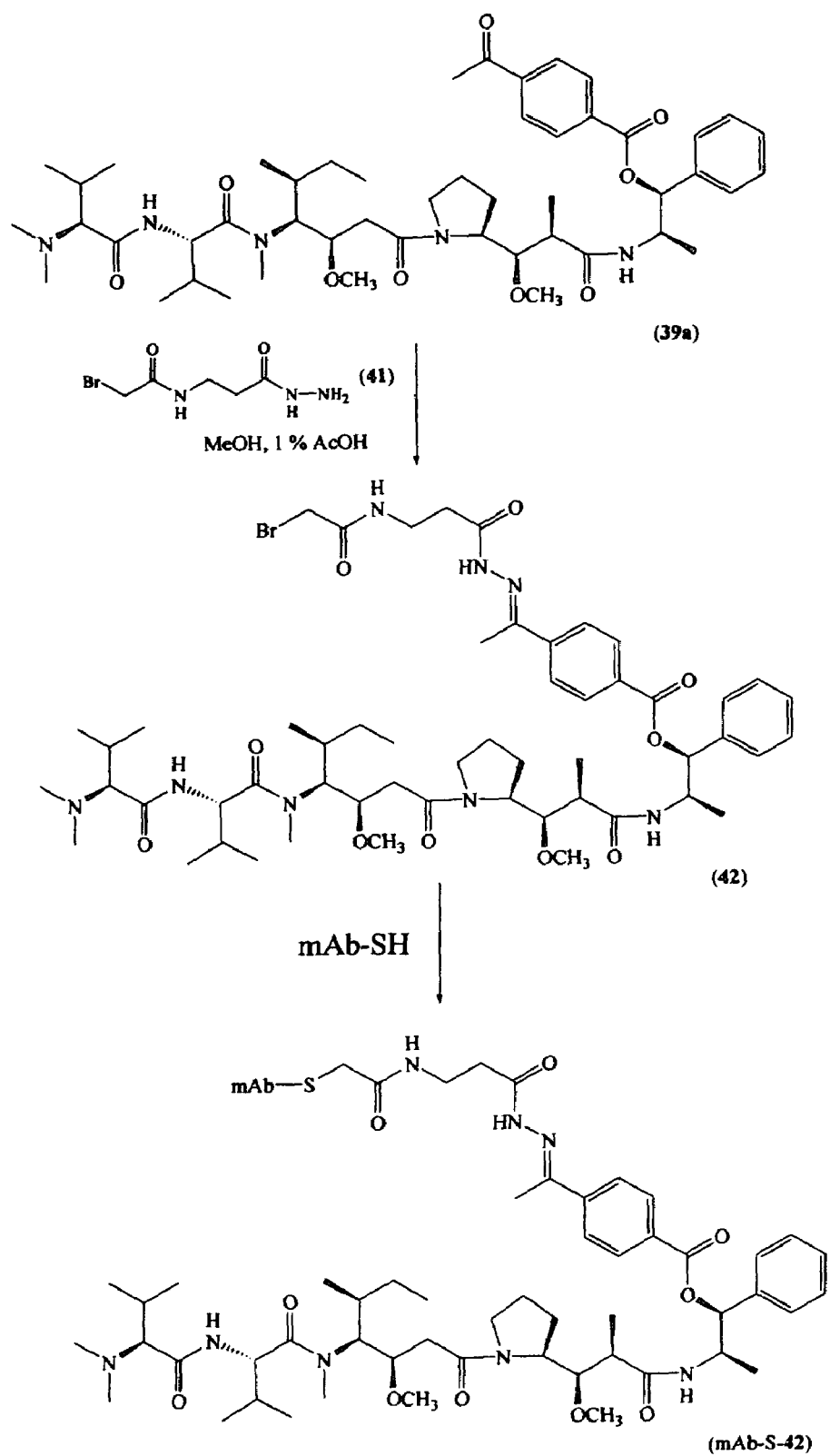
FIGS. 9, 10, 11 and 12 show synthetic schemes for conjugating a ligand, and specifically a mAb, to a drug-reactive linker conjugate to provide prodrugs of the present invention.
Figure 10:
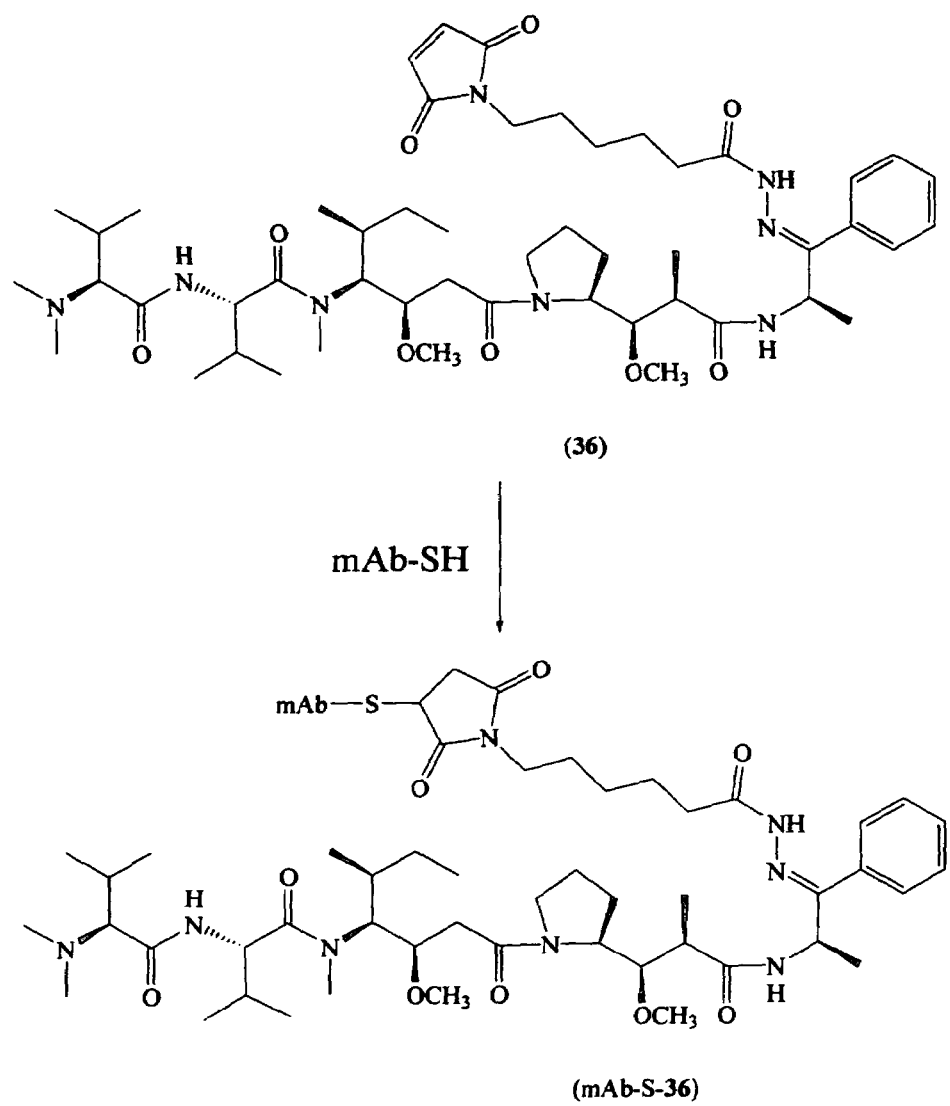
Figure 11:
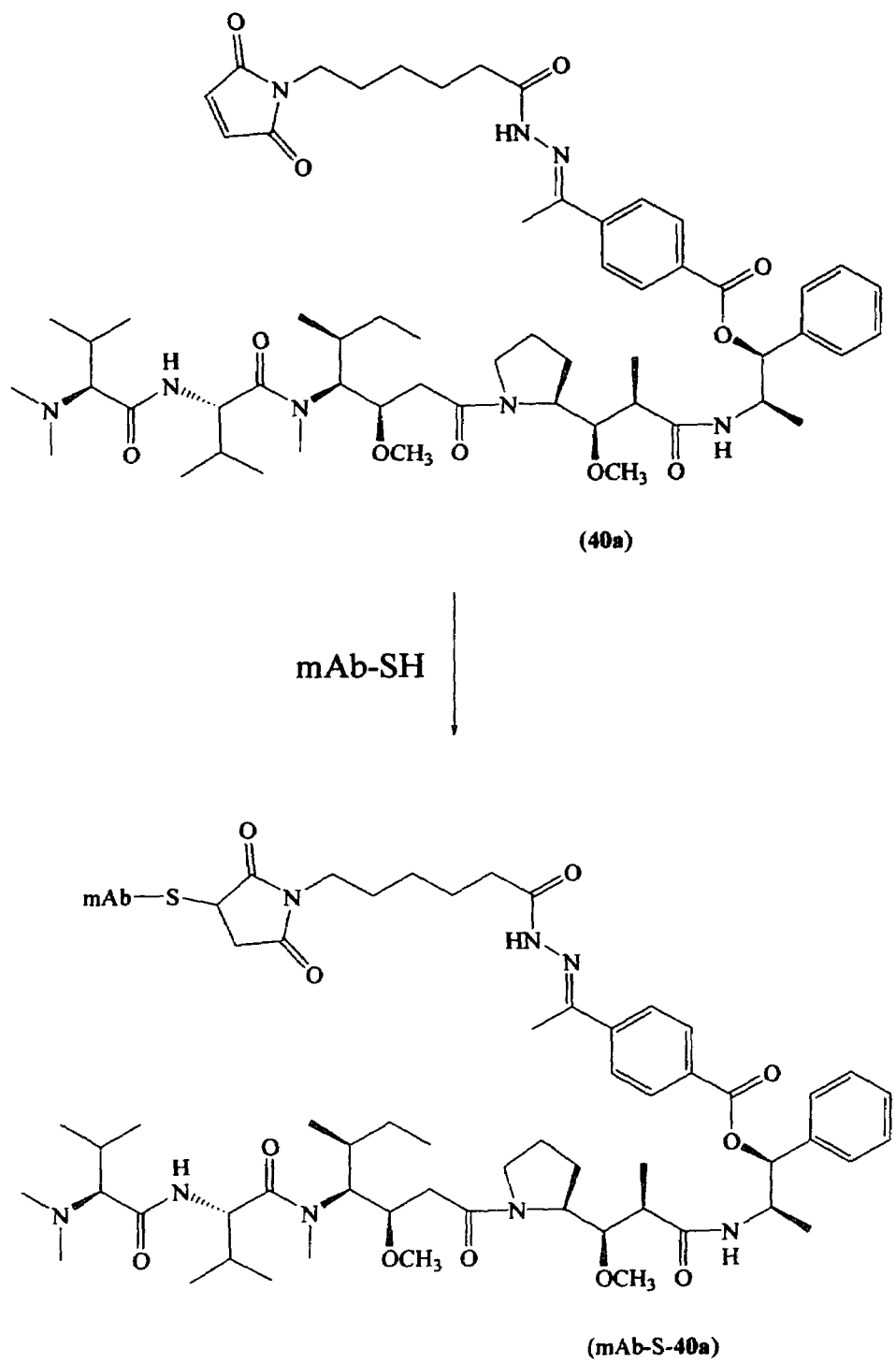
Figure 12:
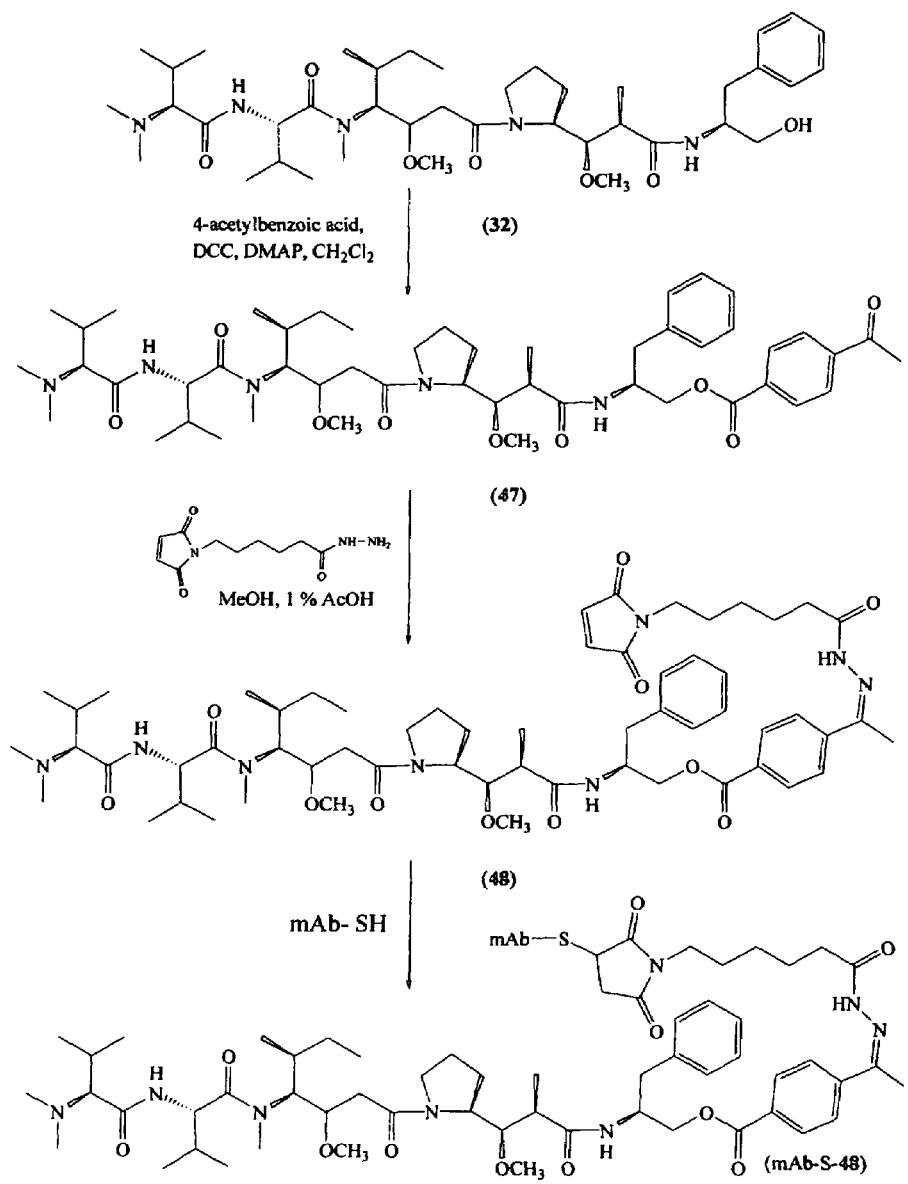
Figure 13:
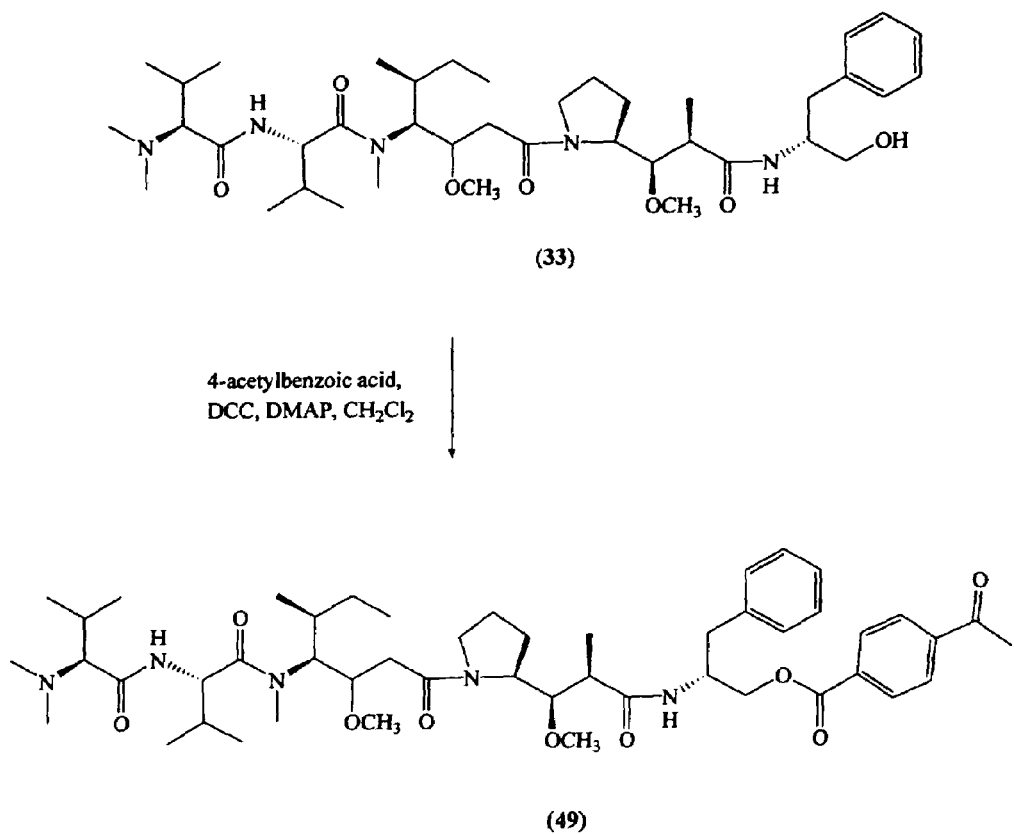
FIG. 13 shows the synthetic scheme used for the preparation of compound 49.
Figure 14:
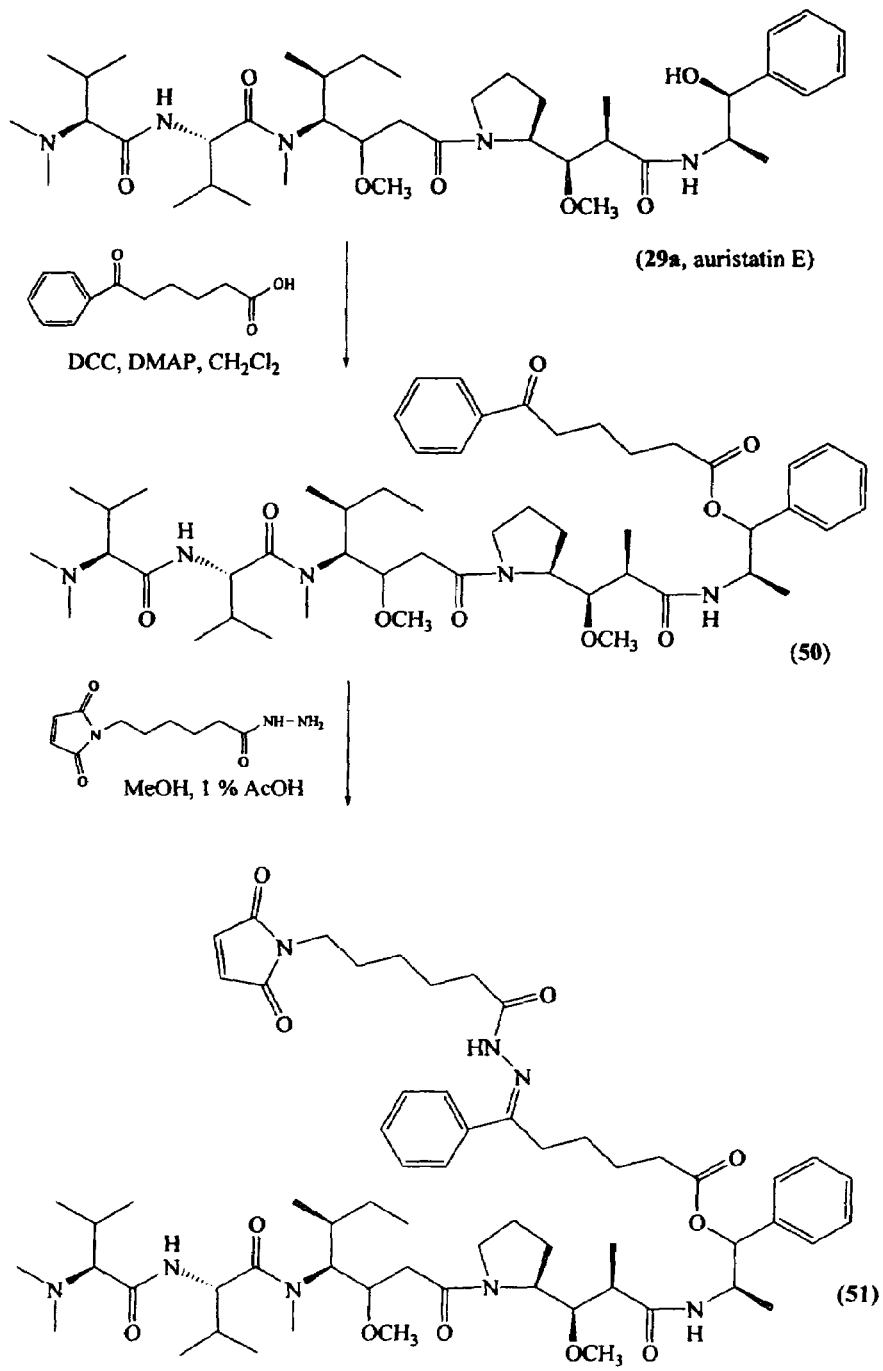
FIG. 14 shows a synthetic scheme for conjugating a pentapeptide to a heterobifunctional linker to provide drug-reactive linker conjugate 51.
Figure 15:
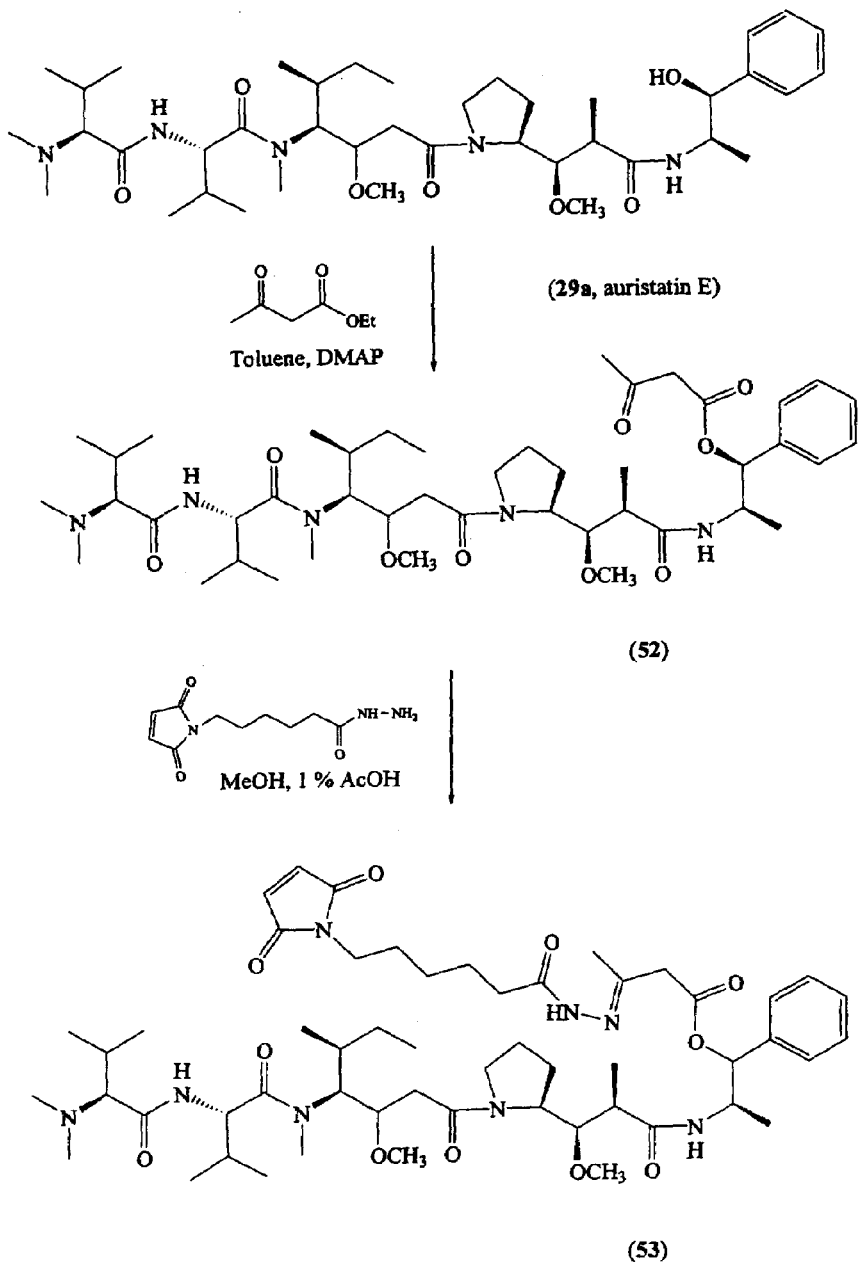
FIG. 15 shows the synthetic scheme used for the preparation of compound 53.

The chemistry described in Examples 1–4 is illustrated in the schemes shown in FIG. 1–3. The chemistry described in Examples 5 and 6 is illustrated in the scheme shown in FIG. 4. The chemistry described in Example 7 is illustrated in the scheme shown in FIG. 5. The chemistry described in Example 8 to prepare compound 36 is illustrated in the scheme shown in FIG. 6, while the conjugation of compound 36 to an antibody is illustrated in FIG. 10. The chemistry described in Example 9 to prepare compounds 38 is illustrated in the scheme shown in FIG. 7. Chemistries to make compounds 40a and 40b, as described in Examples 10 and 11, are shown in FIG. 8, while the conjugation of 40a to an antibody is illustrated in FIG. 11. The preparation of drug-linker-mAb 42 as described in Example 12 is illustrated in the scheme shown in FIG. 9. The reaction of pentapeptide 47 with a heterobifunctional linker as described in Example 13 is illustrated in the scheme of FIG. 12, where this scheme also shows the formation of the drug-linker-antibody conjugate mAb-S-48. The scheme of FIG. 13 shows the preparation of the pentapeptide 49 as described in Example 14. The synthetic descriptions provided in Examples 15, 16, 17 and 18 are illustrated in the schemes provided in FIGS. 14, 15, 16 and 17, respectively.

Coupling Procedure A: Peptide Synthesis Using DEPC

To a cooled (ice bath) solution of [2S-[2R*($\alpha$S*,$\beta$S*)]]-1-[(1,1-dimethylethoxy) carbonyl]-$\beta$-methoxy-$\alpha$-methyl-2-pyrrolidinepropanoic acid (t-Boc-dolaproine, 20) 0.27 g, 0.94 mmol) in anhydrous $CH_2Cl_2$ (10 mL) is added an identified amine (1.03 mmol, 1.1 eq.) followed by triethylamine (0.40 mL, 2.8 mmol, 3.0 eq.) and DEPC (0.17 mL, 90%, 1.03 mmol, 1.1 eq.). The resulting solution is stirred under argon for 12 hours. The solvent is removed under reduced pressure at room temperature, and the residue is chromatographed (silica gel column using 4:1 hexanes-acetone as eluent). After the evaporation of solvent from the fractions selected according to TLC analysis, the residue is dried under vacuum overnight to afford the amide.

Coupling Procedure B: Peptide Synthesis Using PyBrop

The amino acid (1.0 eq.) containing a carboxyl protecting group, if necessary, was dissolved in anhydrous $CH_2Cl_2$ followed by the addition of diisopropylethylamine (1.5 eq.). Fmoc-, Z-, or dimethyl amino acid/pepide (1.1 eq.) was added as a solid in one portion and the dissolved mixture had added PyBrop (1.2 eq.). The reaction was monitored by TLC or HPLC.

General Procedure C: Pentapeptide Synthesis

A solution of dipeptide and tripeptide (1 eq. each) in $CH_2Cl_2$ (10 mL) and trufluoroacetic acid (5 mL) is stirred (ice bath under a $N_2$ atmosphere) for two hours. The reaction may be monitored by TLC or, preferably, HPLC. The solvent is removed under reduced pressure and the residue dissolved in toluene. Solvent is again removed in vacuo and the process repeated. The residue is dried under high vacuum for 12 h and then dissolved in dry $CH_2Cl_2$ followed by the addition of diisopropylethylamine (1.5 eq.). Depending on the residues, the peptides may be coupled using either PyBrop or DEPC (1.2 eq.). The reaction mixture is monitored by either TLC or HPLC.

General Procedure D: Z-removal Via Hydrogenolysis

Using a large, heavy-walled flask, a solution of Z-protected amino acid or peptide was dissolved in ethanol. 10% palladium on carbon was added (1% w/w peptide) and the mixture was introduced to $H_2$. Reaction progress was monitored by HPLC and typically found to be complete within 1–2 h. The flask contents are filtered through a pre-washed pad of celite and then the celite is washed with methanol. The eluent solution is evaporated to an oil, dissolved in toluene, and re-evaporated.

General Procedure E: Fmoc-removal Using Diethylamine

The Fmoc-containing compound is dissolved in $CH_2Cl_2$ to which an equal amount of diethylamine is added. Reaction progress is monitored by TLC (or HPLC) and is usually complete within 2 h. Solvents are removed in vacuo and the residue taken up in toluene and concentrated again. The residue is dried under high vacuum for at least 1 h.

General Procedure F: Hydrazone Formation

Hydrazone formation is performed in anhydrous MeOH, 0.1% AcOH (typically 1 mL per 10 mg of a drug) at room temperature. Time of the reaction (6 h-5 days) and an amount of a hydrazide (2–30 eq.) may be varied depending on the specific ketone. The reaction progress is monitored by $C_{18}$ RP-HPLC. Typically, a newly formed acylhydrazone has lower retention time compared to the parent ketone. After the reaction is complete, DMSO (1–2 mL) is added to the reaction mixture and methanol is removed under reduced pressure. The residue is directly loaded onto a $C_{18}$ RP column for preparative HPLC purification (Varian Dynamax column, 5µ, 100 Å, linear gradient of MeCN in 100 mM TEAA buffer, pH 7.0, from 10 to 95% at flow rate 4 mL/min). The appropriate fractions are concentrated under reduced pressure, co-evaporated with acetonitrile (4×25 mL), and finally dried in deep vacuum for 2 days.

Example 1

Preparation of Compound 29a

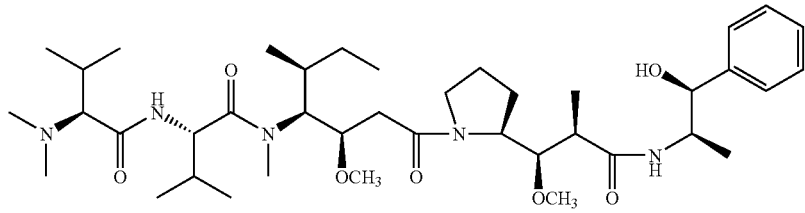

Preparation of Compound 14a

Compound 14a was prepared by reacting compounds 12 and 13a according to coupling procedure B. After concentration of the reaction mixture, the residue was directly injected onto a reverse phase preparative-HPLC column (Varian Dynamax column 21.4 mm×25 cm, 5μ, 100 Å, using an isocratic run of 25% aqueous MeCN at 20 mL/min) in order to remove the unwanted diastereomer. The pure fractions were concentrated to give the product as a clear oil. Yield 14a: 0.67 g (55%); ES-MS m/z 493.4 [M+H]+; UV λ$_{max}$ 215, 256 nm.

Preparation of Compound 15a

Compound 14a was treated according to deprotection procedure D to provide compound 15a.

Preparation of Compound 18a

Compounds 15a and 16 were coupled and characterized as described in Pettit et. al. *J. Chem. Soc. Perk I*, 1996, 859.

Preparation of [(2S)-2-[(1R,2R)-3-[[(1R,2S)-2-hydroxy-1-methyl-2-phenylethyl]amino]-1-methoxy-2-methyl-3-oxopropyl]-pyrrolidine-1-carboxylic acid-tert-butyl ester (25)

t-Boc-dolaproine 20 and (1S,2R)-norephedrine 21 were combined in the presence of DEPC and triethylamine according to General procedure A (see also U.S. Pat. No. 5,635,483 to Pettit et al.) to provide compound 25.

Preparation of N,N-dimethyl-L-valyl-N-[(1S,2R)-4-[(2S)-2-[(1R,2R)-3-[[(1R,2S)-2-hydroxy-1-methyl-2-phenylethyl] amino]-1-methoxy-2-methyl-3-oxopropyl]-1-pyrrolidinyl]-2-methoxy-1-[(1S)-1-methylpropyl]-4-oxobutyl]-N-methyl-L-valinamide, (29a, Auristatin E).

Compound 18a and 25 were combined in the presence of trifluoroacetic acid in methylene chloride (1:1), followed by treatment with DEPC and triethylamine, to provide compound 29a using procedure C. The synthesis of this compound is also reported in U.S. Pat. No. 5,635,483, and Pettit et al., *Anti-Cancer Drug Des.* 1998, 243.

Example 2

Preparation of Compound 29b

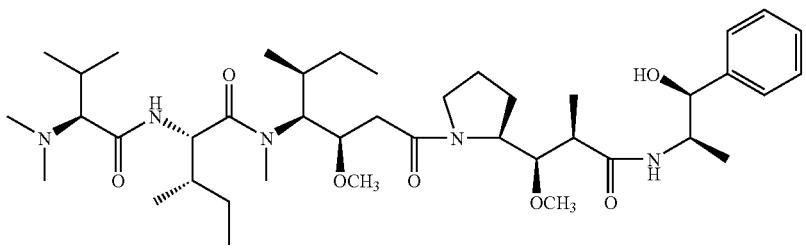

Preparation of Compound 14b

According to coupling procedure B, this peptide was prepared using compounds 12 and 13b. After concentration of the reaction mixture, the residue was purified by C$_{18}$ preparative-HPLC (Varian Dynamax column 21.4 mm×25 cm, 5μ, 100 Å, using an isocratic run of 75% aqueous MeCN at 20 mL/min) in order to remove the unwanted diastereomer. The pure fractions were concentrated to a clear oil. Yield 14b: 0.67 g (55%); R$_f$ 0.32 (4:1 hexanes-acetone); UV λ$_{max}$ 215, 256 nm; $^1$H NMR (CDCl$_3$) δ 7.14–7.40 (5H, m), 6.19 (1H, d, J=9.3 Hz), 5.09 (2H, s), 4.53 (1H, dd, J=6.6, 9.3 Hz), 3.34 (3H, s), 2.97 (3H, s), 2.25–2.50 (2H, m), 1.50–1.78 (3H, m), 1.46(9H, s), 0.99 (3H, d, J=6.9 Hz), 0.96 (3H, d, J=6.9 Hz), 0.89 (3H, t, J=6.9 Hz), 0.83 (3H, t, J=7.2 Hz).

Preparation of Compound 15b

Compound 14b was treated according to deprotection procedure D to provide compound 15b.

Preparation of Compound 18b

Compounds 15b and 16 were combined using procedure A to provide compound 18b: Yield 18b: 0.19 g (82%); ES-MS m/z 500.5 [M+H]+; R$_f$ 0.12 (4:1 hexanes-acetone); UV λ$_{max}$ 215 nm.

Preparation of N,N-dimethyl-L-valyl-N-[(1S,2R)-4-[(2S)-2-[(1R,2R)-3-[[(1R,2S)-2-hydroxy-1-methyl-2-phenylethyl] amino]-1-methoxy-2-methyl-3-oxopropyl]-1-pyrrolidinyl]-2-methoxy-1-[(1S)-1-methylpropyl]-4-oxobutyl]-N-methyl-L-isoleucinamide, (29b)

Following general procedure C, compounds 18b and 25 were combined in the presence of trifluoroacetic acid in methylene chloride, followed by treatment with DEPC and triethylamine. The reaction mixture was purified by preparative-HPLC (C$_{18}$-RP Varian Dynamax column, 5μ, 100 Å, linear gradient of MeCN in 100 mM aqueous triethylammonium carbonate from 10 to 100% in 40 min followed by 20 min at 0% buffer, at flow rate 20 mL/min). The product was isolated as an off-white solid after concentration of the desired HPLC fractions. Yield 29b: 85 mg (60%); ES-MS m/z 746.5 [M+H]$^+$; UV $\lambda_{max}$ 215 nm.

Example 3

Preparation of Compound 31a amino]-1-methoxy-2-methyl-3-oxopropyl]-1-pyrrolidinyl]-2-methoxy-1-[(1S)-1-methylpropyl]-4-oxobutyl]-N-methyl-L-valinamide, (31a)

The Fmoc-protected peptide was treated with diethylamine according to deprotection procedure E. A complete reaction was observed by HPLC after 12 h. The reaction mixture was concentrated to an oil and purified by preparative-HPLC (C$_{18}$-RP Varian Dynamax column, 5μ, 100 Å, linear gradient of MeCN in water 25 to 70% in 5 min followed by 30 min at 70%, at a flow rate of 20 mL/min). The desired fractions were pooled and concentrated to give an off-white solid. Yield 31a: 37 mg (38%); ES-MS m/z 718.7 [M+H]$^+$; UV $\lambda_{max}$ 215 nm.

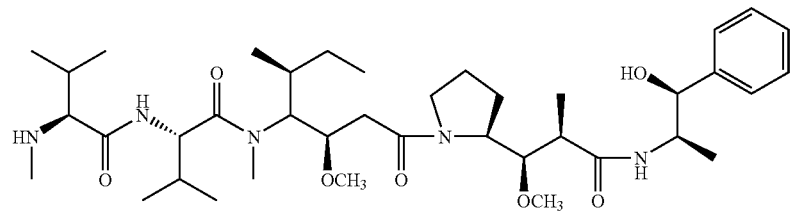

Example 4

Preparation of Compound 31b

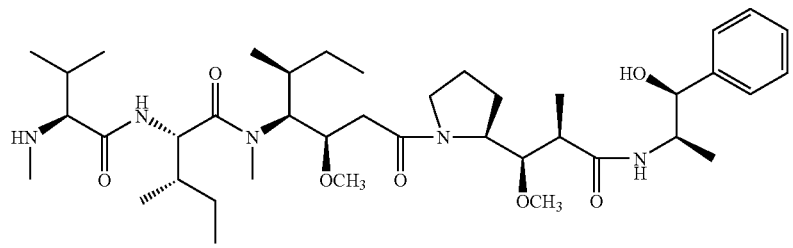

Preparation of Compound 19a

Compounds 15a and 17 were combined using procedure A to provide compound 19a: 107 mg (50%); ES-MS m/z 694.7 [M+H]$^+$; R$_f$ 0.64 (1:1 hexanes-EtOAc); UV $\lambda_{max}$ 215, 265 nm.

Preparation of Compound 30a

Following general procedure C, compounds 19a and 25 (prepared as described in Example 1) were combined in the presence of trifluoroacetic acid in methylene chloride, followed by treatment with DEPC and triethylamine. The reaction mixture was monitored by HPLC and after 4 h water was added and the layers separated. After drying (MgSO$_4$), the contents were filtered and solvent removed to give compound 30a that was used in the next step without further purification. Yield 30a: 127 mg (91%); ES-MS m/z 940.9 [M+H]$^+$.

Preparation of N-methyl-L-valyl-N-[(1S,2R)-4-[(2S)-2-[(1R,2R)-3-[[(1R,2S)-2-hydroxy-1-methyl-2-phenylethyl]

Preparation of Compound 19b

Compounds 15b and 17 were combined using procedure A to provide compound 19b. Yield 19b: 0.50 g (73%); UV $\lambda_{max}$ 215, 265 nm.

Preparation of Compound 30b

Following general procedure C, compounds 19b and 25 (prepared as described in Example 1) were combined in the presence of trifluoroacetic acid in methylene chloride, followed by treatment with DEPC and triethylamine. The reaction mixture was purified by preparative-HPLC (C$_{18}$-RP Varian Dynamax column, 5μ, 100 Å, linear gradient of MeCN in water 25 to 70% in 5 min followed by 30 min at 70%, at a flow rate of 20 mL/min). The product was isolated as an off-white solid after concentration of the desired HPLC fractions. Yield 30b: 64 mg (53%); ES-MS m/z 955.2 [M+H]$^+$; UV $\lambda_{max}$ 215, 265 nm.

Preparation of N-methyl-L-valyl-N-[(1S,2R)-4-[(2S)-2-[(1R,2R)-3-[[(1R,2S)-2hydroxy-1-methyl-2-phenylethyl]

amino]-1-methoxy-2-methyl-3-oxopropyl]-1-pyrrolidinyl]-2-methoxy-1-[(1S)-1-methylpropyl]-4-oxobutyl]-N-methyl-L-valinamide, (31b)

The Fmoc-protected peptide 30b was treated with diethylamine according to deprotection procedure E. A complete reaction was observed by HPLC after 2 h. The reaction mixture was concentrated to an oil. Excess ether was added resulting in a white precipitate and the contents were cooled to 0° C. for 3 h. The product was filtered and the solid dried under high vacuum. Yield 31b: 47 mg (95%); ES-MS m/z 732.8 [M+H]$^+$; UV $\lambda_{max}$ 215 nm.

Example 5

Preparation of Compound 32

[(2S)-2-[(1R,2R)-3-[[(1R)-hydroxymethyl-2-phenylethyl]amino]-1-methoxy-2-methyl-3-oxopropyl]-pyrrolidine-1-carboxylic acid-tert-butyl ester (27)

The dipeptide 27 was synthesized from t-Boc-dolaproine (20) and (R)-(+)-2-amino-3-phenyl-1-propanol (D-phenylalaminol, 23) according to General procedure A. Yield 27: 0.53 g (58%); ES-MS m/z 421.0 [M+H]$^+$; $R_f$ 0.24 (100% EtOAc); UV $\lambda_{max}$ 215, 256 nm. $^1$H NMR (CDCl$_3$) δ 7.14–7.40 (5H, m), 6.19 (0.5H, d, J=5.4 Hz), 5.75 (0.5H, d, J=5.4 Hz), 4.10–4.23 (1H, m), 3.38 (3H, s), 3.10–3.85 (4H, m), 2.82–2.96 (2H, m), 2.10–2.36 (2H, m), 1.66–1.87 (4H, m), 1.47 (9H, bs), 1.16 (1.5H, d, J=6.6 Hz), 1.08 (1.5H, d, J=5.7 Hz).

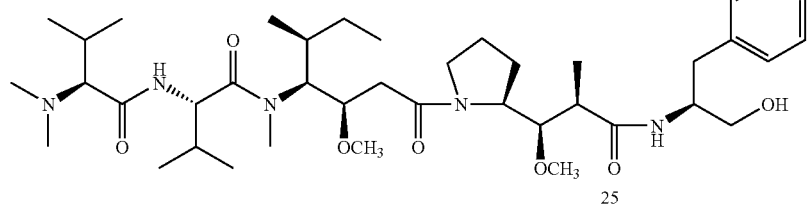

Compound 33

Following general procedure C, compounds 27 (42 mg, 0.1 mmol, 1 eq.) and 18a (65 mg, 0.13 mmol, 1.3 eq.) were combined in the presence of trifluoroacetic acid in methylene chloride, followed by treatment with DEPC and diisopropylethylamine. The reaction mixture was purified by preparative-HPLC (C$_{18}$-RP Varian Dynamax column, 5μ, 100 Å, linear gradient of MeCN in water 25 to 70% in 5 min followed by 30 min at 70%, at a flow rate of 20 mL/min). The product was isolated as an off-white solid after concentration of the desired HPLC fractions. Yield 33: 34 mg (46%); ES-MS m/z 732.1 [M+H]$^+$; UV $\lambda_{max}$ 215, 265 nm.

Preparation of [(2S)-2-[(1R,2R)-3-[[(1S)-hydroxymethyl-2-phenylethyl]amino]-1-methoxy-2-methyl-3-oxopropyl]-pyrrolidine-1-carboxylic acid-tert-butyl ester (26)

The dipeptide 26 was synthesized from t-Boc-dolaproine (20) and (S)-(–)-2-amino-3-phenyl-1-propanol (L-phenylalaminol, 22) according to General procedure A. Yield 26: 0.50 g (55%); ES-MS m/z 421.0 [M+H]$^+$; $R_f$ 0.24 (100% EtOAc); UV $\lambda_{max}$ 215, 256 nm. $^1$H NMR (CDCl$_3$) δ 7.14–7.40 (5H, m), 6.19 (1H, d, J=7.8 Hz), 4.11–4.28 (1H, m), 3.44 (3H, s), 3.20–3.84 (5H, m), 2.80–3.05 (2H, m), 2.20–2.38 (2H, m), 1.65–1.98 (4H, m), 1.48 (9H, s), 1.16 (3H, d, J=5.7 Hz).

Preparation of Compound 32

Following general procedure C, compounds 26 (42 mg, 0.1 mmol, 1 eq.) and 18a (65 mg, 0.13 mmol, 1.3 eq.) were combined in the presence of trifluoroacetic acid in methylene chloride, followed by treatment with DEPC and diisopropylethylamine. The reaction mixture was purified by preparative-HPLC (C$_{18}$-RP Varian Dynamax column, 5μ, 100 Å, linear gradient of MeCN in water 25 to 70% in 5 min followed by 30 min at 70%, at a flow rate of 20 mL/min). The product was isolated as an off-white solid after concentration of the desired HPLC fractions. Yield 32: 60 mg (80%); ES-MS m/z 732.2 [M+H]$^+$; UV $\lambda_{max}$ 215, 265 nm.

Example 6

Preparation of Compound 33

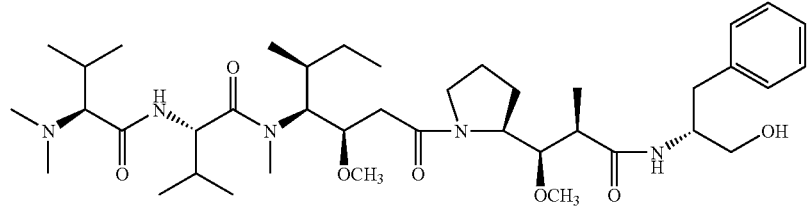

Example 7

Preparation of Compound 34

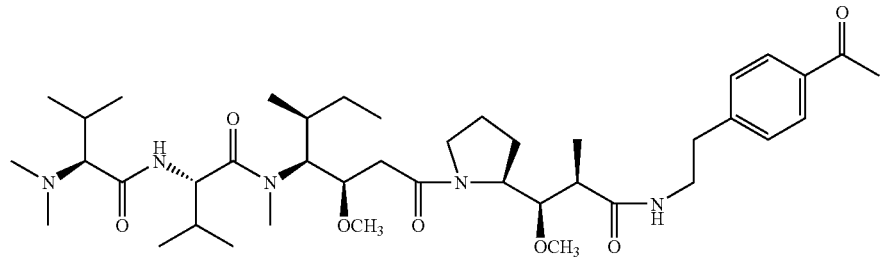

Preparation of Compound 28

Dipeptide 28 is prepared by reacting Boc-dolaproine 20 and p-acetylphenethylamine (U.S. Pat. No. 3,445,518, 1969) according to coupling procedure B. After concentration of the reaction mixture, the residue is purified by reverse phase preparative-HPLC or via $SiO_2$ chromatography.

Preparation of N,N-dimethyl-L-valyl-N-[(1S,2R)-4-[(2S)-2-[(1R,2R)-3-[[(4-acetylphenyl)ethyl]amino]-1-methoxy-2-methyl-3-oxopropyl]-1-pyrrolidinyl]-2-methoxy-1-[(1S)-1-methylpropyl]-4-oxobutyl]-N-methyl-L-valinamide, (34)

Dipeptide 28 and tripeptide 18a are combined in the presence of trifluoroacetic acid in methylene chloride, following a coupling reaction with DEPC and triethylamine as described in general procedure C. The reaction mixture is purified under usual preparative-HPLC measures as previously described for other peptide compounds.

Example 8

Preparation of Compound 36

Preparation of N,N-dimethyl-L-valyl-N-[(1S,2R)-4-[(2S)-2-[(1R,2R)-3-[[(1R)-2-oxo-1-methyl-2-phenylethyl]amino]-1-methoxy-2-methyl-3-oxopropyl]-1-pyrrolidinyl]-2-methoxy-1-[(1S)-1-methylpropyl]-4-oxobutyl]-N-methyl-L-valinamide (35)

Pyridinium chlorochromate (PCC) (13.6 mg, 0.06 mmol, 4.5 eq.) was added to a solution of Auristatin E (29a) (10 mg, 0.014 mmol, 1 eq.) in $CH_2Cl_2$ (2 mL) and pyridine (50 µL). The reaction mixture was stirred at room temperature for 3 h. HPLC analysis of the reaction mixture showed complete conversion of the 10.2 min peak into a new 11.3 min peak with different UV spectrum (max 245 nm, shoulder 280 nm). The product was purified by flash chromatography on a silica gel column (120×12 mm) in a step gradient of MeOH in $CH_2Cl_2$ from 0 to 10%. After concentration in vacuum, the residue was triturated with hexane to give white solid. Yield 35: 6.4 mg (64%); $R_f$ 0.3 ($CH_2Cl_2$/MeOH, 10/1); UV $\lambda_{max}$ 215, 245 nm. HRMS m/z: found 730.5119 $[M+H]^+$. $C_{40}H_{68}N_5O_7$ requires 730.5108.

Preparation of Hydrazone 36

Compound 36 was prepared from compound 35 by reaction with 30 eq. of maleimidocaproylhydrazide for 3 days according to General Procedure F. Yield 36: 2.4 mg (43%) of colorless glass; UV $\lambda_{max}$ 215, 240 (shoulder) nm. HRMS m/z: found 937.6131 $[M+H]^+$. $C_{50}H_{81}N_8O_9$ requires 937.6127.

Example 9

Preparation of Compound 38

Preparation of Levulinic Ester of Auristatin E (37)

Levulinic acid (2.5 µL, 0.025 mmol, 5 eq.) was added to a solution of auristatin E (29a, 3.6 mg, 0.005 mmol, 1 eq.) in anhydrous $CH_2Cl_2$ (1 ml), followed by DCC (5 mg, 0.025 mmol, 5 eq.) and DMAP (1 mg, cat). After reacting for overnight at room temperature, analysis by $C_{18}$ RP-HPLC revealed formation of a new, more hydrophobic product. Precipitated DCU was filtered off. The resulting keto ester was isolated using preparative chromatography on silica gel in a step gradient of MeOH in $CH_2Cl_2$ from 0 to 10%. Yield 37: 3.3 mg (80.5%) of colorless glass; $R_f$ 0.35 ($CH_2Cl_2$/MeOH, 10/1); ES-MS m/z 830 $[M+H]^+$; UV $\lambda_{max}$ 215 nm.

Preparation of Hydrazone 38

Compound 38 was prepared from compound 37 and maleimidocaproylhydrazide (2 eq.) according to General Procedure F, reaction time—6 h. Yield 38: 1.3 mg (46%) of white solid, ES-MS m/z 1037 $[M+H]^+$. UV $\lambda_{max}$ 215 nm.

Example 10

Preparation of Compound 40a

Preparation of 4-acetyl-benzoic Ester of Auristatin E (39a)

4-Acetylbenzoic acid (23.5 mg, 0.14 mmol, 2 eq.) was added to a solution of auristatin E (29a, 50 mg, 0.07 mmol, 1 eq.) in anhydrous $CH_2Cl_2$ (5 ml), followed by DCC (30 mg, 0.14 mmol, 2 eq.) and DMAP (5 mg, cat). After reacting overnight at room temperature, analysis by $C_{18}$ RP-HPLC revealed formation of a new, more hydrophobic product. Precipitated DCU was filtered off. The resulting keto ester was isolated using preparative chromatography on silica gel in a step gradient of MeOH in $CH_2Cl_2$ from 0 to 10%. The product was eluted with 5% MeOH in $CH_2Cl_2$. Yield 39a: 57 mg (90%) of white solid; $R_f$ 0.43 ($CH_2Cl_2$/MeOH, 10/1); UV $\lambda_{max}$ 215, 250 nm. HRMS m/z: found 878.5669 $[M+H]^+$. $C_{49}H_{76}N_5O_9$ requires 878.5643. Anal. calcd for $C_{49}H_{75}N_5O_9 \times H_2O$: C, 65.67; H, 8.66; N, 7.81. Found: C, 66.05; H, 8.61; N, 7.80.

Preparation of Hydrazone 40a

Compound 40a was prepared from compound 39a and maleimidocaproylhydrazide (3 eq.) according to General Procedure F, reaction time—12 h. Yield 40a: 3 mg (65%) of solid; UV $\lambda_{max}$ 215, 295 nm. HRMS m/z: found 1085.6665 [M+H]$^+$. $C_{59}H_{89}N_8O_1$, requires 1085.6651. Anal. calcd for $C_{59}H_{88}N_8O_{11}\times H_2O$: C, 64.22; H, 8.22; N, 10.16. Found: C, 64.27; H, 8.21; N, 9.92.

Example 11

Preparation of Compound 40b

Preparation of 4-acetyl-benzoic ester of N,N-dimethyl-L-valyl-N-[(1S,2R)-4-[(2S)-2-[(1R,2R)-3-[[(1R,2S)-2-hydroxy-1-methyl-2-phenylethyl]amino]-1-methoxy-2-methyl-3-oxopropyl]-1-pyrrolidinyl]-2-methoxy-1-[(1S)-1-methylpropyl]-4-oxobutyl]-N-methyl-L-isoleucinamide, (39b)

Compound 39b was prepared from compound 29b by reaction with 4-acetobenzoic acid in the presence of DCC, DMAP in $CH_2Cl_2$ as described in the Example 10. Yield 39b: 10.7 mg (80%) of white solid; $R_f$ 0.37 ($CH_2Cl_2$/MeOH, 10/1); UV $\lambda_{max}$ 215, 250 nm. HRMS m/z: found 892.5775 [M+H]$^+$. $C_{50}H_{78}N_5O_9$ requires 892.5800.

Preparation of Hydrazone (40b)

Compound 40b was prepared from compound 39b and maleimidocaproylhydrazide (5 eq.) according to General Procedure F, reaction time—18 h. Yield 40b: 4.8 mg (50%) of solid; ES-MS m/z: 1099 [M+H]$^+$; UV $\lambda_{max}$ 215, 295 nm.

Example 12

Preparation of Compound 42

Preparation of Compound 42

To a solution of 39a (5 mg, 0.0056 mmol) in DMSO (100 µL) anhydrous MeOH (0.9 mL) was added, followed by 1% AcOH/MeOH (10 µL). 3-Bromoacetamido)propyonyl hydrazide (41) (0.025 mmol, 4.5 eq.) was added to the solution. The reaction was left at room temperature for 24 h. $C_{18}$-RP HPLC analysis revealed the formation of a new compound with a lower retention time. DMSO (1 mL) was added to the reaction mixture and methanol was removed under reduced pressure. The residue was directly loaded onto a $C_{18}$-RP column for preparative HPLC purification (Varian Dynamax column, 5µ, 100 Å, linear gradient of MeCN in 100 mM TEAA buffer, pH 7.0, from 10 to 95% at flow rate 4 mL/min). The appropriate fractions are concentrated under reduced pressure, co-evaporated with acetonitrile (4×25 mL), and finally dried in deep vacuum. Yield 42: 4.0 mg (66%) of solid; ES-MS m/z: 1084 [M+H]$^+$, 1086; UV $\lambda_{max}$ 215, 295 nm.

Example 13

Preparation of Compound 48

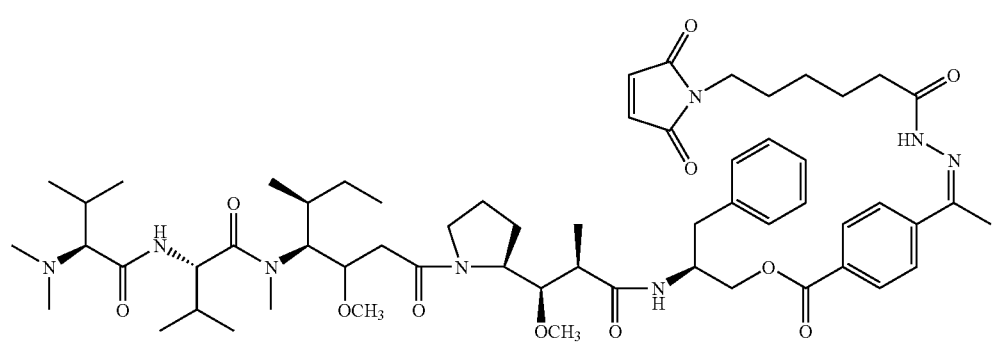

Compound 47

Compound 47, shown below, was prepared from compound 32 (8.8 mg, 0.012 mmol) by reaction with 4-acetobenzoic acid in the presence of DCC, DMAP in $CH_2Cl_2$ as described in the Example 10. Yield 47: 7.3 mg (70%) of white solid; $R_f$ 0.4 ($CH_2Cl_2$/MeOH, 10/1); ES-MS m/z 878.9 [M+H]$^+$; UV $\lambda_{max}$ 215, 250 nm.

Compound 47

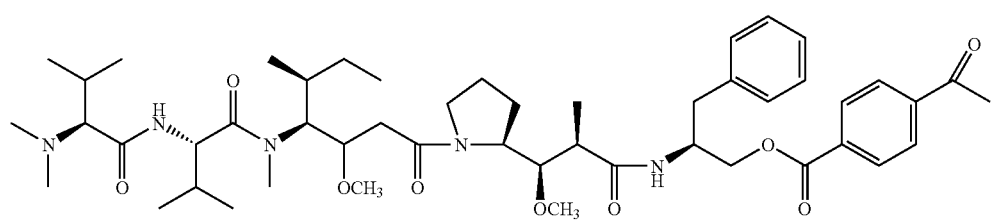

Preparation of Hydrazone 48

Compound 48 was prepared from compound 47 (6.4 mg, 0.007 mmol) and maleimidocaproylhydrazide (4 eq.) according to General Procedure F, reaction time—4 h. Yield 48: 4.3 mg (57%) of colorless glass; ES-MS m/z: 1085.7 $[M+H]^+$; UV $\lambda_{max}$ 215, 294 nm.

Example 14

Preparation of Compound 49

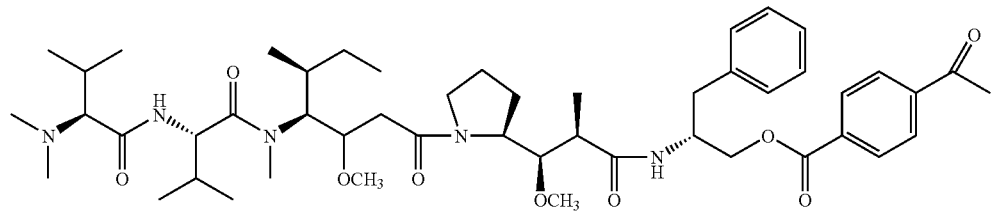

Compound 49 (structure shown above) was prepared from compound 33 (8.0 mg, 0.01 mmol) by reaction with 4-acetobenzoic acid in the presence of DCC, DMAP in $CH_2Cl_2$ as described in the Example 10. Yield 49: 8.1 mg (92%) of white solid; $R_f$ 0.37 ($CH_2Cl_2$/MeOH, 10/1); UV $\lambda_{max}$ 215, 250 nm. HRMS m/z: found 878.5653 $[M+H]^+$. $C_{49}H_{76}N_5O_9$ requires 878.5643.

Example 15

Preparation of Compound 51

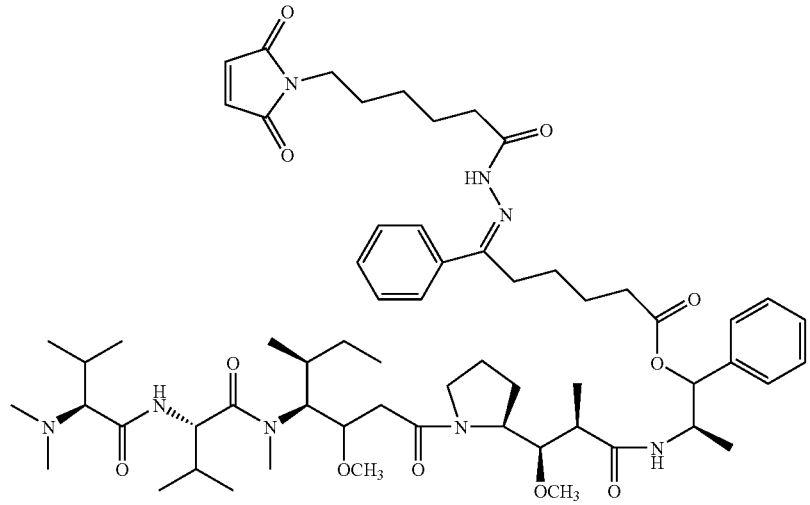

Preparation of 5-benzoylvaleric ester of Auristatin E (50)

Compound 50 (structure shown below) was prepared from auristatin E (29a, 10 mg, 0.014 mmol) by reaction with 5-benzoylvaleric acid in the presence of DCC, DMAP in $CH_2Cl_2$ as described in the Example 10. Yield 50: 10 mg (79%) of pale yellow oil; $R_f$ 0.34 ($CH_2Cl_2$/MeOH, 10/1); UV $\lambda_{max}$ 215 nm. HRMS m/z: found 920.6139 $[M+H]^+$. $C_{52}H_{82}N_5O_9$ requires 920.6113.

Compound 50

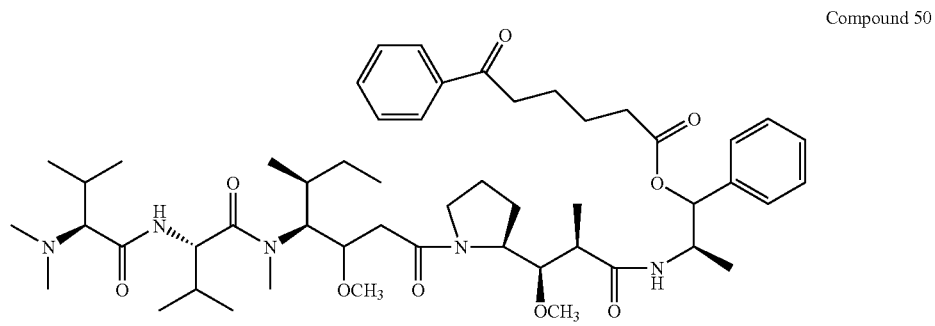

Preparation of Hydrazone 51

Compound 51 was prepared from compound 50 (5 mg, 0.0054 mmol) and maleimidocaproylhydrazide (5 eq.) according to General Procedure F, reaction time—12 h. Yield 51: 3.5 mg (57%) of white solid; UV $\lambda_{max}$ 215, 280 nm. HRMS m/z: found 1127.7132 [M+H]$^+$. $C_{62}H_{95}N_8O_{11}$ requires 1127.7120.

Example 16

Preparation of Compound 53

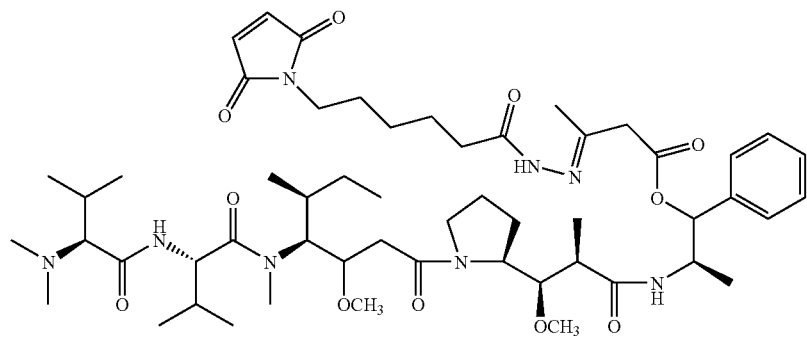

Preparation of Acetoacetic Ester of Auristatin E (52)

A solution of auristatin E (29a, 10 mg, 0.014 mmol, 1 eq.), ethyl acetoacetate (9 μL, 0.07 mmol, 5 eq.), and DMAP (3.5 mg, 0.029 mmol, 2 eq.) in anhydrous toluene (5 mL) was refluxed for 10 h. The reaction mixture was concentrated under reduced pressure to dryness. The residue was re-dissolved in 2 mL of $CH_2Cl_2$ and the product was purified by silica gel flash chromatography in 10% MeOH in $CH_2Cl_2$. Yield 52 (structure shown below): 7 mg (60%) of colorless glass; $R_f$ 0.4 ($CH_2Cl_2$/MeOH, 10/1); ES-MS m/z: 816.9 [M+H]$^+$; UV $\lambda_{max}$ 215 nm.

Compound 52

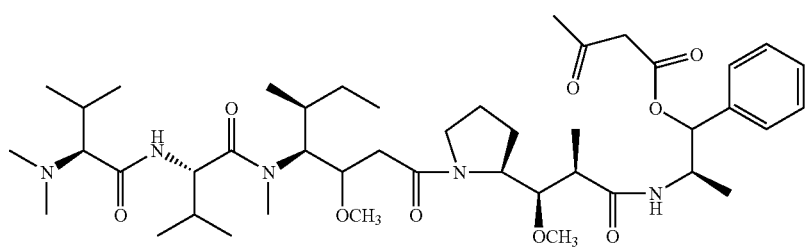

Preparation of Hydrazone 53

Compound 53 was prepared from compound 52 and maleimidocaproylhydrazide (10 eq.) according to General Procedure F, reaction time—12 h. Hydrazone 53 was used for kinetic studies without isolation. UV $\lambda_{max}$ 215 nm.

Example 17

Preparation of Compound 57

Preparation of Boc-Phenylalaminol-p-acetylphenoxy Ether (56)

A solution (S)-(–)-Boc-phenylalaminol (54, 0.50 g, 2.0 mmol, 1.0 eq.), 4-hydroxyacetophenone (55, 0.30 g, 2.2 mmol, 1.1 eq.), and triphenylphosphine (0.80 g, 3.0 mmol, 1.5 mmol), in anhydrous dioxane (20 mL) was cooled to 0° C. Dropwise addition of diisopropylazodicarboxylate (0.62 mL, 3.0 mmol, 1.5 eq.) was performed over a 2 min period and the reaction was monitored by reverse phase-HPLC. After 24 h, solvent was removed in vacuo and the residue purified by preparative-HPLC ($C_{18}$-RP Varian Dynamax column, 5μ, 100 Å, linear gradient of MeCN in water 10 to 100% in 40 min followed by 20 min at 100%, at a flow rate of 20 mL/min). The desired fractions were concentrated to give the product as a white solid. Yield 56: 0.54 g (74%); ES-MS m/z 370.2 [M+H]$^+$; UV $\lambda_{max}$ 215, 275 nm. $^1$H NMR (CDCl$_3$) δ 7.96 (2H, d, J=6.9 Hz), 7.18–7.35 (5H, m), 6.94 (2H, d, J=8.4 Hz), 4.92 (1H, bd, J=8.1 Hz), 4.14–4.28 (1H, m), 3.91–4.02 (2H, m), 2.99–3.04 (2H, m), 2.58 (3H, s), 1.45 (9H, s).

Preparation of Dipeptide 57

A solution of 56 (70 mg, 0.19 mmol, 1.0 eq.) in 10 mL CH$_2$Cl$_2$-TFA (2:1) stood over a N$_2$ atmosphere for 2 h. HPLC indicated a complete reaction. The reaction mixture was concentrated to an oil that was taken up in a minimum amount of dichloromethane and precipitated with hexanes. The white solid was collected and dried under high vacuum for 20 h. The free amine and t-Boc-dolaproine (20) were combined in the presence of DEPC (1.5 eq.) and triethylamine (3.0 eq.) according to General procedure A. After 24 h, solvent was removed in vacuo and the residue purified by preparative-HPLC ($C_{18}$-RP Varian Dynamax column, 5μ, 100 Å, linear gradient of MeCN in water 10 to 100% in 40 min followed by 20 min at 100%, at a flow rate of 20 mL/min). The desired fractions were concentrated to give the product as a white solid. Yield 57: 52 mg (51%); ES-MS m/z 538.9 [M+H]$^+$; UV $\lambda_{max}$ 215, 275 nm. $^1$H NMR (CDCl$_3$) δ 7.92 (2H, d, J=7.2 Hz), 7.18–7.33 (5H, m), 6.94 (2H, d, J=7.5 Hz), 6.69 (½H, bd, J=7.2 Hz), 5.98 (½H, bd, J=7.5 Hz), 4.46–4.57 (1H, m), 3.96–4.08 (2H, m), 3.48–3.88 (3H, m), 3.38 (3H, s), 2.92–3.26 (3H, m), 2.56 (3H, s), 2.23–2.40 (1H, m), 1.55–1.90 (4H, m), 1.49 (4.8H, s), 1.45 (4.2H, s), 1.18 (3H, d, J=6.9 Hz).

Example 18

Preparation of Compound 59

Preparation of Compound 58

Following general procedure C, compounds 57 (25 mg, 0.046 mmol, 1 eq.) and 18a (34 mg, 0.07 mmol, 1.5 eq.) were combined in the presence of trifluoroacetic acid in methylene chloride, followed by treatment with DEPC and diisopropylethylamine. The reaction mixture was separated on silica gel column in a step gradient of MeOH from 0 to 10% in CH$_2$Cl$_2$. The product was eluted by 5% MeOH and after concentration was obtained as a white solid. Yield 58: 33 mg (85%); R$_f$ 0.35 (CH$_2$Cl$_2$/MeOH, 10/1); ES-MS m/z 850.7 [M+H]$^+$; UV $\lambda_{max}$ 215, 271 nm.

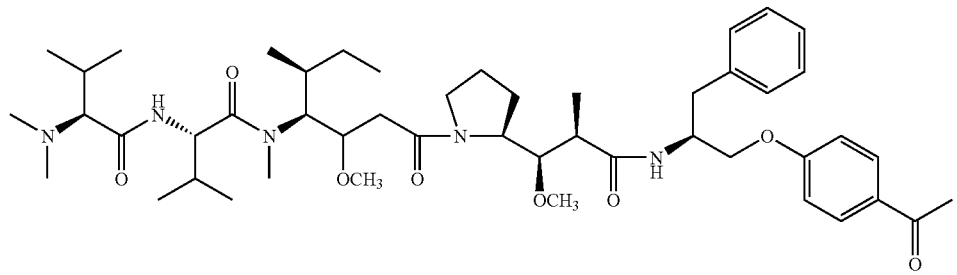

Compound 58

Preparation of Hydrazone 59

Compound 59 was prepared from compound 58 (33 mg, 0.04 mmol) and maleimidocaproylhydrazide (5 eq.) according to General Procedure F, reaction time—17 h. Yield 59: 17.3 mg (40%) of colorless glass; ES-MS m/z: 1057.9 [M+H]$^+$; UV $\lambda_{max}$ 215, 265 nm.

Example 19

Cytotoxicity Study: Compounds 29a and 39a

In vitro cytotoxicity experiments on several cell lines were performed to compare the activities of auristatin E (29a) with the ketoester 39a. The ester proved to be cytotoxic on a wide panel of cell lines, ranging from as cytotoxic as auristatin E (29a) on L2981 cells, to being approximately 17-times less cytotoxic on Daudi Burkitt's lymphoma cells (Table 1).

TABLE 1

CELL LINES USED FOR THE EVALUATION OF MAB-AURISTATIN E CONJUGATES, AND THE RELATIVE CYTOTOXIC EFFECTS OF AURISTATIN E (29a) AND THE KETOESTER DERIVATIVE 39a

| | | Antigen Expression (MFI) | | | IC$_{50}$(nM) | |
|---|---|---|---|---|---|---|
| Cell Line | Tumor Type | LeY | CD40 | CD30 | 29a | 39a |
| L2987 | lung | 620 | 171 | 7 | 1.0 | 0.9 |
| Kato III | gastric | 94 | neg. | neg. | 0.7 | 5 |

TABLE 1-continued

CELL LINES USED FOR THE EVALUATION OF MAB-AURISTATIN E CONJUGATES, AND THE RELATIVE CYTOTOXIC EFFECTS OF AURISTATIN E (29a) AND THE KETOESTER DERIVATIVE 39a

| Cell Line | Tumor Type | Antigen Expression (MFI) | | | $IC_{50}$(nM) | |
|---|---|---|---|---|---|---|
| | | LeY | CD40 | CD30 | 29a | 39a |
| SKBR3 | breast | 2985 | 20 | 88 | 1.5 | 6 |
| AU565 | breast | 869 | 19 | 57 | 1.5 | 6 |
| Daudi | Burkitt's lymphoma | 37 | 72 | neg. | 0.9 | 15 |
| L428 | Hodgkin's lymphoma | 74 | 16 | 76 | 1.5 | 13 |
| L540 | Hodgkin's lymphoma | 99 | 0 | 223 | 1.5 | 16 |
| IM-9 | Multiple myeloma | 132 | 47 | 40 | 3.5 | 50 |
| Karpas | ALCL | 59 | 1 | 246 | 1.2 | 13 |

To obtain the results shown in Table 1, the cells were exposed to drugs for 1–2 hours, and the cytotoxic effects were determined 72 hours later by the incorporation of $^3$H-thymidine into DNA. Antigen expression was determined by flow cytometry and is expressed in terms of mean fluorescence intensity (MFI).

Further studies were undertaken to explore the stability of 39a in human serum, and it was shown that there was no detectable hydrolysis after 120 hours incubation at 37° C. Furthermore, prolonged exposure of 39a to purified esterases from human, rhesus monkey, guinea pig and rabbit livers failed to demonstrate any conversion of 39a to auristatin E (29a). Thus it appears that 39a may not be an auristatin E prodrug, but instead exhibits activity as a benzylic ester.

Example 20

Cytotoxicity Study: Compounds 29a, 39a, 32, 33, 47, 49, 50, 52 and 58

In vitro cytotoxicity experiments were performed to compare the activities of auristatin E (29a) and drugs of this invention. 3396 and Karpas cells were exposed to the drug for 1 and 2 hr respectively. The cells were washed, and cytotoxicity was determined 96 hr later using XTT to measure mitochondrial integrity. The results are shown in Table 2.

TABLE 2

THE RELATIVE CYTOTOXIC EFFECTS OF AURISTATIN E (29a) AND DERIVATIVES

| Cell Line | Tumor Type | $IC_{50}$ (nM) | | | | | | | | |
|---|---|---|---|---|---|---|---|---|---|---|
| | | 29a | 39a | 32 | 33 | 47 | 49 | 50 | 52 | 58 |
| 3396 | breast | 6.0 | 16 | 4.5 | 70 | 0.35 | 34 | 3.0 | 20 | 2.5 |
| Karpas 299 | ALCL | 1.2 | 4 | | | 0.075 | | | | |

Example 21

Structural Effects on Hydrazone Hydrolysis

In order to analyze the structural requirements for efficient hydrazone hydrolysis under mildly acidic conditions, a series of norephedrine derivatives (Table 3) related in structure to the C-terminus of a pentapeptide of the invention were prepared.

TABLE 3

COMPOUNDS TESTED FOR HYDRAZONE HYDROLYSIS KINETICS

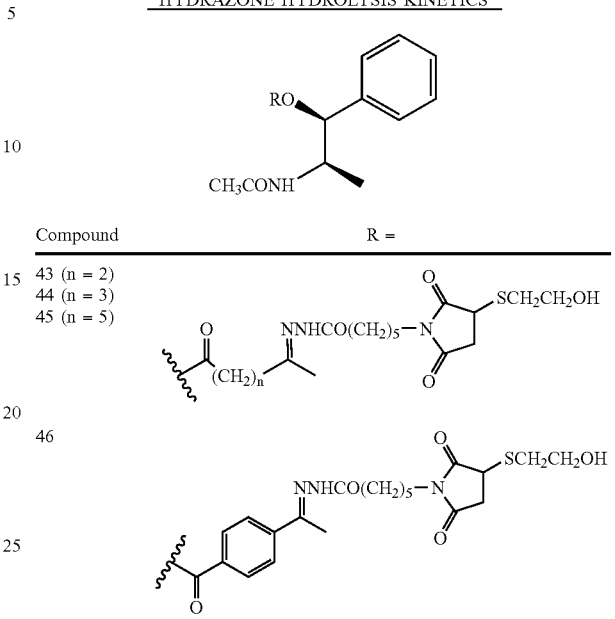

| Compound | R = |
|---|---|
| 43 (n = 2) | |
| 44 (n = 3) | |
| 45 (n = 5) | |
| 46 | |

Condensation of N-acetylnorephedrine with various ketoacids in the presence of DCC led to the formation of the corresponding ketoesters. Upon reaction with maleimidocaproylhydrazide, hydrazones were formed. HPLC was used for stability determination at pH 5 and 7.2 at 37° C. 2-Mercaptoethanol (2 eq.) was added to quench the reactive maleimide functionalities forming compounds 43–46 in situ. The mercaptoethanol adducts 43–45 were unstable at both pH 5 and 7.2 (Table 4). In contrast, the benzylic hydrazone 46 hydrolyzed quite slowly at pH 7.2, but underwent hydrolysis at pH 5 with a half-life of 5 hours. The product formed upon hydrolysis of 46 was the parent ketoester.

TABLE 4

HYDROLYSIS OF THIOETHER-MODIFIED HYDRAZONES OF NOREPHEDRIN AT 37° C.

| Hydrazone | $t_{1/2}$ at pH 5.0 | $t_{1/2}$ at pH 7.2 |
|---|---|---|
| 43 | <2 minutes | 8 hours |
| 44 | <2 minutes | 2 hours |
| 45 | <2 minutes | <10 minutes |
| 46 | 5 hours | 60 hours |

Example 22

Preparation of mAb-Drug Conjugates

A solution of monoclonal antibody (mAb) (5–10 mg/mL) in phosphate buffered saline, pH 7.2, is reduced with dithiothreitol (65 eq.) at 37° C. for 45 minutes. Separation of low molecular weight agents is achieved by size exclusion chromatography on a Sephadex G25 column, and the sulfhydryl content in the mAb is determined using 5,5'-dithiobis (2-nitrobenzoic acid) as described previously (Riddles, P. W., Blakeley, R. L., and Zerner, B. (1979) "Ellman's reagent: 5,5'-dithiobis(2-nitrobenzoic acid)-a reexamination" *Anal. Biochem.* 94, 75–81). There are typically between 6–9 free sulhydryl groups per mAb.

To the reduced mAb is added acetonitrile (12% final vol) followed by drug-(reactive linker) 36, 38, 40a, 40b, 48, 51 or 59 in a 1 mM solution of 9:1 acetonitrile:DMSO so that the final drug concentration is 1.9-fold higher than that of the mAb sulfhydryl groups. After 60 min at room temperature, glutathione (1 mM final concentration) and oxidized glutathione (5 mM final concentration) are added, and the solution is allowed to stand for an additional 10 min. Unbound drug is removed by repeated ultrafiltration (Amicon, YM30 filter) until there is no evidence of low molecular weight agents in the filtrate. The concentrated protein is gel filtered on Sephadex G25, a small portion of polystyrene beads is added to the pooled protein fraction, and the solution is sterile filtered using 0.4 micron filters. The protein concentration is determined at 280 nm ($E_{0.1\%}$ 1.4).

Free drug concentration is determined by reversed-phase chromatography against standard solutions of drug-(reactive linker) standards ($C_{18}$ Varian Dynamax column, 5μ, 100 Å, linear gradient of MeCN in 5 mM ammonium phosphate buffer, pH 7.0, from 10 to 90% in 10 min followed by 90% MeCN for 5 min at flow rate 1 mL/min). Typically, there is less than 0.5% free drug in the purified conjugate preparations. Bound drug is quantified by hydrolyzing the linked drugs from the mAb with 1 volume of pH 1.5 aqueous HCl buffer for 15 minutes at room temperature, neutralizing the solution with borate buffer at pH 8, and analyzing drug concentration using reversed phase HPLC as indicated above. There are typically between 4–7 drugs/mAb.

Example 23

Hydrolysis of Thioether-Modified Linkers and Immunoconjugates

Synthesis of Thioethers of compounds 36, 38, 40a, 40b, 48, 51, 53 and 59

Mercaptoethanol adducts of compounds 36, 38, 40a, 40b, 48, 51, 53 and 59 were prepared in situ by a reaction of the corresponding maleimido hydrazones (0.3 mM in 10% aqueous PBS, 10% DMSO) with 2 eq. of mercaptoethanol for 15 min at room temperature. HPLC analysis ($C_{18}$ Varian Dynamax column, 5μ, 100 Å, linear gradient of MeCN from 10 to 90% in 5 mM ammonium phosphate buffer, pH 7.0, in 10 min, then 90% of MeCN for 5 min at flow rate 1 mL/min) showed new peaks with retention times of 0.3–1 min less then for parent hydrazones. Reaction mixtures were directly used for hydrolysis kinetics.

Kinetics of the Hydrazone Bond Hydrolysis for Thioethers of Compounds 36, 38, 40a, 40b, 48, 51, 53 and 59

Thioethers solutions (0.3 mM in 10% aqueous PBS, 10% DMSO) were adjusted to a final salt concentration of 30 mM with either 100 mM NaOAc, pH 5.0, or 100 mM $Na_2HPO_4$, pH 7.2, then incubated at 37° C. in a temperature controlled autosampler of the HPLC system. Aliquots (10 mL) were taken at timed intervals and the disappearance of starting material was monitored by HPLC at 215 nm ($C_{18}$ Varian Dynamax column, 5μ, 100 Å, linear gradient from 10 to 90% of MeCN in 5 mM ammonium phosphate buffer, pH 7.0, in 10 min, then 90% of MeCN for 5 min at flow rate 1 mL/min). The results were expressed as percents of starting hydrazones. Half-lives of hydrazones were calculated from these curves and are listed in Table 4.

Immunoconjugate Hydrolysis Kinetics

Conjugates (1 mg/mL) in 10% aqueous DMSO, 50 mM buffer (either NaOAc, pH 5.0, or 50 mM $Na_2HPO_4$, pH 7.2) were incubated at 37° C. in a temperature controlled autosampler of the HPLC system. Aliquots (100 μL) were taken at timed intervals and the formation of a drug (ketoester) was monitored by HPLC at 250 nm ($C_{18}$ Varian Dynamax column, 5μ, 100 Å, linear gradient from 10 to 90% of MeCN in 5 mM ammonium phosphate buffer, pH 7.0, in 10 min, then 90% of MeCN for 5 min at flow rate 1 mL/min). Free drug was quantitated by integrating the corresponding peak (positively identified by comparison to a standard). The results were presented as percents of total drug released. Half-lives of immunoconjugates were calculated from these curves and are listed in Table 5.

TABLE 5

HYDROLYSIS OF THIOETHER-MODIFIED LINKERS AND IMMUNOCONJUGATES AT 37° C.

| Conjugate | $t_{1/2}$ at pH 5.0 | $t_{1/2}$ at pH 7.2 |
| --- | --- | --- |
| Thioether of 38 | 4 hours | 9 hours |
| Thioether of 40a | 8 hours | 110 hours |
| Thioether of 48 | 3.5 hours | >50 hours |
| Thioether of 51 | 3 hours | >40 hours |
| Thioether of 53 | 2 hours | <30 hours |
| Thioether of 59 | 4.5 hours | >55 hours |
| BR96-S-36 | 50 hours | >500 hours |
| BR96-S-40a | 15 hours | 250 hours |
| BR96-S-48 | 15 hours | >150 hours |
| BR96-doxorubicin | 3.5 hours | >120 hours |
| AC10-S-48 | 17 hours | >350 hours |

Example 24

Preparation of hBR96-S-42 Conjugate

To 450 μL of PBS, pH 7.2, containing 3.0 mg hBR96 was added 50 μL of 100 mM dithiothreitol (DTT) in water. The mixture was incubated at 37° C. for 30 min. Excess DTT was removed from the reduction reaction by elution through a PD10 column (Pharmacia) with PBS containing 1 mM DTPA. The number of free thiols per antibody was determined to be 8.5, by measuring the protein concentration ($A_{280}$, assuming the absorbance of a 1 mg/mL solution=1.4) and the $A_{412}$ of an aliquot of the protein treated with DTNB, assuming a molar extinction coefficient of 14,150.

The pH of the 1.2 mL reduced antibody solution was raised to 8.7 by the addition of 150 μL 500 mM Na-Borate/ 500 mM NaCl, pH 8.7. A solution containing a 12-fold excess of compound 42 over antibody was prepared in 150 μL DMSO. The solution of compound 42 was added to the reduced antibody solution with vigorous stirring and the reaction mixture incubated at room temperature for about 3 hours. The reaction mixture was quenched by the addition of sufficient 200 mM sodium tetrathionate to make the solution 1 mM.

The quenched reaction mixture was purified by immobilization on an ion exchange matrix, rinsing with a partial organic solvent solution, elution from the matrix and buffer exchange into PBS. Thus, the quenched reaction mixture was diluted to 35 mL in 25 mM Tris, pH 9 ("Eq. Buffer"), then loaded onto an EMD TMAE column equilibrated in Eq. Buffer. The immobilized conjugate was rinsed with a mixture of 20% acetonitrile/80% Eq buffer, then eluted with 0.5 M NaCl/19 mM Tris, pH 9. Fractions were analyzed by size exclusion chromatography and pooled. The eluted conjugate was concentrated by centrifugal ultrafiltration, then eluted through a PD 10 column in PBS, producing 1.2 mL of a 2.0 mg/mL solution (based on $A_{280}$). Elution of conjugate through a $C_{18}$ column indicated that any unconjugated drug was below the detection level (~0.2 μM). Treatment of the conjugate with pH 1.7 buffer for 15 min, followed by $C_{18}$ HPLC analysis indicated that the drug was covalently conjugated to the antibody. Comparison of the HPLC peak area from the hydrolyzed conjugate with an standard curve of 39a determined the level of the drug attached to a given quantity of conjugate; comparison with the antibody concentration determined by $A_{280}$, gave a ratio of 3.2 drug/hBR96. Treatment of H3396 cells with this conjugate inhibited cell growth with an $IC_{50}$ of about 1.5 μg/mL.

Example 25

In Vitro Cytotoxicity Data for mAb-S-36

Figure 18A:
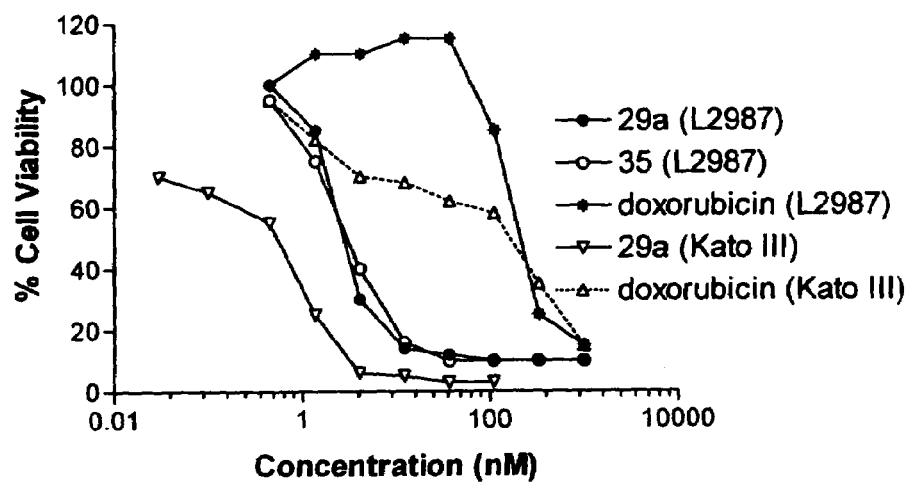
FIGS. 18A, 18B and 18C show the in vitro cytotoxicity of drugs and mAb-drug conjugates on (A) and (B) L2987 human lung adenoma cells, and (A) and (C) Kato III human gastric carcinoma cells.
Figure 18B:
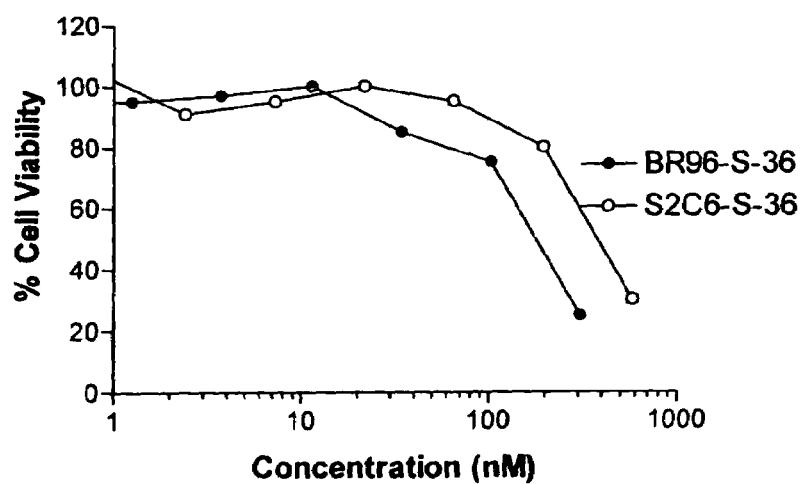
Figure 18C:
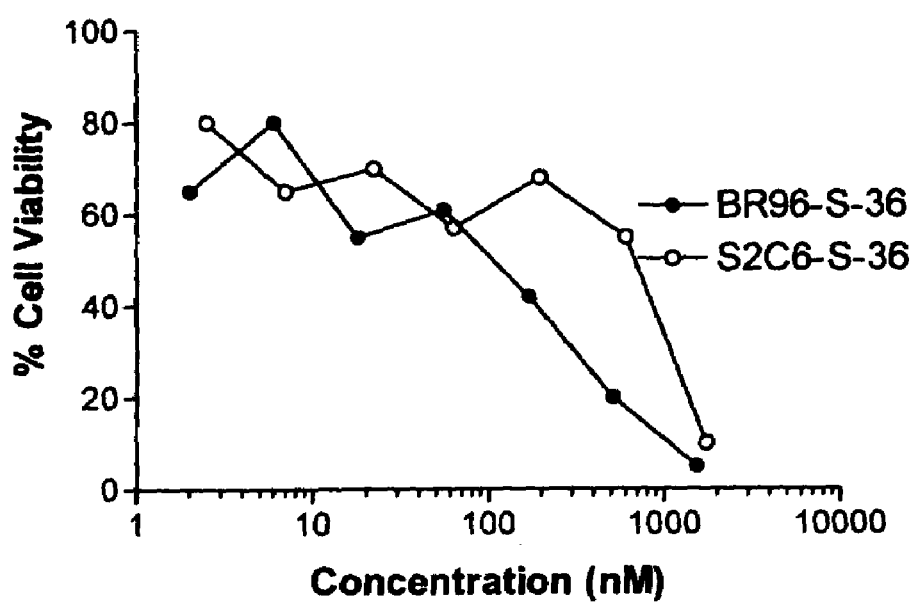

The cytotoxic effects of the mAb-S-36 conjugates on L2987 human lung adenocarcinoma cells (strongly BR96 antigen positive, weakly S2C6 antigen positive) and on Kato III human gastric carcinoma cells, (strongly BR96 antigen positive, S2C6 antigen negative) are shown in FIGS. 18A, 18B and 18C. These figures show the in vitro cytotoxicity of drugs and mAb-drug conjugates on (FIG. 18A) and (FIG. 18B) L2987 human lung adenoma cells, and (FIG. 18A) and (FIG. 18C) Kato III human gastric carcinoma cells. L2987 cells are positive for the antigens recognized by BR96 (LeY) and S2C6 (CD40), but express the LeY antigen at higher levels. Kato III cells are positive for the LeY antigen and negative for CD40. Cells were exposed to the conjugates for 2 hours, washed, and the cytotoxic effects were determined 3 days later using a thymidine incorporation assay.

Auristatin E (29a) and the ketone derivative 35 were at least 100-fold more cytotoxic than doxorubicin on L2987 and Kato III cells (FIG. 18A). On both cell lines, the BR96-S-36 conjugate displayed increased potency compared to S2C6-S-36, suggesting some degree of immunological specificity. The low potency of BR96-S-36 is most likely due to its stability at pH 5 (Table 5), suggesting that only a small portion of the conjugated drug is released under the assay conditions during a two day period.

Example 26

In Vitro Cytotoxicity Data for mAb-S-40a

Figure 19A:
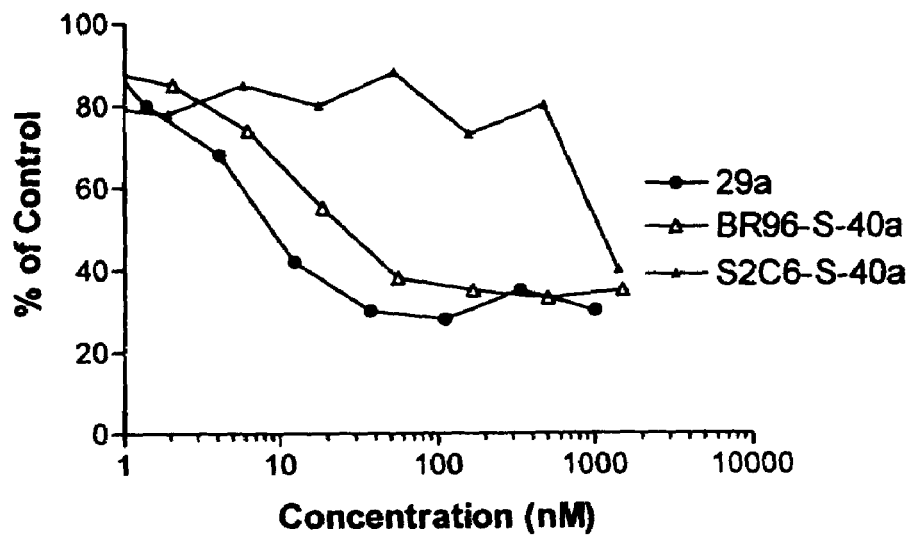
FIGS. 19A and 19B show the cytotoxic effects of auristatin E and auristatin E-containing conjugates on L2987 human lung adenocarcinoma cells (FIG. 19A) and various hematologic cell lines treated with AC10-S-40a (FIG. 19B).
Figure 19B:
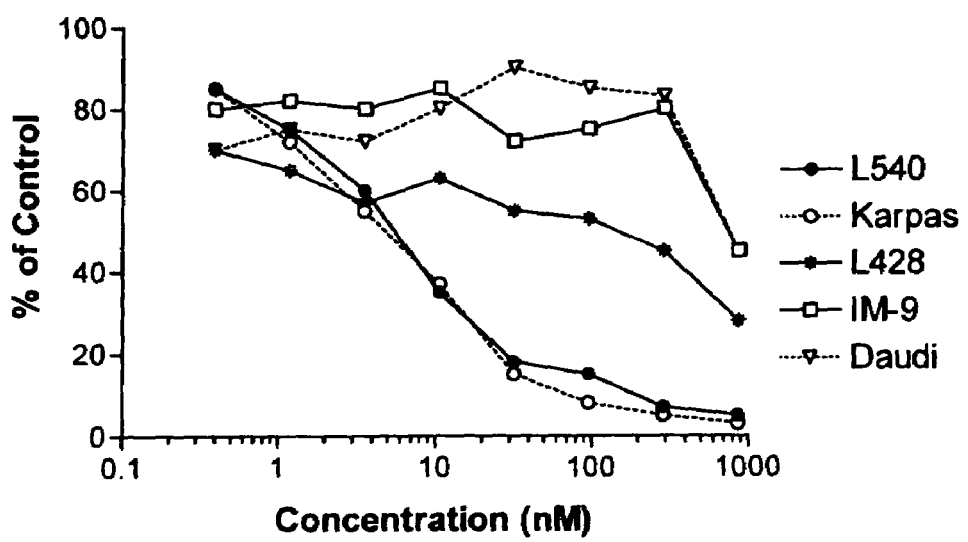

The cytotoxic effects of specific conjugates on several cell lines are shown in FIGS. 19A and 19B. These figures show the cytotoxic effects of auristatin E and auristatin E-containing conjugates on L2987 human lung adenocarcinoma cells (FIG. 19A); and various hematologic cell lines treated with AC10-S-40a (FIG. 19B). In all assays, cells were exposed to the drugs for 2 hours, washed, and the cytotoxic activities were measured 72 hours later using $^3$H-thymidine incorporation.

On L2987 cells (FIG. 19A), BR96-S-40a was significantly more cytotoxic than S2C6-S-40a, reflecting increased LeY antigen expression compared to CD40 (Table 1). The effects of the AC10-S-40a conjugate on several hematologic cell lines are shown in FIG. 19B. The most sensitive cells were L540 Hodgkin's lymphoma and Karpas anaplastic large cell lymphoma, both of which strongly express the CD30 antigen. The L428 cell line, which is intermediate in CD30 antigen expression, was affected to a lesser extent by the AC10-S-40a conjugate. The effects appeared to be immunologically specific, since the antigen-negative control cell line, Daudi, was quite insensitive to the conjugate. One of the interesting findings in this study was that IM-9, a strong expresser of the CD30 antigen (Table 1), was also insensitive to the AC10-S-40a conjugate. Upon further analysis, it was found that unlike the other cell lines, IM-9 did not internalize bound conjugate. Thus, these results demonstrate that activity requires not only specific binding, but also antigen internalization.

Example 27

In Vivo Activities of mAb-S-40a Conjugates

Figure 20A:
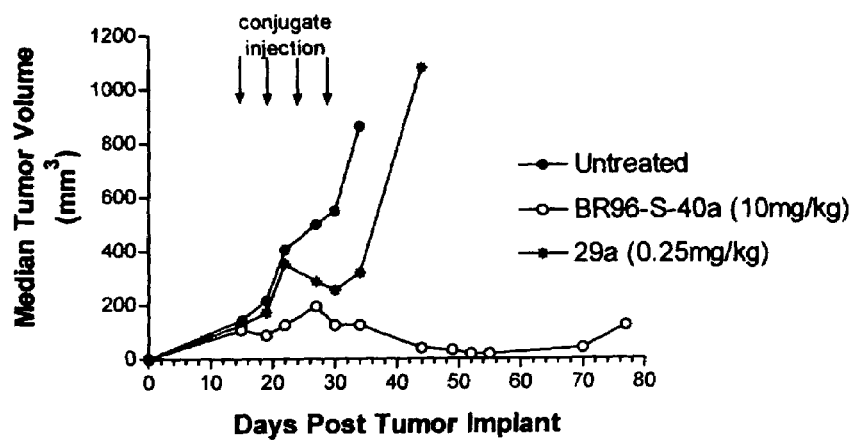
FIGS. 20A and 20B show median tumor volume observed when nude mice with subcutaneous L2987 human lung adenocarcinoma or 3396 human breast carcinoma xenografts were injected with conjugates or drug according to the schedule shown in the two Figures.
Figure 20B:
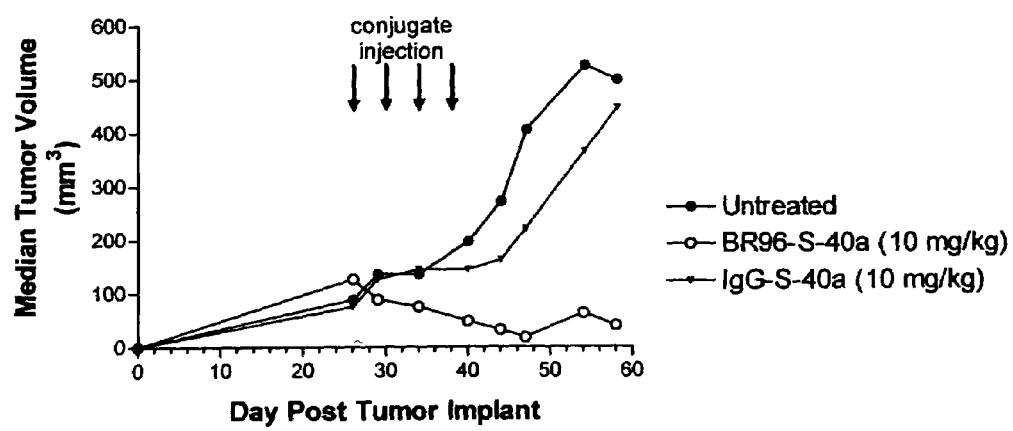

Nude mice with subcutaneous L2987 human lung adenocarcinoma or 3396 human breast carcinoma xenografts were injected with conjugates or drug according to the schedule shown in FIGS. 20A and 20B. The BR96-S-40a conjugates bound to the tumor lines, while the IgG-S-40a did not. All animals were monitored daily for general health, and every 3–8 days for weight and tumor growth. Tumor volumes were estimated using the formula: (longest dimension)×dimension perpendicular$^2$/2. There was no toxicity associated with the mAb-S-40a conjugates. The effects were compared to those of auristatin E at the maximum tolerated dose. Estradiol implants were used to sustain the growth of 3396 tumors. The implants released estradiol over a period of 60 days, at which point the experiment was terminated.

Example 28

In Vitro Cytotoxicity Data for mAb-S-40A, mAb-S-48, mAb-S-51, and mAb-S-59

Figure 21:
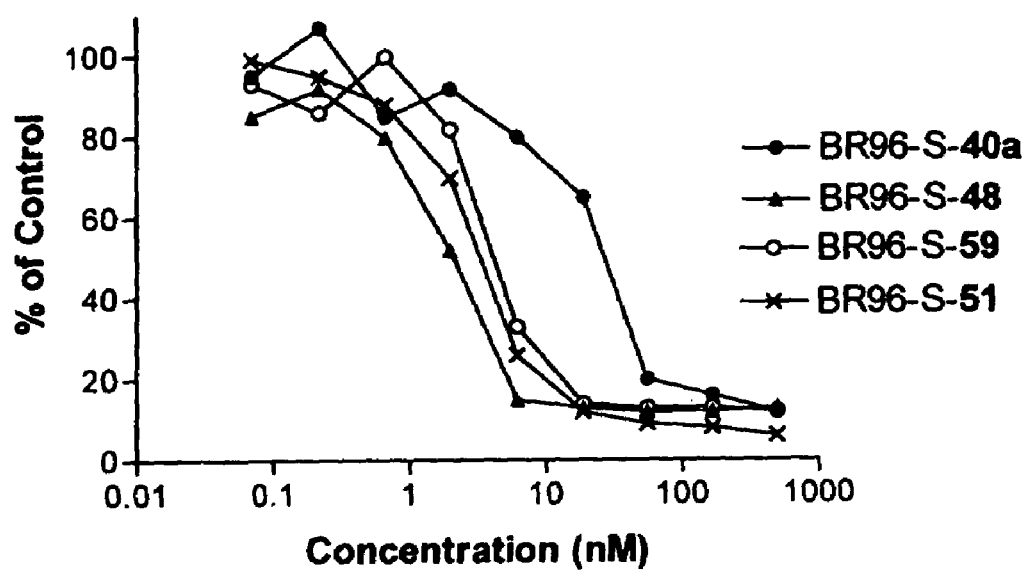
FIG. 21 shows the cytotoxic effects of drug conjugates of the invention on H3396 human breast carcinoma cells.

The cytotoxic effects of the conjugates on H3396 human breast carcinoma cells (strongly BR96 antigen positive) are shown in FIG. 21. To obtain this data, L2987 cells in RPMI medium were plated into 96-well plates (5,000 cells/well), and after 24 hours at 37° C., various concentrations of the conjugates in medium (0.05 mL) were added to triplicate samples. After 1 hour at 37° C., the cells were washed, and incubation was continued for an additional 24 hours, at which time the cells were washed again. The cytotoxic effects were determined after an additional 3 days using XTT as an indicator of cell viability. The data show that while all the conjugates are highly cytotoxic to H3396 cells, the BR96 conjugates prepared from compounds 48, 51 and 59 are more potent then BR96-40a.

All publications and patent applications mentioned in this specification are herein incorporated by reference to the same extent as if each individual publication or patent application was specifically and individually incorporated by reference. For example, the book in *Comprehensive Organic Transformations, A Guide to Functional Group Preparations*, Second Edition, Richard C. Larock, John Wiley and Sons, Inc., 1999, and particularly the references cited therein, is incorporated herein by reference for all purposes.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:
1. A compound of the formula:

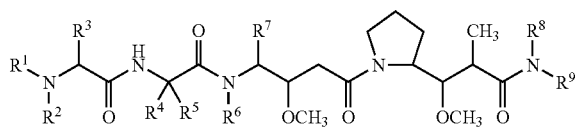

and pharmaceutically acceptable salts and solvates thereof,
wherein, independently at each location:
$R^1$ is selected from hydrogen and lower alkyl;
$R^2$ is selected from hydrogen and lower alkyl;
$R^3$ is lower alkyl;
$R^4$ is selected from lower alkyl, aryl, and —CH$_2$—C$_{5-7}$ carbocycle when $R^5$ is selected from H and methyl, or $R^4$ and $R^5$ together form a carbocycle of the partial formula —(CR$^a$R$^b$)$_n$— wherein R$^a$ and R$^b$ are independently selected from hydrogen and lower alkyl and n is selected from 2, 3, 4, 5 and 6;
$R^6$ is selected from hydrogen and lower alkyl;
$R^7$ is sec-butyl or iso-butyl;
$R^8$ is selected from hydrogen and lower alkyl;
$R^9$ is selected from

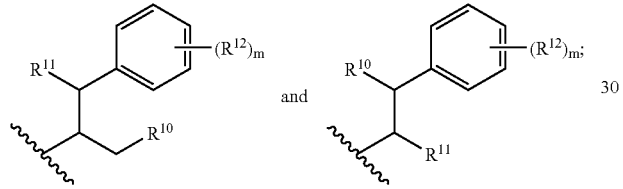

$R^{10}$ is selected from

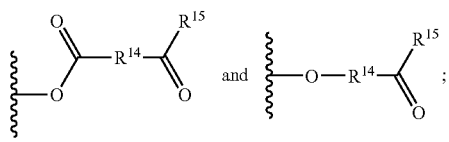

$R^{11}$ is selected from hydrogen and lower alkyl;
$R^{12}$ is selected from lower alkyl, halogen, and methoxy, and m is 0–5 where $R^{12}$ is independently selected at each occurrence;
$R^{14}$ is selected from a direct bond, arylene (lower alkylene), lower alkylene and arylene; and
$R^{15}$ is selected from hydrogen, lower alkyl and aryl.

2. The compound of claim 1 wherein $R^{10}$ is

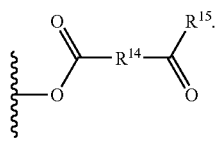

3. The compound of claim 1 wherein $R^{10}$ is

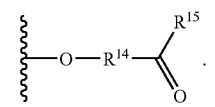

4. The compound of claim 1 having the structure

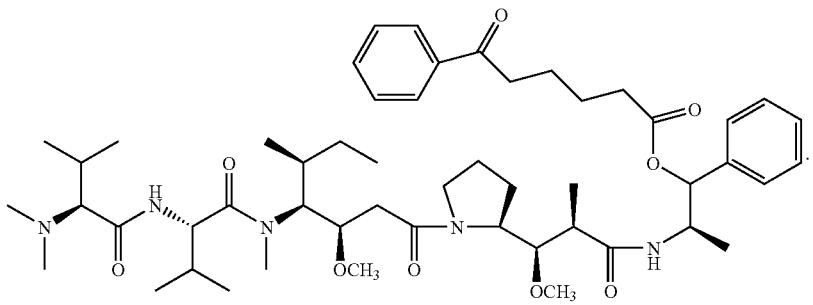

5. The compound of claim 1 having the structure

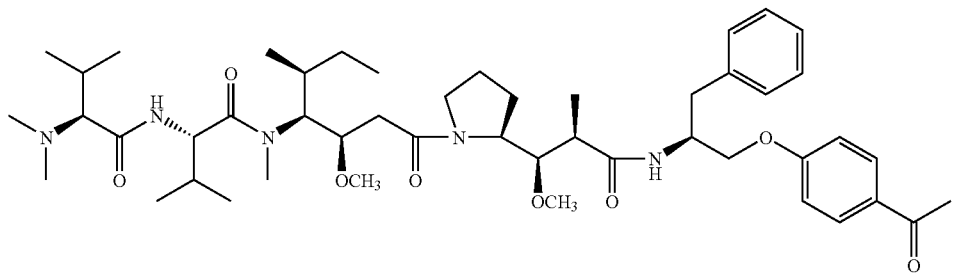

6. The compound of claim 1 having the structure
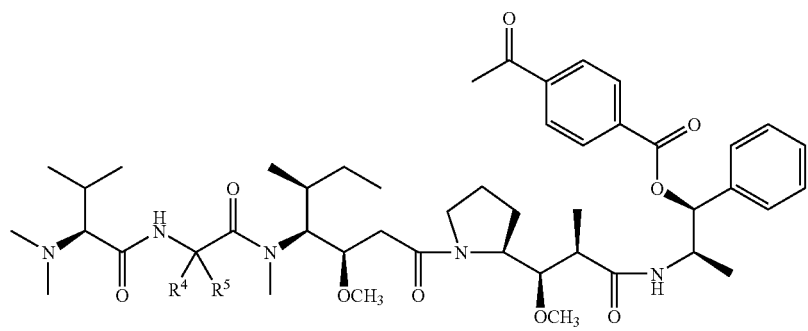
wherein $R^4$ is iso-propyl or sec-butyl and $R^5$ is hydrogen.